United States Patent
Togino

(10) Patent No.: US 10,330,914 B2
(45) Date of Patent: Jun. 25, 2019

(54) STEREOSCOPIC IMAGING OPTICAL SYSTEM ASSEMBLY, STEREOSCOPIC IMAGING APPARATUS, AND ENDOSCOPE

(71) Applicant: OLYMPUS CORPORATION, Tokyo (JP)

(72) Inventor: Takayoshi Togino, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 779 days.

(21) Appl. No.: 14/861,810

(22) Filed: Sep. 22, 2015

(65) Prior Publication Data
US 2016/0070094 A1   Mar. 10, 2016

Related U.S. Application Data

(63) Continuation of application No. PCT/JP2013/069307, filed on Jul. 16, 2013.

(30) Foreign Application Priority Data

Mar. 22, 2013  (JP) .................. 2013-059953

(51) Int. Cl.
*A61B 1/00* (2006.01)
*G02B 7/04* (2006.01)
(Continued)

(52) U.S. Cl.
CPC ...... *G02B 23/2415* (2013.01); *A61B 1/00193* (2013.01); *G02B 7/04* (2013.01);
(Continued)

(58) Field of Classification Search
CPC .. A61B 1/00193; G02B 7/06; G02B 23/2415; G02B 23/243; G02B 27/2242; G02B 7/16; G03B 35/08; H04N 13/204; H04N 13/211
See application file for complete search history.

(56) References Cited

U.S. PATENT DOCUMENTS 6,414,791 B1    7/2002  Sugawara
2005/0185050 A1  8/2005  Ohashi
(Continued)

FOREIGN PATENT DOCUMENTS

JP   H06175033 A   6/1994
JP   H07152096 A   6/1995
(Continued)

OTHER PUBLICATIONS

International Search Report dated Oct. 29, 2013 corresponding to PCT/JP2013/069307.

*Primary Examiner* — Aaron B Fairchild
(74) *Attorney, Agent, or Firm* — Scully, Scott, Murphy & Presser, P.C.

(57) ABSTRACT

A stereoscopic imaging optical system assembly including a first optical system at least including, in order from an object side to an image plane side, a negative lens and an aperture, the first optical system being rotationally symmetric with respect to a first center axis, a second optical system that is rotationally symmetric with respect to a second center axis parallel with the first center axis, and that has the same construction as, and is located in parallel with, the first optical system, and a variable optical system located in such a way as to intersect the respective optical paths through the first optical system and the second optical system. The variable optical system effects a change of at least either one of focus and vergence.

11 Claims, 83 Drawing Sheets

(51) Int. Cl.
  *G02B 7/06* (2006.01)
  *G02B 7/16* (2006.01)
  *G03B 3/10* (2006.01)
  *G03B 5/00* (2006.01)
  *G02B 13/04* (2006.01)
  *G02B 23/24* (2006.01)
  *G03B 35/08* (2006.01)
  *H04N 13/204* (2018.01)
  *H04N 13/218* (2018.01)
  *H04N 13/239* (2018.01)
  *G03B 35/10* (2006.01)
  *H04N 5/225* (2006.01)
  *G02B 27/22* (2018.01)
  *H04N 13/211* (2018.01)

(52) U.S. Cl.
  CPC .............. *G02B 7/06* (2013.01); *G02B 7/16* (2013.01); *G02B 13/04* (2013.01); *G02B 23/243* (2013.01); *G03B 5/00* (2013.01); *G03B 35/08* (2013.01); *G03B 35/10* (2013.01); *H04N 5/2254* (2013.01); *H04N 13/204* (2018.05); *H04N 13/218* (2018.05); *H04N 13/239* (2018.05); *G02B 27/2214* (2013.01); *G03B 3/10* (2013.01); *G03B 2205/0092* (2013.01); *H04N 13/211* (2018.05); *H04N 2005/2255* (2013.01); *H04N 2213/001* (2013.01)

(56) References Cited

U.S. PATENT DOCUMENTS

2010/0208046 A1  8/2010  Takahashi
2013/0170029 A1  7/2013  Morita

FOREIGN PATENT DOCUMENTS

| JP | 200019663 A | 1/2000 | | |
|---|---|---|---|---|
| JP | 2003005313 A | 1/2003 | | |
| JP | 2005241791 A | 9/2005 | | |
| JP | 2010128354 A2 | 6/2010 | | |
| JP | 2010271429 A | 12/2010 | | |
| JP | 2011070119 A | 4/2011 | | |
| JP | 2012113281 A | 6/2012 | | |
| JP | 2012198414 A | 10/2012 | | |
| JP | 2013017096 A | 1/2013 | | |
| JP | 2013109009 A | * | 6/2013 | ............ G02B 13/16 |
| WO | WO2012017684 A1 | 2/2012 | | |

* cited by examiner

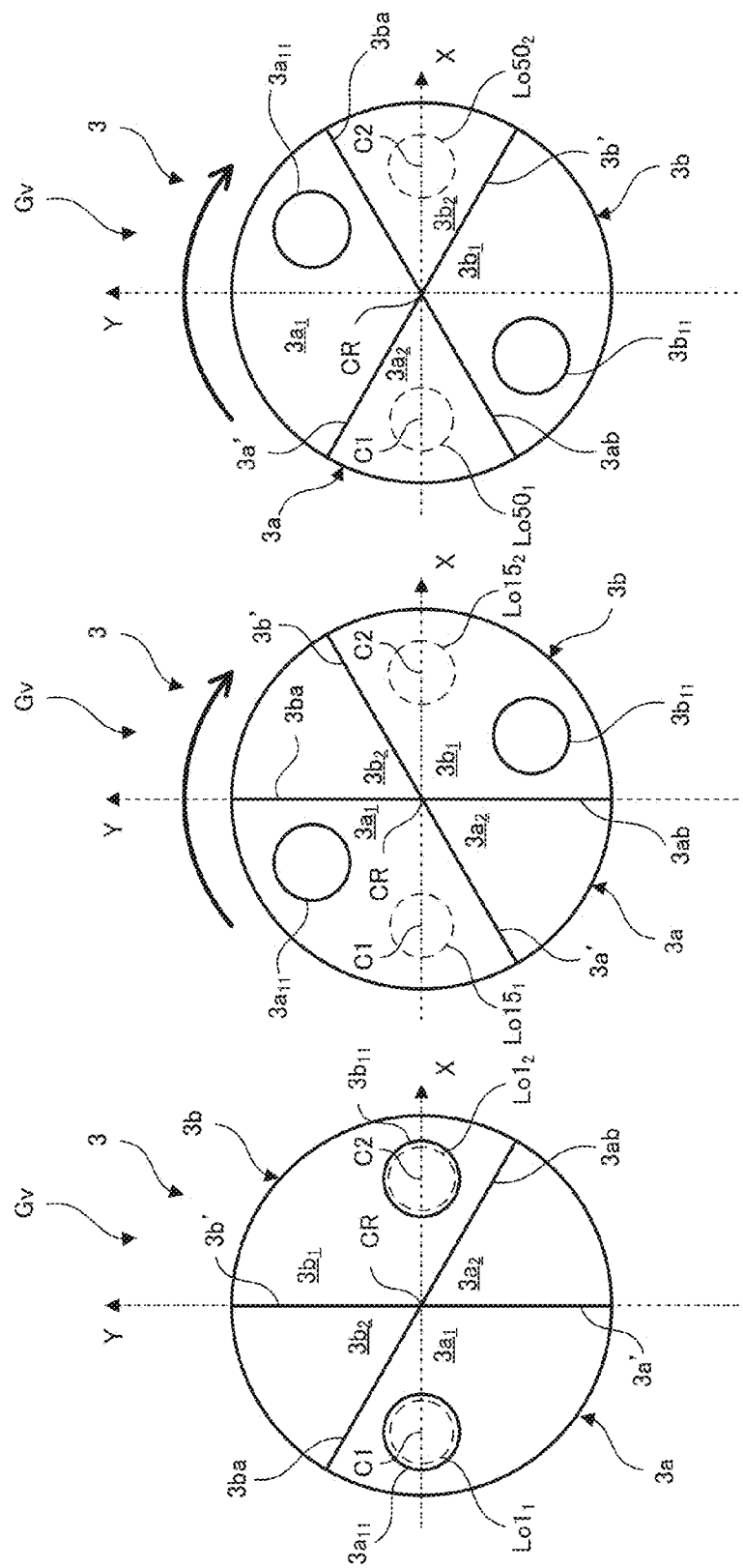

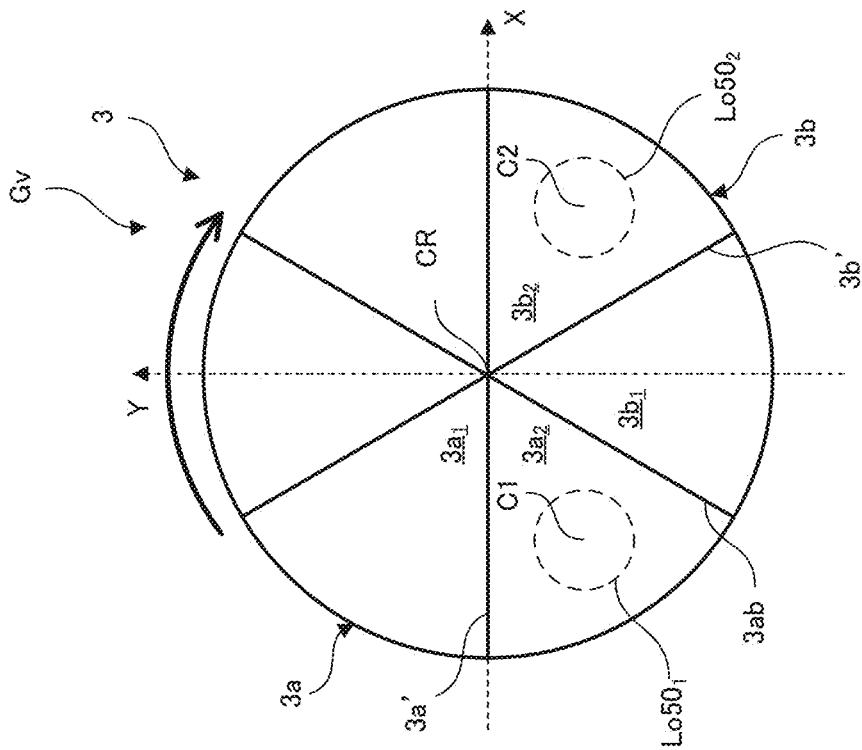
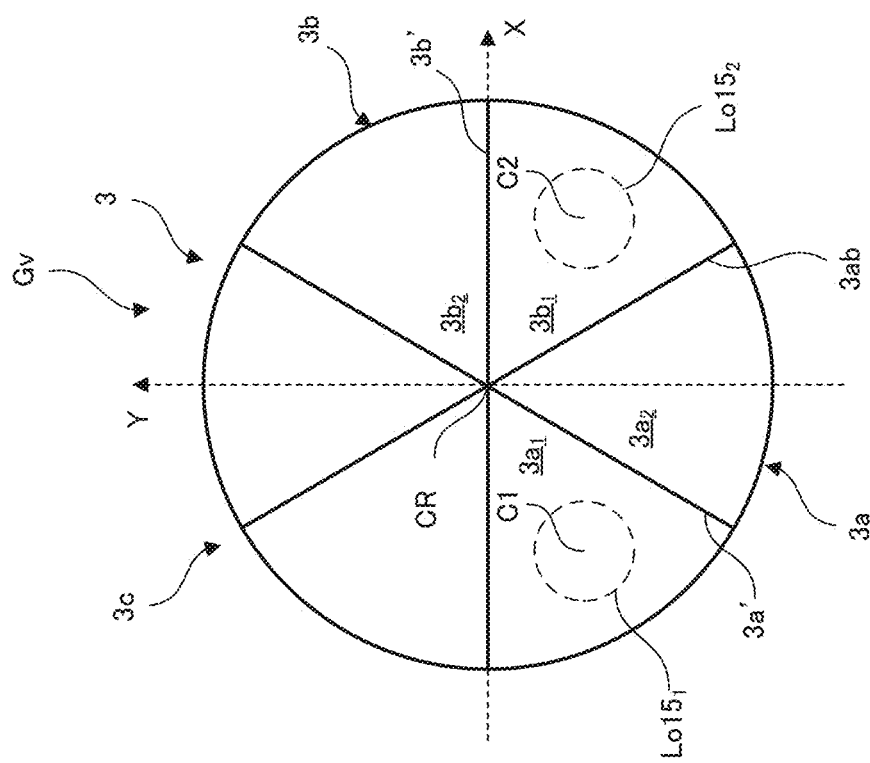
FIG.5A
FIG.5B

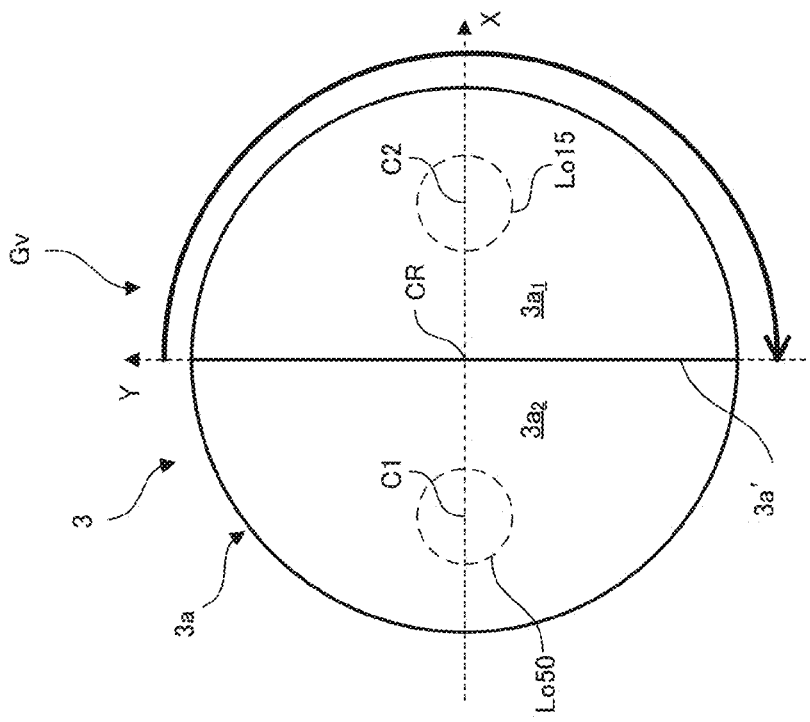
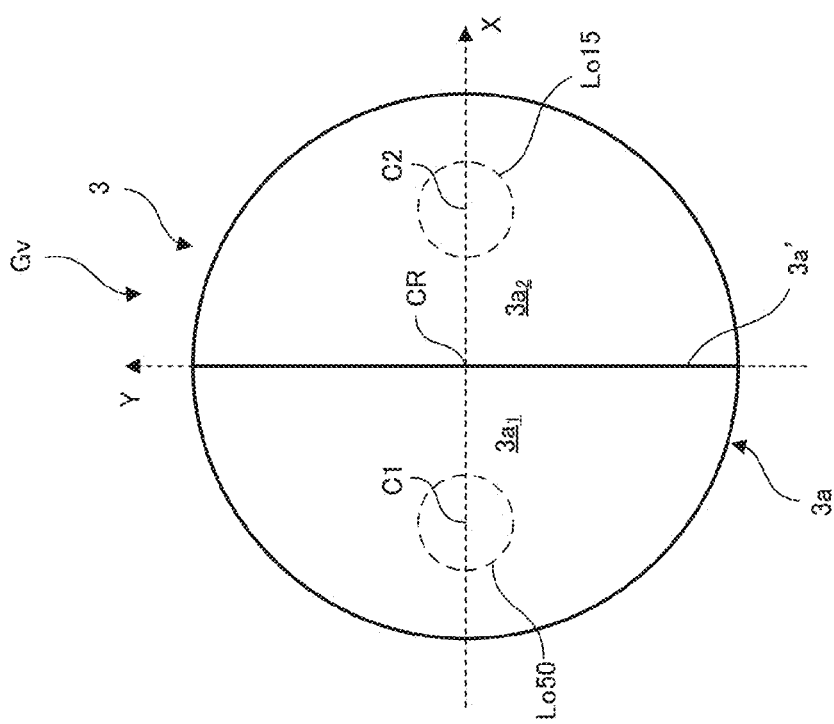
FIG.6A
FIG.6B

Example 1

Example 1(Far point)

Example 1(Far point)

FIG.20 Example 1 (Near point)

FIG.21 Example 1 (Near point)

FIG.26 Example5 (Far point)

FIG.28 Example5 (Near point)

FIG.29 Example 6

FIG.31 Example6 (Far point)

FIG.35 Example 7

FIG.38  Example 7 (Near point)

Example 8

FIG.42 Example 8 (Far point)

FIG.44 Example 8 (Near point)

FIG.45 Example 8 (Near point)

Example9

Example 9

FIG.49 Example9

FIG.50 Example9 (Far point)

FIG.51 Example 9 (Far point)

FIG.52 Example9 (Near point)

FIG.53 Example9 (Near point)

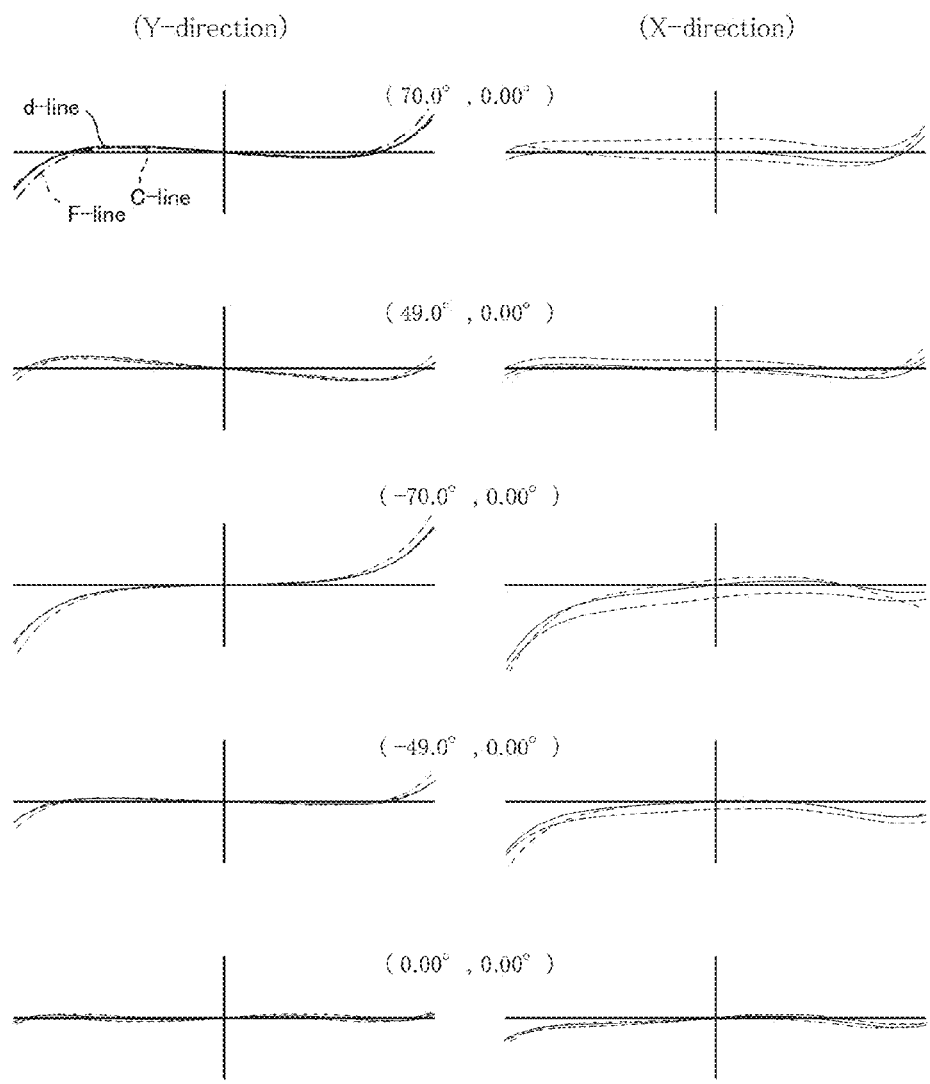
FIG.57 Example10(Far point)

FIG.59 Example10 (Near point)

FIG.63 Example11 (Intermediate)

Example11 (Near point)

FIG.67 Example12 (Far point)
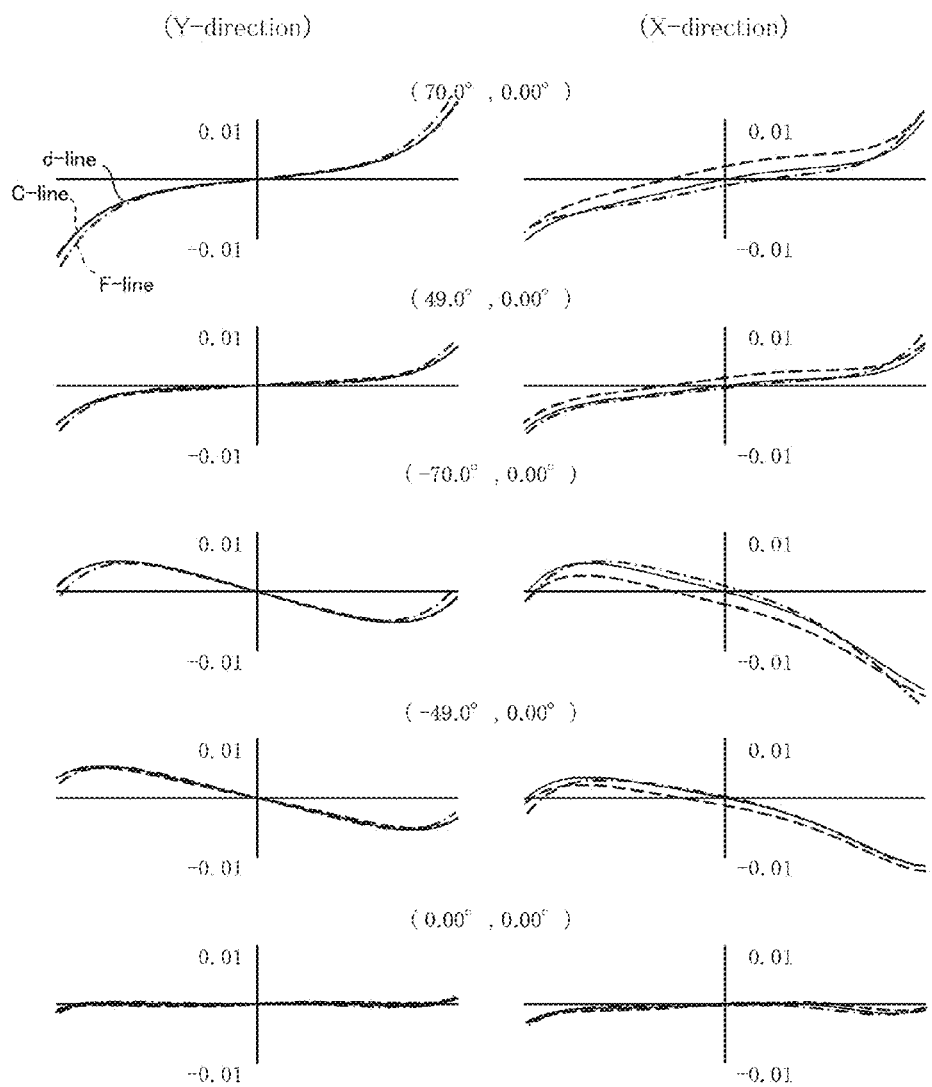

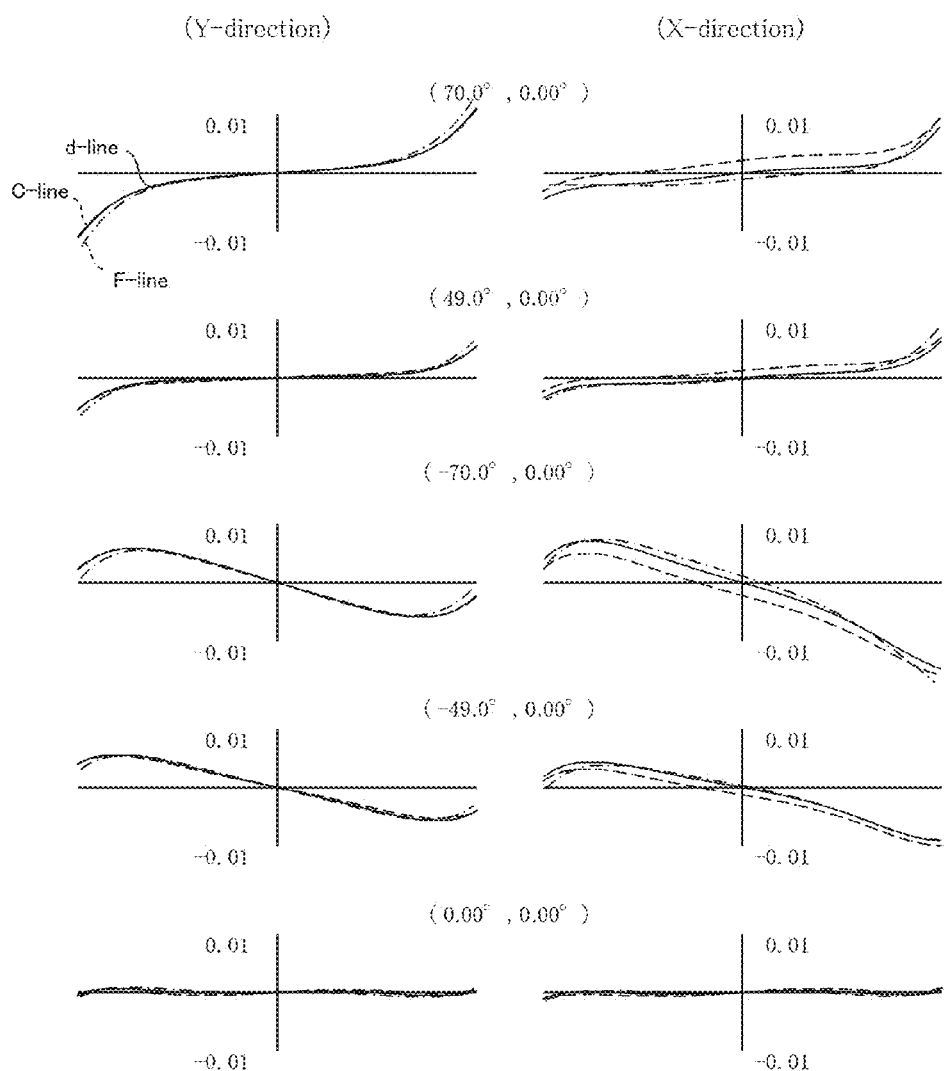
FIG.68  Example 12 (Intermediate)

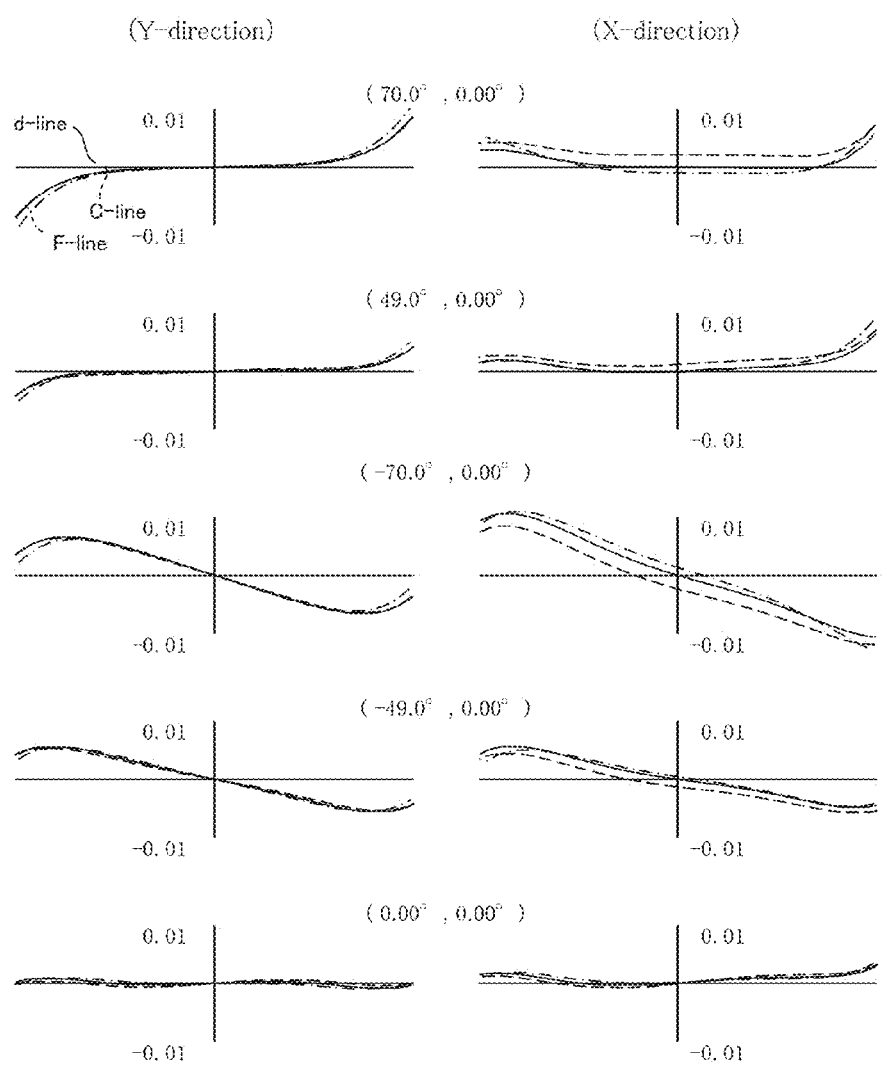
FIG.69 Example12 (Near point)

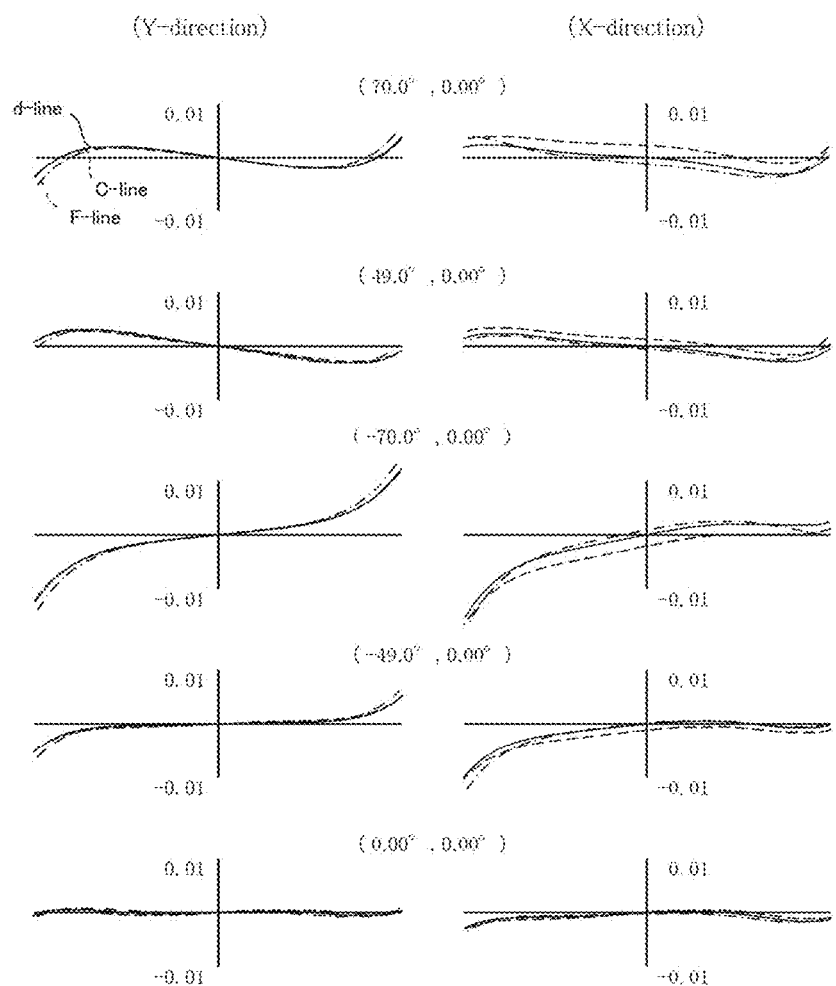
FIG.72 Example13 (Far point)

FIG.73  Example13 (Intermediate)
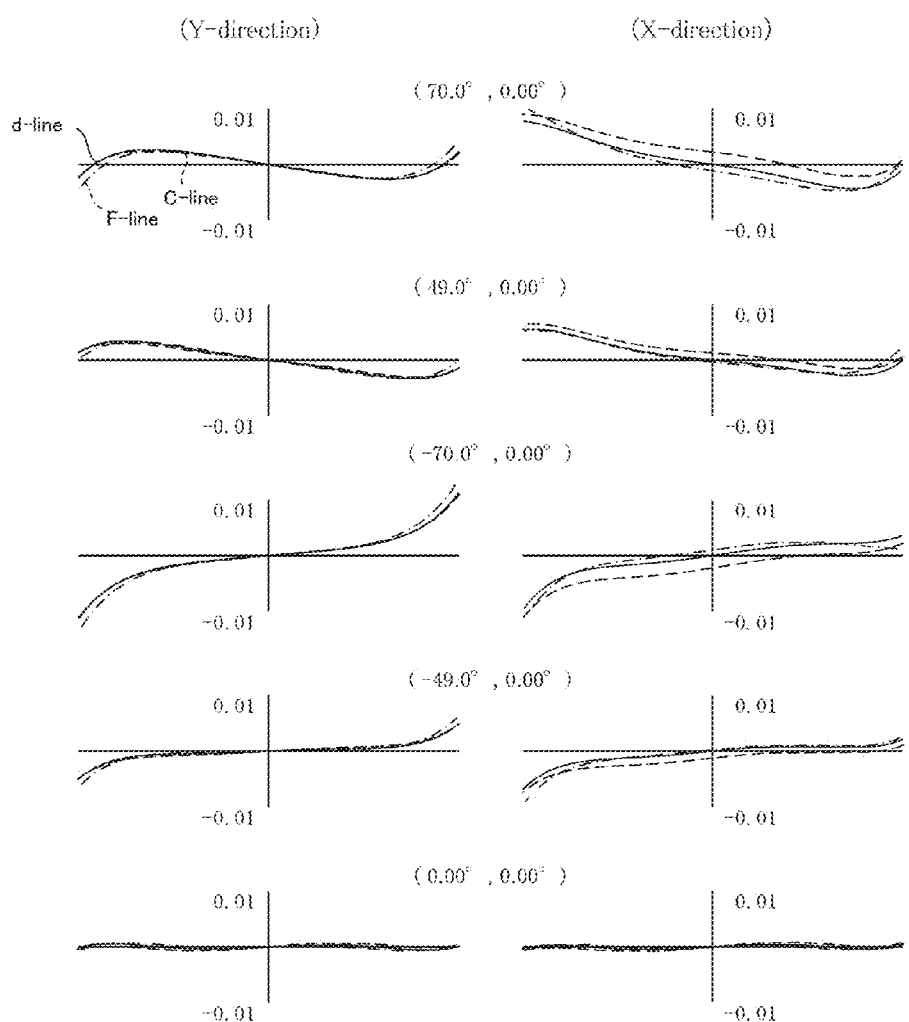

FIG.74  Example13(Near point)
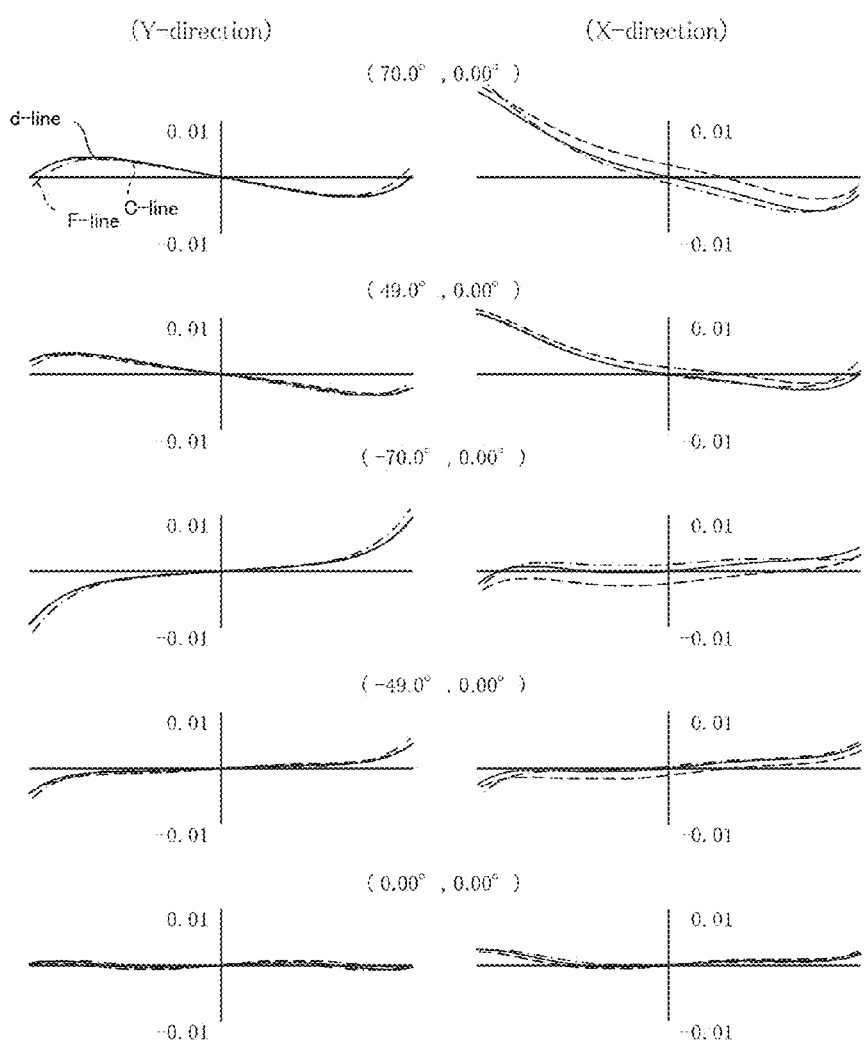

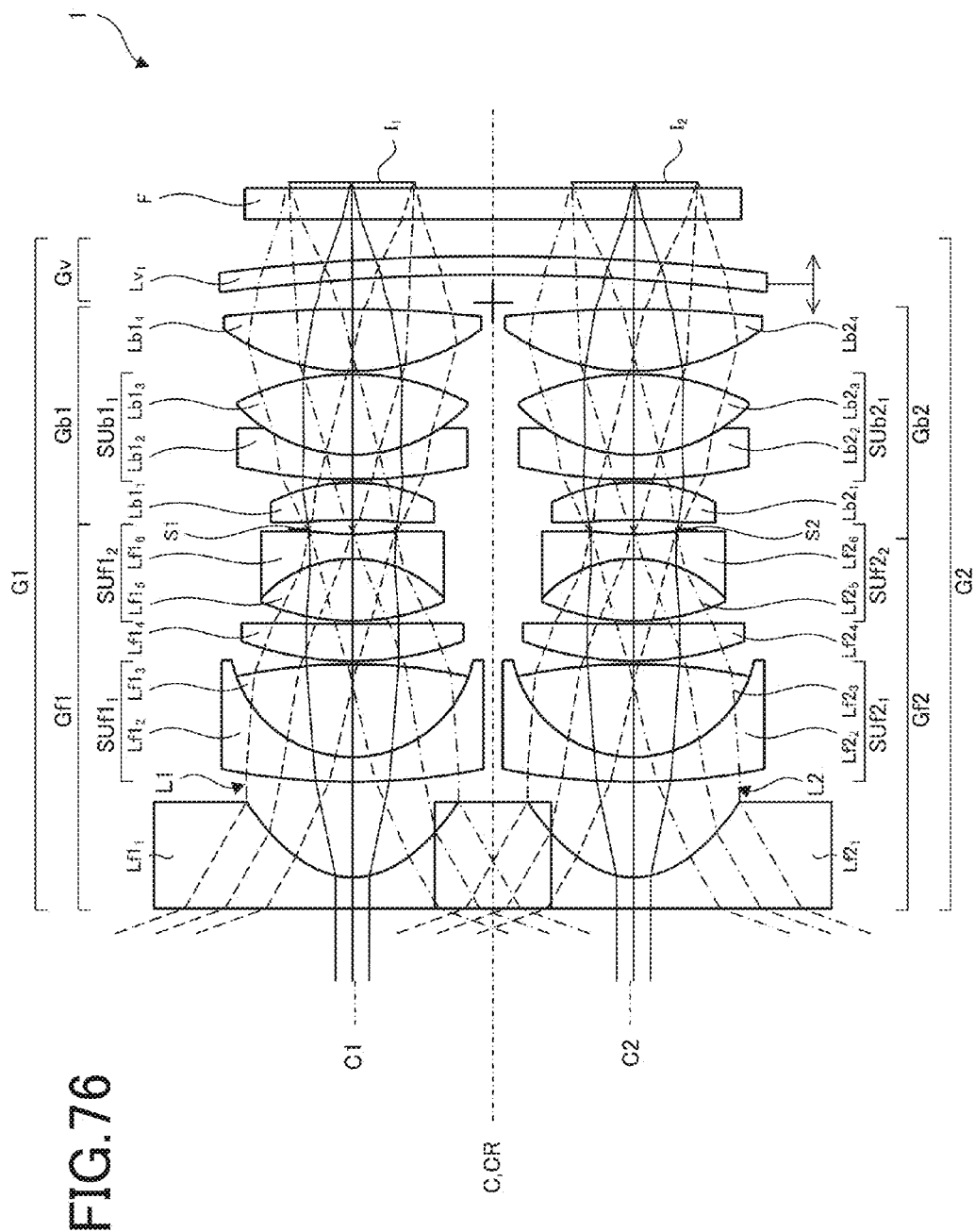

FIG.78  Example14(Far point)
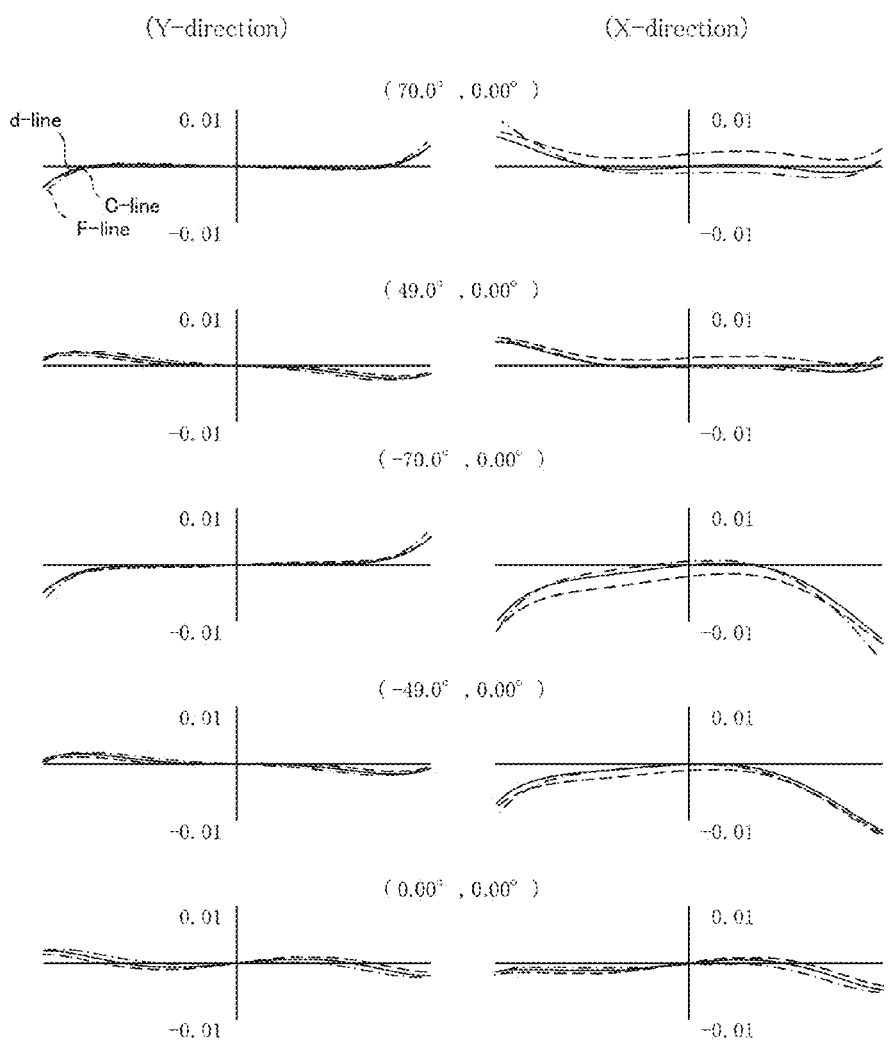

FIG.79  Example 14 (Intermediate)
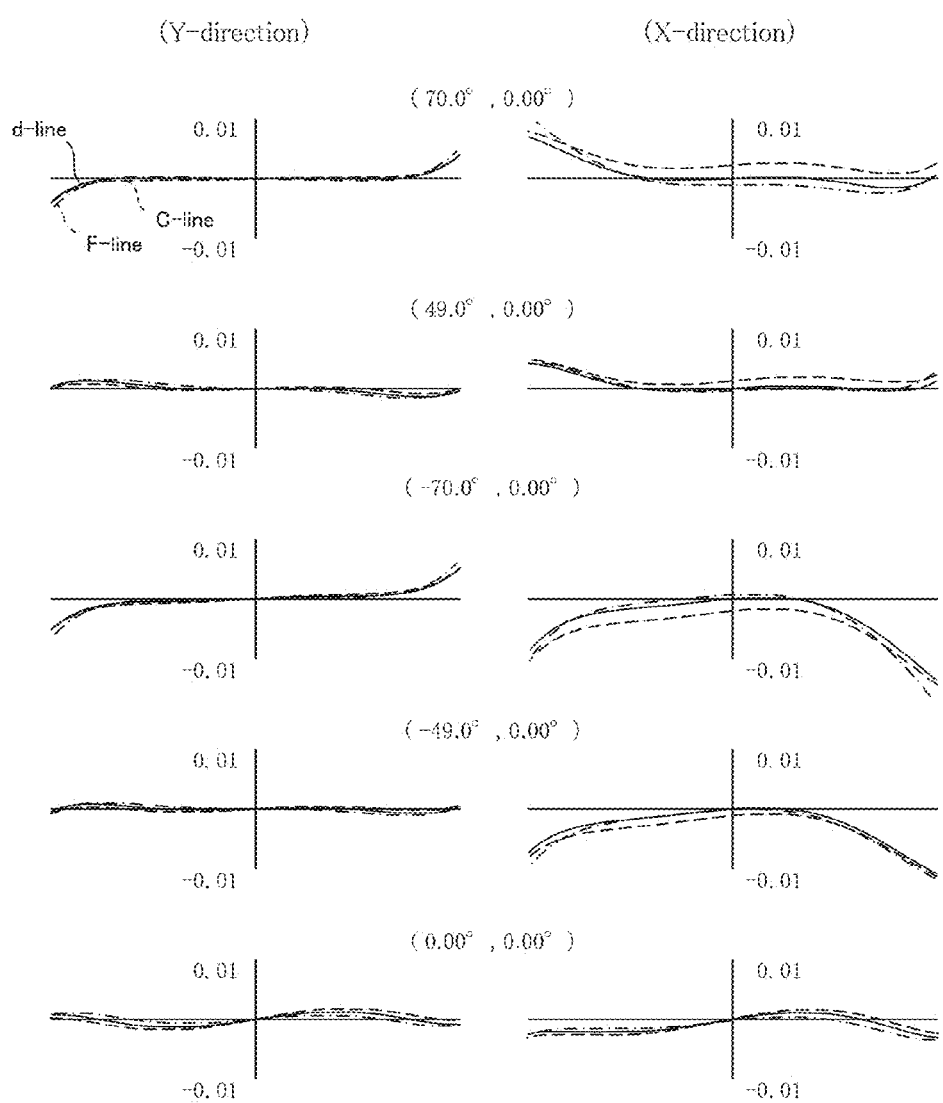

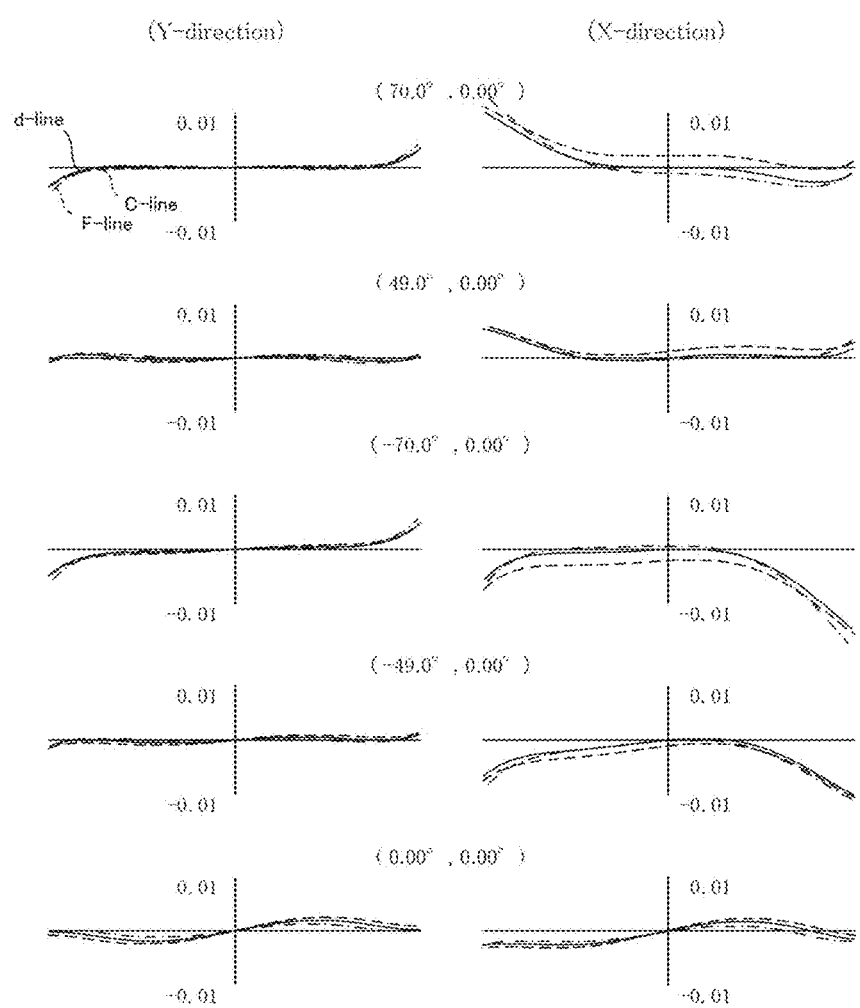
FIG.80  Example14(Near point)

STEREOSCOPIC IMAGING OPTICAL SYSTEM ASSEMBLY, STEREOSCOPIC IMAGING APPARATUS, AND ENDOSCOPE

CROSS-REFERENCE TO RELATED APPLICATIONS

The present application is a continuation application of International Application No. PCT/JP2013/069307, filed Jul. 16, 2013. The contents of these applications are incorporated herein by reference in their entirety.

BACKGROUND OF THE INVENTION AND RELATED ART STATEMENT

In one embodiment, the invention provides a stereoscopic imaging optical system assembly adapted to take images having parallaxes for stereoscopic observations, a stereoscopic imaging apparatus and an endoscope assembly.

So far, a stereoscopic imaging optical system adapted to take two images having different parallaxes for stereoscopic observations has been typically comprised of two imaging optical systems arranged in parallel (see Patent Publication 1). Patent Publication 2 discloses a microscopic optical system for enlarged observations wherein an optical system having a single center axis is located on the object side, and Patent Publication 3 discloses a stereoscopic imaging optical system for a binocular stereomicroscope.

Patent Publication 1: JP(A) 2012-113281
Patent Publication 1: JP(A) 6-175033
Patent Publication 2: JP(A) 2011-70119

SUMMARY OF THE INVENTION

In one embodiment, the present invention provides a stereoscopic imaging optical system assembly, comprising:
a first optical system that includes, in order from an object side to an image plane side, at least a negative lens and an aperture and is rotationally symmetric with respect to a first center axis,
a second optical system that is rotationally symmetric with respect to a second center axis parallel with said first center axis, has the same construction and arrangement as, and is located in parallel with, said first optical system, and
a variable optical system that is located in such a way as to intersect the respective optical paths through said first optical system and said second optical system, characterized in that:
said variable optical system includes at least one variable optical element capable of changing at least either one of focus and vergence.

In one embodiment, the present invention provides a stereoscopic imaging apparatus characterized by including said stereoscopic imaging optical system assembly, and an imaging device located at said image plane and comprising a plurality of pixels.

In one embodiment, the present invention provides an endoscope, characterized by including said stereoscopic imaging apparatus.

BRIEF DESCRIPTION OF THE DRAWINGS

FIGS. 4A, 4B and 4C are illustrative of the variable optical element 3 shown in FIG. 3, as viewed from the direction of the center axis of rotation CR.

FIGS. 5A and 5B are illustrative of another example of the variable optical element 3, as viewed from the direction of the center axis of rotation CR.

FIGS. 6A and 6B are illustrative of yet another example of the variable optical element 3, as viewed from the direction of the center axis of rotation CR.

FIG. 57 is an aberration diagram at a far point for Example 10 of the stereoscopic imaging optical system assembly 1.

FIG. 67 is an aberration diagram at a far point for Example 12 of the stereoscopic imaging optical system assembly 1.

FIG. 68 is an aberration diagram in an intermediate state for Example 12 of the stereoscopic imaging optical system assembly 1.

FIG. 69 is an aberration diagram at a near point for Example 12 of the stereoscopic imaging optical system assembly 1.

FIG. 72 is an aberration diagram at a far point for Example 13 of the stereoscopic imaging optical system assembly 1.

FIG. 73 is an aberration diagram in an intermediate state for Example 13 of the stereoscopic imaging optical system assembly 1.

FIG. 74 is an aberration diagram at a near point for Example 13 of the stereoscopic imaging optical system assembly 1.

FIG. 76 is a sectional view of Example 14 of the stereoscopic imaging optical system assembly 1, as taken along its center axis C.

FIG. 78 is a transverse aberration diagram at a far point for Example 14 of the stereoscopic imaging optical system assembly 1.

FIG. 79 is a transverse aberration diagram in an intermediate state for Example 14 of the stereoscopic imaging optical system assembly 1.

FIG. 80 is an aberration diagram at a near point for Example 14 of the stereoscopic imaging optical system assembly 1.

DETAILED DESCRIPTION OF PREFERRED EMBODIMENTS

All of the optical systems disclosed in Patent Publications 1, 2 and 3 have a narrow angle of view and are of no small size.

The present invention provides a stereoscopic imaging optical system assembly of smaller size capable of obtaining a stereoscopic image having a wide angle of view, a stereoscopic imaging apparatus, and an endoscope.

The stereoscopic imaging optical system assembly 1 according to one embodiment of the invention is now explained.

Figure 1:
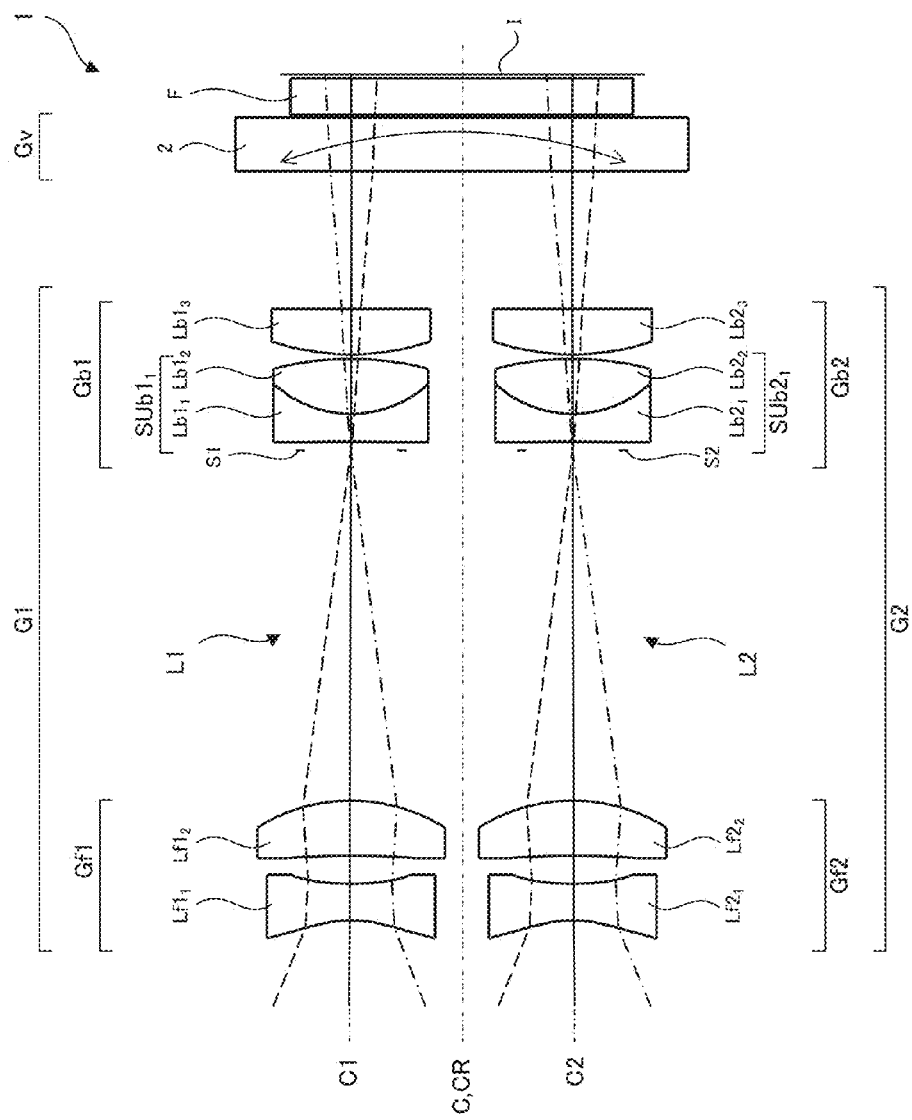
FIG. 1 is a sectional view of the stereoscopic imaging optical assembly 1 according to one embodiment of the invention, as taken along its center axis C.

FIG. 1 is a sectional view of the stereoscopic imaging optical system assembly 1 according to one embodiment of the invention, as taken along its center axis C.

So far stereoscopic imaging has typically been implemented in the following three ways:
1. Imaging is implemented through an optical system comprising completely independent two center axes;
2. Imaging is implemented through an optical system having generally a single center axis and designed to obtain parallaxes by means of pupil division; and
3. Imaging is implemented through an optical system comprising a front group having two center axes, located on the object side, and a rear group having one center axis.

In the imaging method using the optical system described in 1, the two center axes must be interlocked for their adjustment by a mechanical or electrical linkage, resulting in an oversize apparatus having a complicated structure. In the imaging method using the optical system described in 2, any wide angle of view is unachievable without recourse to a retrofocus type power layout wherein a strong negative lens is located on the object side or there is a large optical system needed for making an entrance pupil separation wide. In the imaging method using the optical system described in 3, as the angle of view gets wide, laterally asymmetric image distortion occurring at the decentered front group becomes large, possibly leading to a misjudgment of depth dimension upon stereoscopic observations.

A conventional stereoscopic imaging apparatus has a large depth of focus and dispenses with focus control, because an imaging device has a pixel number of the order of 300,000 as an example and a large F-number.

In recent years, an imaging device having smaller size yet having a greater pixel number has been reduced to practical use so that even in low image heights, high-resolution imaging can be implemented. For instance, in order to implement high-resolution imaging in a pixel number exceeding 1,000,000, an imaging optical system should have a small F-number and keep resolution limit small. This in turn requires a swallow depth of focus and focus control.

With the stereoscopic imaging optical system assembly 1 according to the invention, it is possible to obtain stereoscopic images having a small size, a high resolution and a wide angle of view.

In one embodiment of the invention, therefore, the stereoscopic imaging optical system assembly 1 includes a first optical system G1 that comprises at least a negative lens $Lf1_1$ and an aperture S1 in order from the object side to the image plane side and is rotationally symmetric with respect to a first center axis C1, a second optical system G2 that is rotationally symmetric with respect to a second center axis C2 parallel with the first optical system C1 and has the same yet parallel construction and arrangement as the first optical system C1, and a variable optical system $G_V$ that is located in such a way as to intersect the respective optical paths through the first optical system G1 and second optical system G2, wherein the variable optical system $G_V$ includes a variable optical element 2 capable of changing at least either one of focus and vergence.

The negative lenses $Lf1_1$ and $Lf1_2$ are located on the object sides of the first G1 and the second optical system G2, respectively, and the apertures S1 and S2 are located in any desired positions on the image plane I side with respect to the negative lenses $Lf1_1$ and $Lf1_2$, respectively. Preferably, the variable optical system GV includes at least one variable optical element 2 for changing or varying at least either one of focus and vergence.

With this construction and arrangement wherein the negative lenses $Lf_1$, $Lf_2$ are located on the object sides of the first G1 and the second optical system G2 and the apertures S1, S2 are located in any desired positions on the image plane I side with respect to the negative lenses $Lf_1$, $Lf_2$, it is possible to take stereoscopic images having parallaxes so that an asymmetric image distortion-free, relatively near object point of less than 100 mm and having a wide angle of view can be stereoscopically observed quite normally.

Further, the variable optical system $G_V$ includes at least one variable optical element 2 capable of changing or varying at least either one of focus and vergence of the first G1 and the second optical system G2. With this variable optical element 2, the characteristics of the first G1 and the second optical system G2 can be changed all at once so that a compact imaging optical system assembly can be formed.

In the stereoscopic imaging optical system assembly according to one embodiment of the invention, the variable optical element 2 is capable of varying at least either one of focus and vergence of the first G1 and the second optical system G2 at the same time. It is thus possible to vary the characteristics of the first G1 and the second optical system G2 at the same time, thereby improving the performance of the optical assembly.

Preferably, the variable optical element 2 has a transmission surface for imparting equivalent refraction to the first G1 and the second optical system G2.

The equivalent refraction imparted to the first G1 and the second optical system G2 makes sure of quite normal stereoscopic observations.

Preferably, the first G1 and the second optical system G2 each include, in order from the object side to the image plane side, a front group Gf$_1$, Gf$_2$ having a negative lens Lf1$_1$, Lf1$_2$, an aperture S1, S2 and a rear group Gb1, Gb2, and the variable optical system G$_V$ is located on the image plane I side with respect to the front group Gf1, Gf2.

Location of the variable optical system G$_V$ on the image plane I side with respect to the front group Gf1, Gf2 makes it possible to reduce light beam changes.

Figure 2:
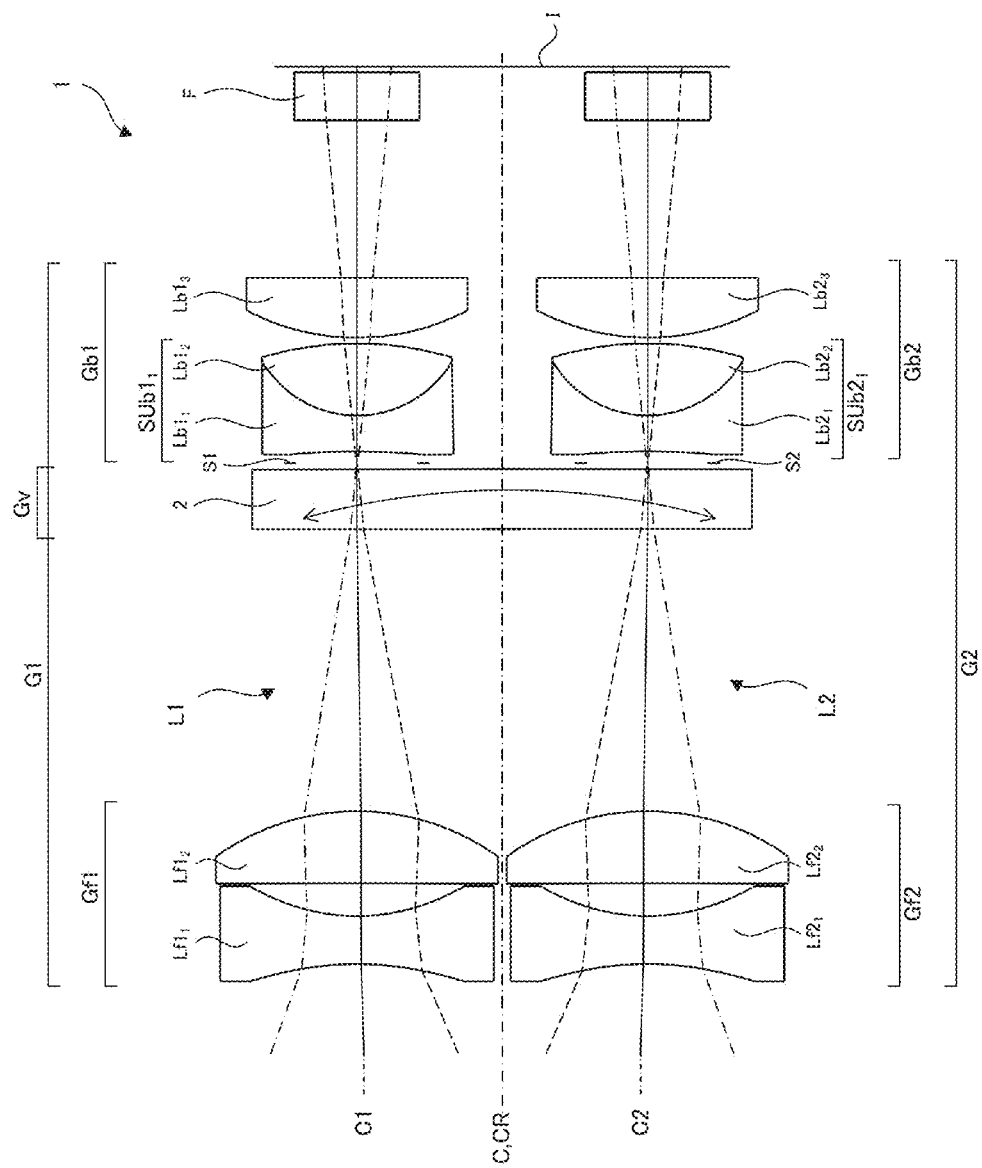
FIG. 2 is illustrative of the stereoscopic imaging optical assembly 1 according to one embodiment of the invention wherein the variable optical system $G_V$ is interposed between the front groups Gf1, Gf2 and the rear groups Gb1, Gb2.

FIG. 2 is illustrative of the stereoscopic imaging optical system assembly 1 according to one embodiment of the invention wherein the variable optical system G$_V$ is interposed between the front group Gf1, Gf2 and the rear group Gb1, Gb2.

Preferably, the variable optical system G$_V$ is interposed between the front group Gf1, Gf2 and the rear group Gb1, Gb2.

Interposition of the variable optical system G$_V$ between the front group Gf1, Gf2 and the rear group Gb1, Gb2 ensures that it comes close to the aperture S1, S2 so that focus can be varied without detrimental to off-axis aberrations and vergence can be varied with less image deterioration.

Preferably, the variable optical element 2 is rotatable around the single center axis of rotation CR.

As the variable optical element 2 rotates around the single center axis of rotation CR, it can intersect the respective optical paths through the first G1 and the second optical system G2 with a simple mechanism.

Preferably, the variable optical element 2 has a rotationally symmetric configuration with the center axis of rotation CR as an axis of symmetry.

The rotationally symmetric configuration of the variable optical element 2 with the center axis of rotation CR as an axis of symmetry ensures that it intersects the respective optical paths of the first G1 and the second optical system G2 so that at least either one of focus and vergence is variable.

Figure 3:
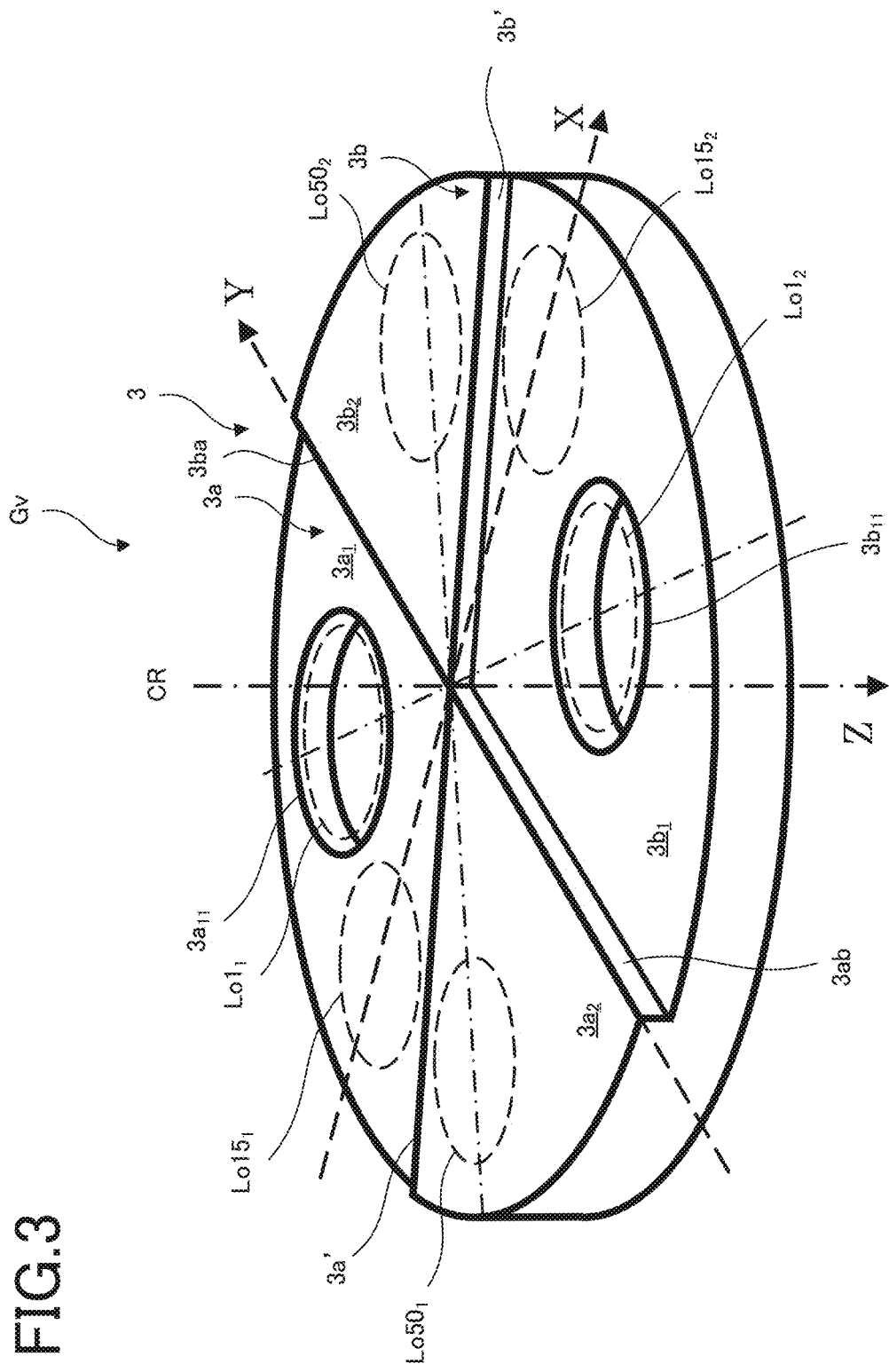
FIG. 3 is illustrative of one example of the variable optical element 3 including a planar portion.

FIG. 3 is illustrative of one example of the variable optical element 3 including a planar portion, and FIGS. 4A, 4B and 4C are illustrative of the variable optical element 3 shown in FIG. 3 as viewed from the direction of the center axis of rotation. FIGS. 4A, 4B and 4C are indicative of the first, second and third states of the variable optical element 3, respectively.

Preferably, the variable optical element G$_V$ includes the variable optical element 3. Preferably, the variable optical element 3 includes at least one set of a first surface portion 3a and a second surface portion 3b that has the same construction and arrangement as the first surface portion 3a and is located in a position rotated at a given angle relative to the first surface portion 3a with the center axis of rotation CR as center.

Since the variable optical element 3 includes at least one set of the first 3a and the second surface portion 3b having such construction and arrangement, at least either one of focus and vergence is variable by rotation of the variable optical system G$_V$.

Referring to the variable optical element 3, it is preferable that the first 3a, and the second surface portion 3b at least includes a first planar portion $3a_1$, $3b_1$, each comprising a plane orthogonal to the center axis of rotation CR, and a second planar portion $3a_2$, $3b_2$, each comprising a plane orthogonal to the center axis of rotation CR and having a thickness different in the direction of the center axis of rotation CR from that of the first planar portion $3a_1$, $3b_1$, respectively.

In the example shown in FIG. 3, the variable optical element 3 includes a first 3ab and a second boundary step 3ba formed at a boundary between the first 3a and the second surface portion 3b, and a first 3a' and second changeover step 3b' formed between the first $3a_1$, $3b_1$ and the second planar portion $3a_2$, $3b_2$, respectively.

The variable optical element 3 is also provided through the first planar portions $3a_1$, $3b_1$ with passage holes $3a_{11}$, $3b_{11}$ through which light beams Lo1$_1$, Lo1$_2$ from a 1-mm object point pass. And light beams Lo15$_1$, Lo15$_2$ from a 15-mm object point pass through the first planar portions $3a_1$, $3b_1$ while light beams Lo50$_1$, Lo50$_2$ from a 50-mm object point transmit through the second planar portions $3a_2$, $3b_2$.

In the variable optical element 3, the first 3a and the second surface portion 3b at least include the first planar portions $3a_1$, $3b_1$ and the second planar portions $3a_2$, $3b_2$, respectively. Therefore, rotation of the variable optical element 3 causes one optical path length to be changed over to another so that an appropriate angle of rotation can be determined depending on the object point distance for focusing. Note here that since there is no movement of an image point, the variable optical element 3 having any desired thickness may be located in any desired portion within the optical system assembly.

As shown typically in FIG. 4A, it is preferable that light beams Lo1$_1$, Lo1$_2$ from a 1-mm object point pass through the passage holes $3a_{11}$, $3b_{11}$ through the variable optical element 3 in the first state where the passage holes $3a_{11}$, $3b_{11}$ are aligned with and superposed on the center axis C1 of the first optical system G1 and the center axis C2 of the second optical system G2, respectively, as viewed from the object side. Likewise, as shown typically in FIG. 4B, it is preferable that light beams Lo15$_1$, Lo15$_2$ from a 15-mm object point transmit through the first planar portions $3a_1$, $3b_1$ of the variable optical element 3 in the second state where the first planar portions $3a_1$, $3b_1$ is aligned with and superposed on the center axis C1 of the first optical system G1 and the center axis C2 of the second optical system G2, respectively, as viewed from the object side. Further, as shown in FIG. 4C, it is preferable that light beams Lo50$_1$, Lo50$_2$ from a 50-mm object point transmit through the second planar portions $3a_2$, $3b_2$ in the third state where the second planar portions $3a_2$, $3b_2$ of the variable optical element 3 are aligned with and superposed on the center axis C1 of the first optical system G1 and the center axis C2 of the second optical system G2, respectively, as viewed from the object side.

In the example shown in FIGS. 4A, 4B and 4C, while the variable optical element 3 is rotated 60° with the axis of rotation CR as center upon changing from the first to the second state and changing from the second to the third state or vice versa for the sake of an easy understanding, it is here to be noted that for rapid state changing, the passage holes $3a_{11}$, $3b_{11}$, first planar portions $3a_1$, $3b_1$ and second planar portions $3a_2$, $3b_2$ may be positioned at smaller angles.

FIGS. 5A and 5B show another example of the variable optical element 3 as viewed from the center axis of rotation CR. Specifically, FIG. 5A is illustrative of a first state of another example of the variable optical element 3 and FIG. 5B is illustrative of a second state of another example of the variable optical element 3.

In the example shown in FIGS. 5A and 5B, the center axis CR of the variable optical element 3 is decentered off from halfway between the first center axis C1 of the first optical system G1 and the second center axis C2 of the second optical system G2.

As shown typically in FIG. 5A, it is preferable that light beams $Lo15_1$, $Lo15_2$ from a 15-mm object point transmit through the first planar portions $3a_1$, $3b_1$ of the variable optical element 3 in the first state where the first planar portions $3a_1$, $3b_1$ of the variable optical element 3 are aligned with and superposed on the center axis C1 of the first optical system G1 and the center axis C2 of the second optical system, respectively, as viewed from the object side. As shown typically in FIG. 5B, it is also preferable that light beams $Lo50_1$, $Lo50_2$ from a 50-mm object point transmit through the second planar portions $3a_2$, $3b_2$ of the variable optical element 3 in the second state where the second planar portions $3a_2$, $3b_2$ of the variable optical element 3 are aligned with and superposed on the center axis C1 of the first optical system G1 and the center axis C2 of the second optical system, respectively, as viewed from the object side.

It is here to be noted that surface portions other than the first 3a and the second surface portion 3b may also be used as a third surface portion 3c equal in construction and arrangement to the first 3a and the second surface portion 3b.

FIGS. 6A, and 6B show yet another example of the variable optical element 3 as viewed from the center axis of rotation CR. Specifically, FIG. 6A is illustrative of a first state of yet another example of the variable optical element 3 and FIG. 6B is illustrative of a second state of another example of the variable optical element 3.

The variable optical element 3 may consist only of a first surface portion 3a comprising a set of planar portions: a first planar portion $3a_1$ and a second planar portion $3a_2$.

As shown typically in FIG. 6A, it is preferable that a light beam Lo15 from a 15-mm object point transmits through the first planar portion $3a_1$ of the variable optical element 3 in a first state where it is aligned with and superposed on the center axis C1 of the first optical system G1 as viewed from the object side, and that a light beam Lo50 from a 50-mm object point transmits through the second planar portion $3a_2$ of the variable optical element 3 in the first state where it is aligned with and superposed on the center axis C2 of the second optical system G2 as viewed from the object side.

As shown typically in FIG. 6B, it is preferable that a light beam Lo50 from a 50-mm object point transmits through the second planar portion $3a_2$ of the variable optical element 3 in a second state where it is aligned with and superposed on the center axis C1 of the first optical system G1 as viewed from the object side, and that a light beam Lo15 from a 15-mm object point transmits through the first planar portion $3a_1$ of the variable optical element 3 in the second state where it is aligned with and superposed on the center axis C2 of the second optical system G2 as viewed from the object side.

In the stereoscopic imaging optical system assembly 1, the variable optical element 3 is rotated 180° with the center axis of rotation as center to implement fast capturing of focused images in different positions of the first G1 and the second optical system G2. Then, the images may be cut out of an area of a screen having a higher frequency and synthesized for electronic synthesis of images having a large depth of focus.

Figure 7:
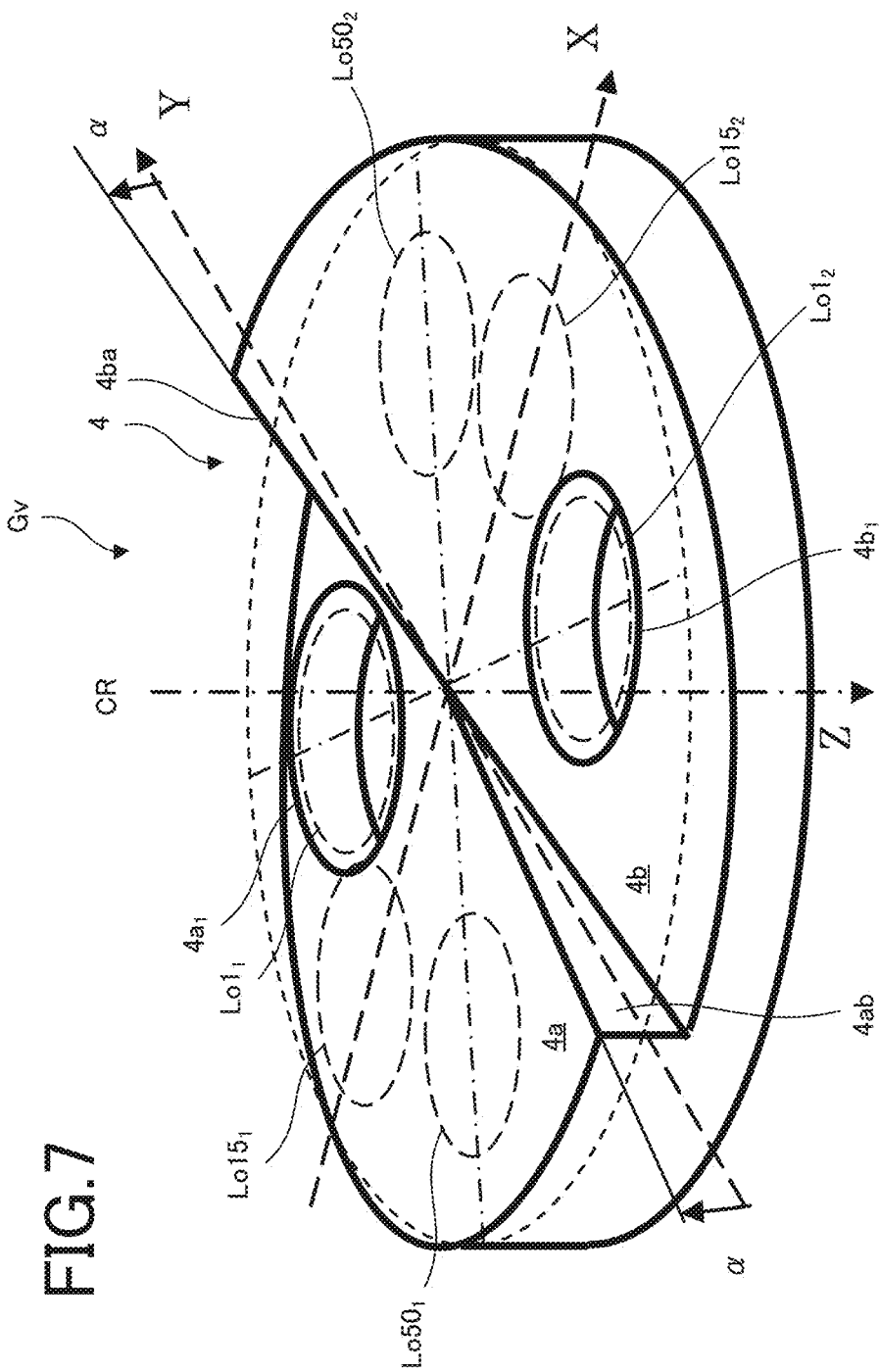
FIG. 7 is illustrative of one example of the variable optical element 4 including a tilting surface.

FIG. 7 is illustrative of one example of the variable optical element 4 having a tilting surface.

The variable optical system $G_V$ according to the embodiment here preferably includes the variable optical element 4. The variable optical element 4 includes a first surface portion 4a and a second surface portion 4b. Each of the first 4a and the second surface portion 4b preferably comprises at least one tilting surface that tilts at a given angle of tilt. In the example shown in FIG. 7, a first 4ab and a second boundary step 4ba are formed at a boundary between the first 4a and the second surface portion 4b.

Preferably, the variable optical element 4 has a tilting surface on the image plane side. Provision of the tilting surface on the image plane side enables movement of the image point to be minimized.

The first 4a and the second surface portion 4b are provided with passage holes $4a_1$ and $4b_1$, respectively, through which light beams $Lo1_1$, $Lo1_2$ from a 1-mm object point pass. And light beams $Lo15_1$, $Lo15_2$ from a 15-mm object point and light beams $Lo50_1$, $Lo50_2$ from a 50-mm object point transmit through the first 4a and the second surface portion 4b in different positions.

Each of the first 4a and the second surface portion 4b includes at least one tilting surface that tilts at a given angle of inclination. Therefore, as the variable optical element 4 rotates, it causes the optical path length to change continuously so that an appropriate angle of rotation can be determined depending on the object point distance for focusing.

It is here to be understood that when the variable optical element 4 rotates with the center axis of rotation CR as center, the perpendiculars of the first 4a and the second surface portion 4b change two-dimensionally in association with rotation of the variable optical element 4. For this reason, light beams passing through the optical element 4 are refracted, resulting in two-dimensional movement of the image center. For correction of such movement, therefore, positions of reading images out of the imaging element are preferably varied. The variable optical system $G_V$ is preferably located near the image plane to minimize movement of the image center.

Figure 8:
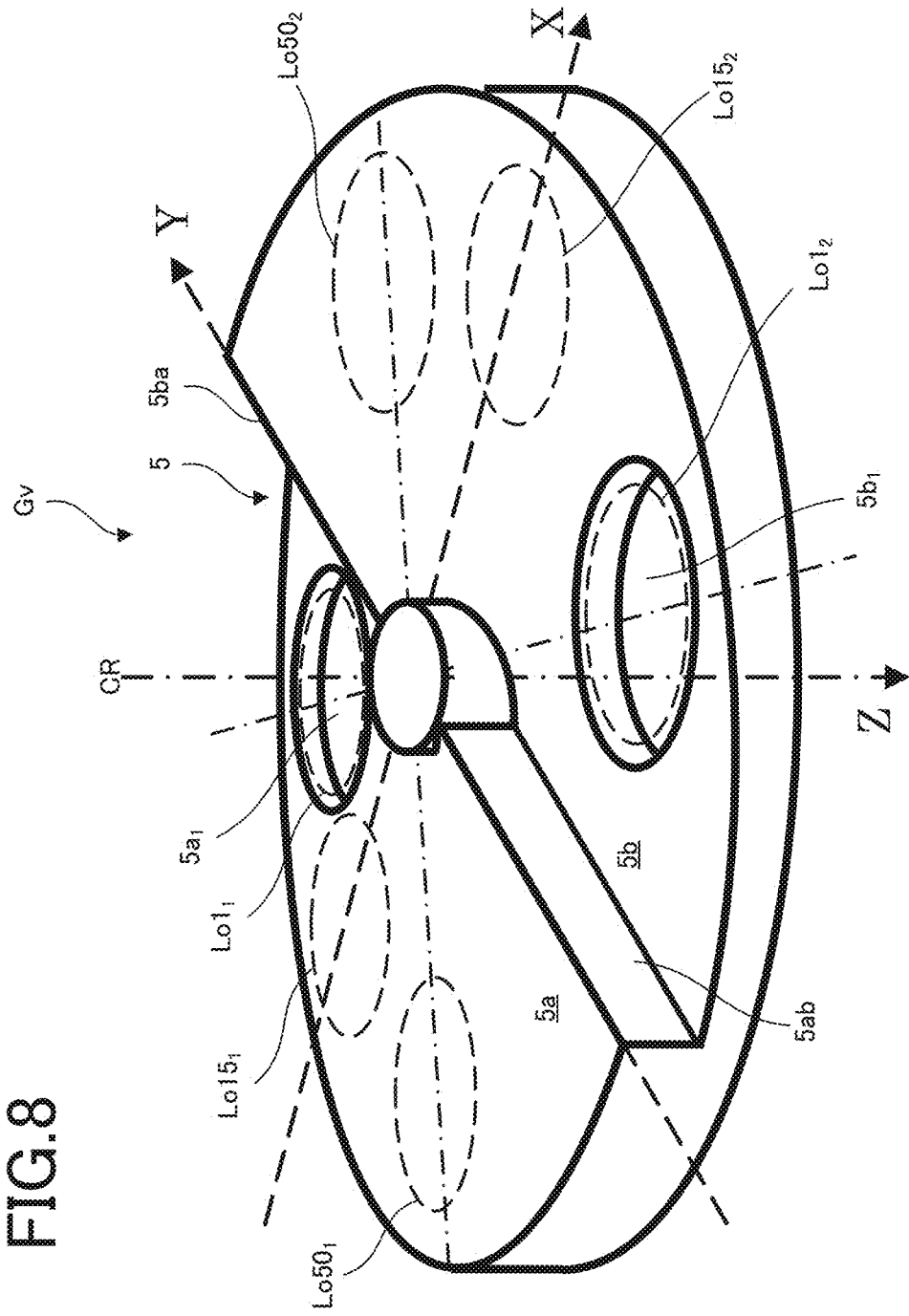
FIG. 8 is illustrative of one example of the variable optical element 5 including a helicoidal surface.

FIG. 8 is illustrative of one example of the variable optical element 5 having a helicoidal surface.

Preferably, the variable optical system $G_V$ comprises the variable optical element 5. The variable optical element 5 includes a first 5a and a second surface portion 5b. Preferably, each of the first 5a and the second surface portion 5b comprises at least one helicoidal surface that tilts in the peripheral direction of a circle with the center axis of rotation CR as center. In the example shown in FIG. 8, each of the first 5a and the second surface portion 5b comprises a continuous helicoidal surface, and a first 5ab and a second boundary step 5ba are formed at a boundary between the first 5a and the second surface portion 5b.

The first 5a and the second surface portion 5b are provided with passage holes $5a_1$ and $5b_1$ through which light beams $Lo1_1$ and $Lo1_2$ from a 1-mm object point pass. And light beams $Lo15_1$, $Lo15_2$ from a 15-mm object point and light beams $Lo50_1$, $Lo50_2$ from a 50-mm object point transmit through the first 5a and the second surface portion 5b in different positions.

The helicoidal surface of the variable optical element 5 shown in FIG. 8 comprises an ordinary one wherein a line segment rotating and advancing from the center is always orthogonal to the center axis CR so that its angle with the center axis CR is kept invariably vertical. For this reason, as the variable optical element 5 rotates, angles of two chief rays passing on the first center axis C1 of the first optical system G1 and the second center axis C2 of the second optical system G2 with the transmission surface of the variable optical element 5 are always kept invariably constant.

The first 5a, and the second surface portion 5b comprises at least one helicoidal surface that tilts in the peripheral direction of a circle with the center axis of rotation CR as center. Therefore, while the variable optical element 5 rotates, the optical path length changes continuously to determine an appropriate angle of rotation depending on the object point distance for focusing.

For such helicoidal configuration, it is preferable to preset the imaging area because even when the variable optical element 5 rotates with the center axis of rotation CR as center, there is no change in the perpendiculars of the helicoidal surfaces.

Figure 9:
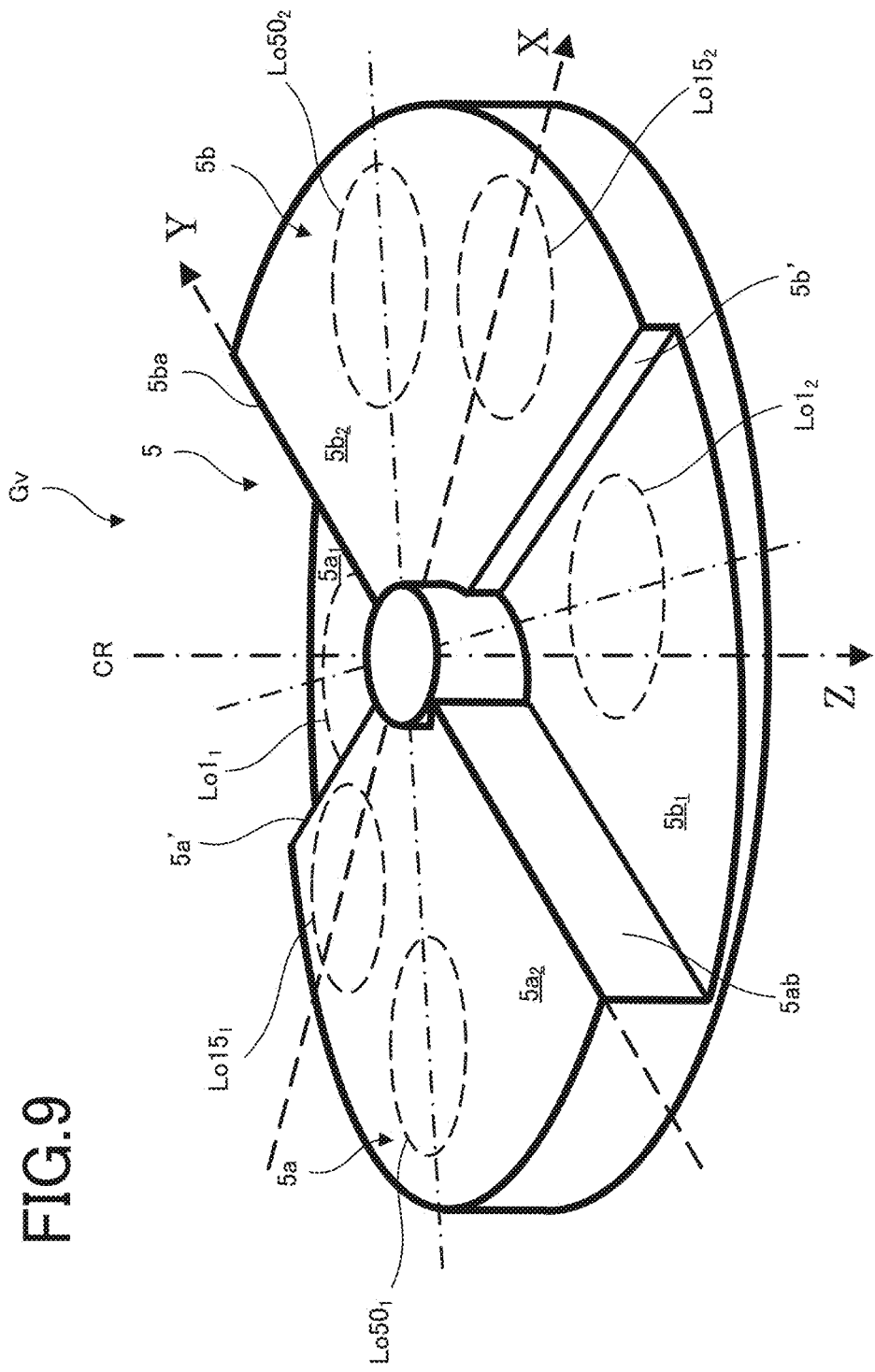
FIG. 9 shows one example of the variable optical element 5 wherein the first surface portion 5a includes a step 5a' and the second surface portion 5b includes a step 5b'.

FIG. 9 is illustrative of one example of the variable optical element 5 in which a first 5a and a second surface portion 5b include steps 5a' and 5b', respectively.

In the example shown in FIG. 9, a first 5ab and a second boundary step 5ba are formed at a boundary between the first 5a and the second surface portion 5b, and a first 5a' and a second changeover step 5b' are formed between first $5a_1$, $5b_1$ and second helicoidal surface portions $5a_2$, $5b_2$, respectively.

Light beams $Lo1_1$, $Lo1_2$ from a 1-mm object point transmit through the first helicoidal surfaces $5a_1$, $5b_1$, and light beams $Lo15_1$, $Lo15_2$ from a 15-mm object point and light beams $Lo50_1$, $Lo50_2$ from a 50-mm object point transmit through the second helicoidal surfaces $5a_2$, $5b_2$.

In the variable optical element 5 shown in FIG. 9, the helicoidal surfaces are used even for the light beams $Lo1_1$, $Lo1_2$ from the 1-mm object point. Therefore, the image point is less movable in the XY direction as compared with the light beams $Lo15_1$, $Lo15_2$ from the 15-mm object point and the light beams $Lo50_1$, $Lo50_2$ from the 50-mm object point.

In the variable optical element 5 shown in FIG. 9, the first 5a and the second surface portion 5b at least include the first $5a_1$, $5b_1$ and the second helicoidal surface portions $5a_2$, $5b_2$, respectively. Therefore, as the variable optical element 5 rotates, it causes one optical path length to be changed over to another or the optical path length to change continuously to determine an appropriate angle of rotation depending on the object point distance for focusing.

For such helicoidal configuration, it is preferable to preset the imaging area because even when the variable optical element 5 rotates with the center axis of rotation CR as center, there is no change in the perpendiculars of the helicoidal surfaces.

Figure 10:
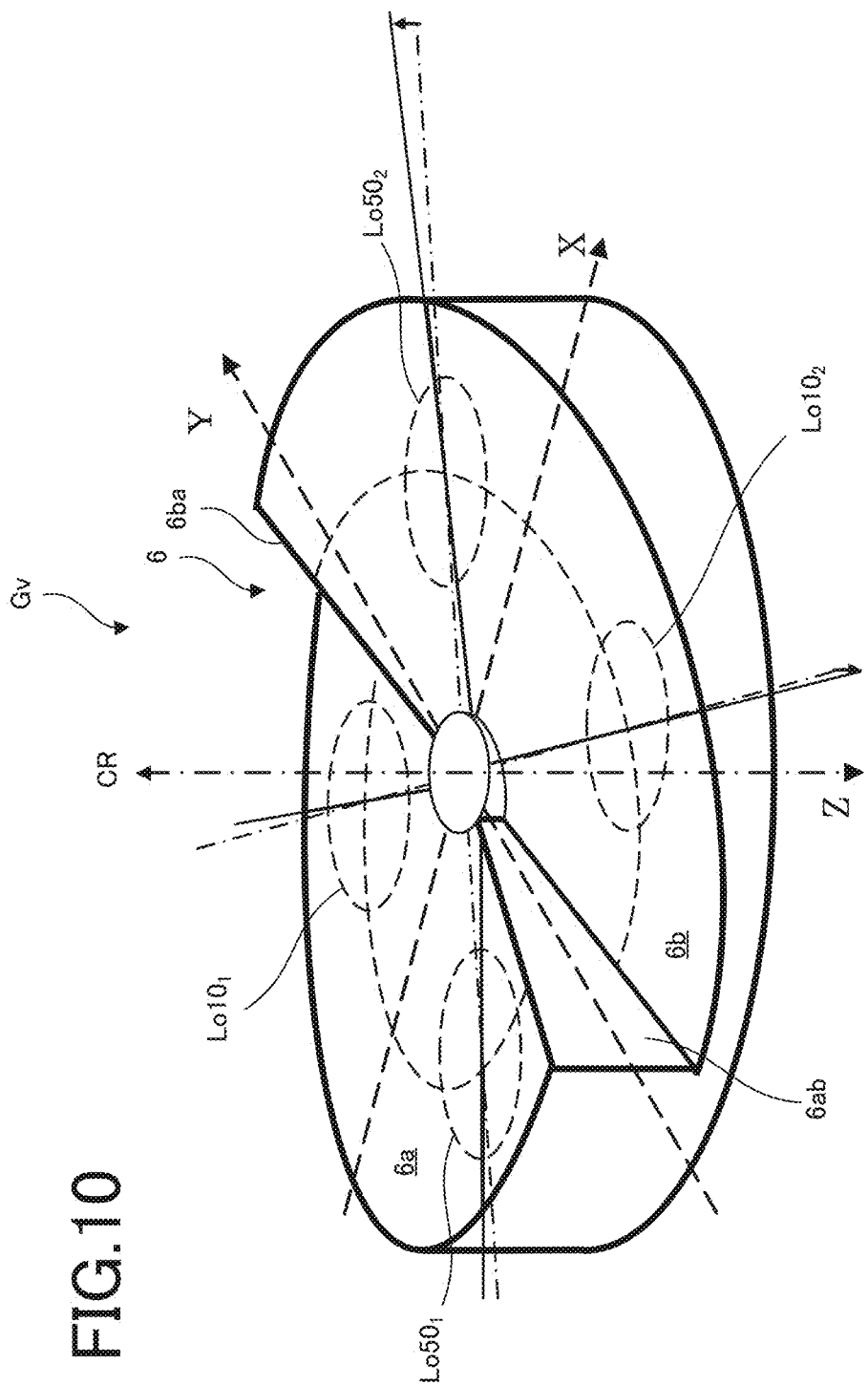
FIG. 10 is illustrative of one example of the variable optical element 6 having a radially tilting surface 6.

FIG. 10 is illustrative of one example of the variable optical element 6 having a radially tilting surface.

Preferably, the variable optical system $G_V$ includes the variable optical element 6. The variable optical element 6 includes a first 6a and a second surface portion 6b. Preferably, the first 6a, and the second surface portion 6b comprises at least one tilting surface wherein the radial direction angle with respect to the center axis of rotation CR changes in the peripheral direction of a circle with the center axis of rotation CR as center. In the example shown in FIG. 10, the first 6a and the second surface portion 6b comprise continuous tilting surfaces in the radial direction, and a first 6ab and a second boundary step 6ba are formed at a boundary between the first 6a and the second surface portion 6b.

Light beams $Lo10_1$, $Lo10_2$ from a 10-mm object point and light beams $Lo50_1$, $Lo50_2$ from a 50-mm object point transmit through the first 6a and the second surface portion 6b in different positions.

The first 6a, and the second surface portion 6b comprises at least one radially tilting surface wherein the radial direction angle with respect to the center axis of rotation CR changes in the peripheral direction of a circle with the center axis of rotation CR as center. By rotation of the variable optical element 6, it is therefore possible to continuously change the tilt of the tiling surface in the radial direction. In this case, only vergence may be varied with no change in the length of the transmission optical path.

More preferably, the helicoidal surface shown in FIG. 8 is combined with the radially tilting surface shown in FIG. 10 to determine an appropriate angle of rotation depending on the object point distance for simultaneous combination of focus and vergence so that the object center can always be located at the center of the imaging plane.

Figure 11:
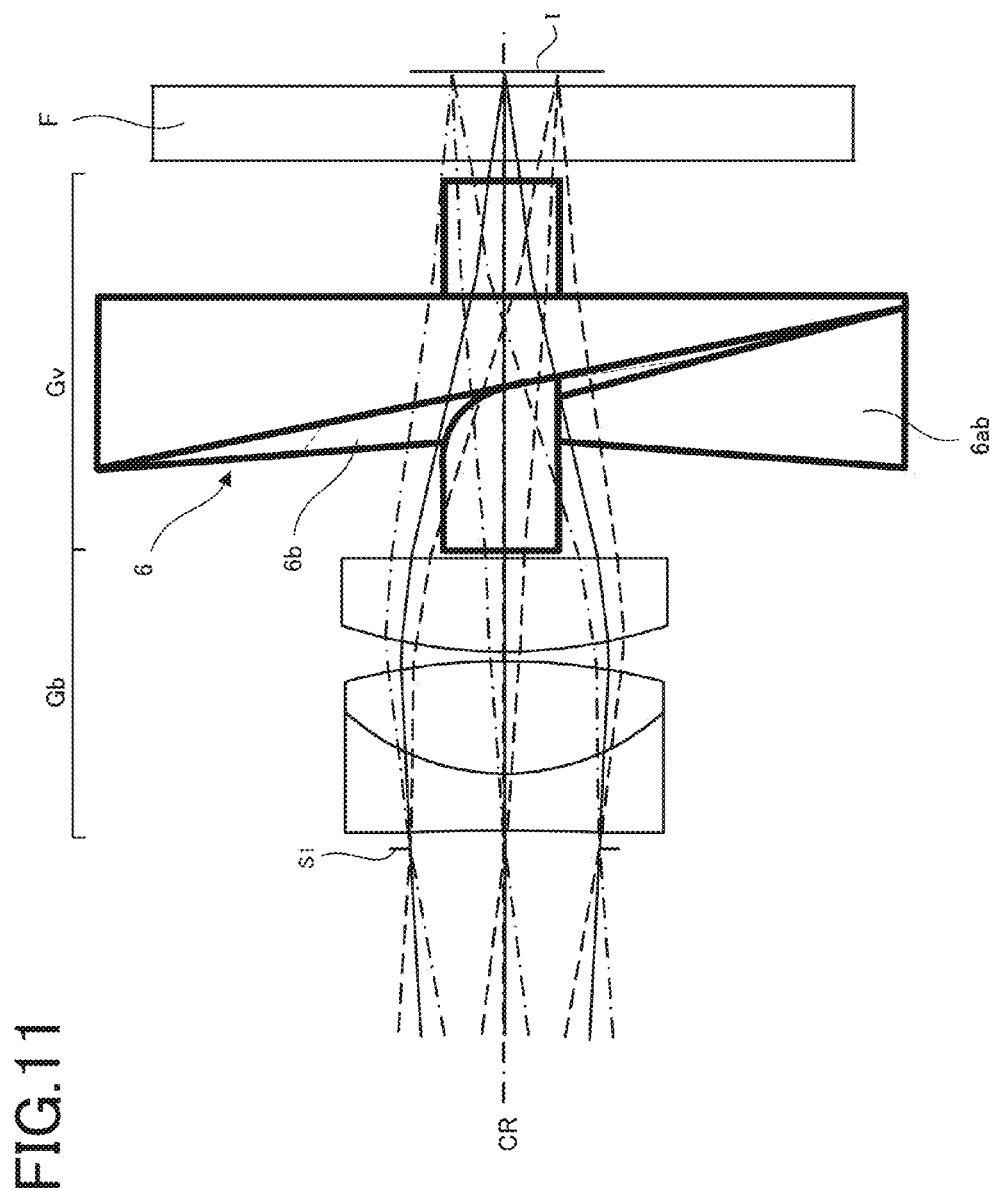
FIG. 11 is illustrative of the variable optical element 6 shown in FIG. 10, as viewed from the X-axis direction.
Figure 12:
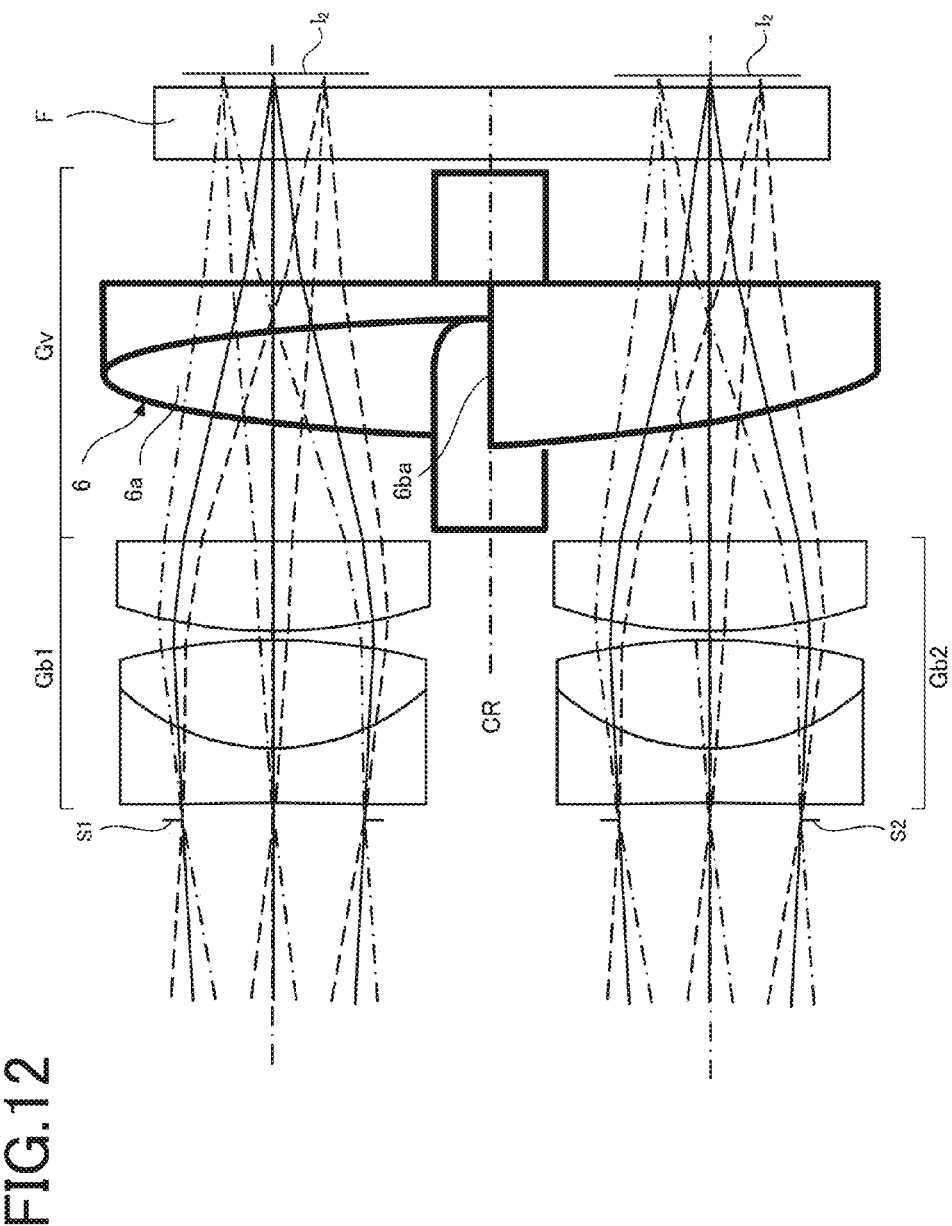
FIG. 12 is illustrative of the variable optical element 6 shown in FIG. 10, as viewed from the Y-axis direction.
Figure 13:
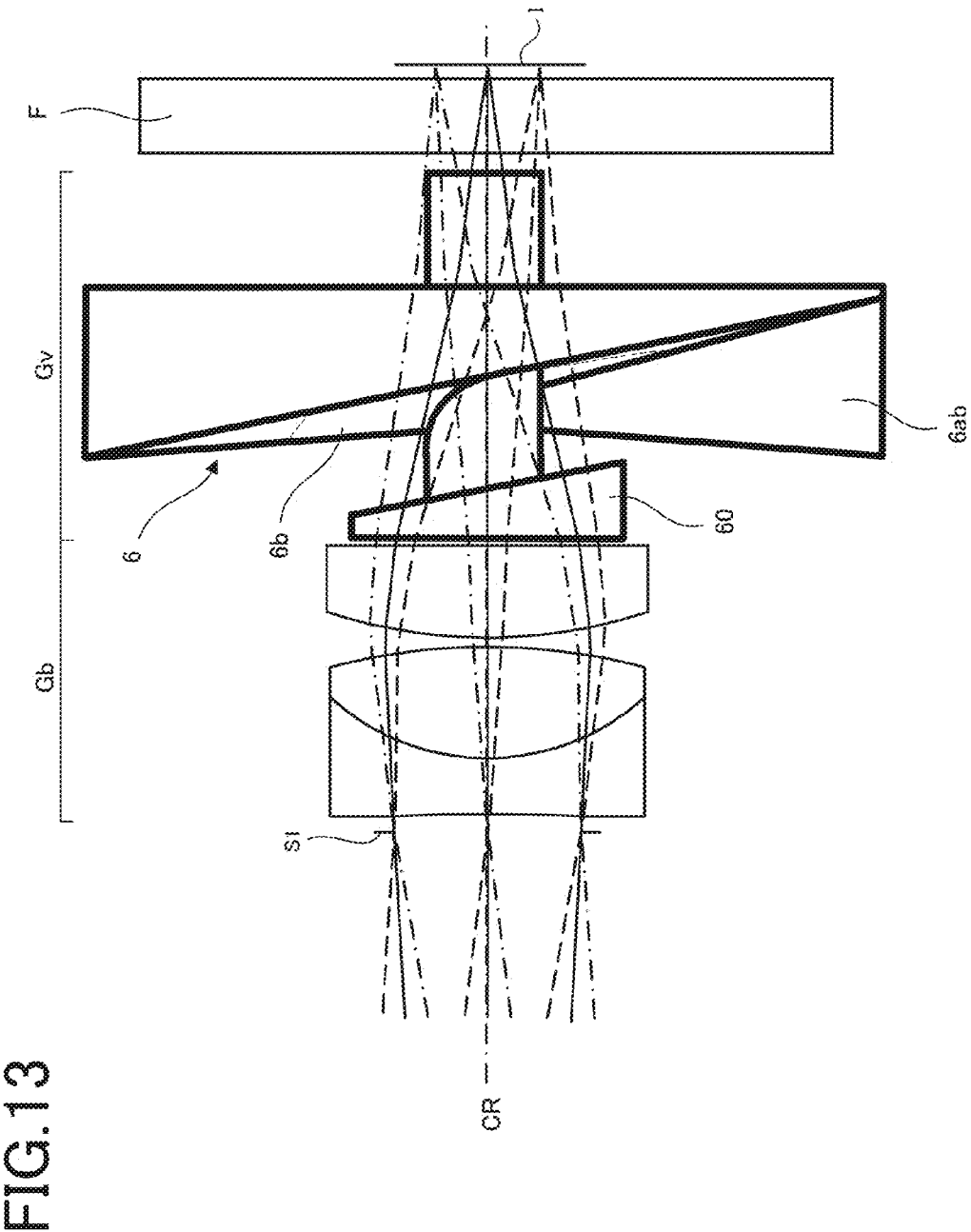
FIG. 13 is illustrative of the variable optical system $G_V$ using the correction optical element 60.

FIG. 11 is illustrative of the variable optical element 6 shown in FIG. 10, as viewed from the X-axis direction. FIG. 12 is illustrative of the variable optical element 6 shown in FIG. 10, as viewed from the Y-axis direction. FIG. 13 is illustrative of the variable optical system $G_V$ using a correction optical element 60.

Such variable optical element 6 as depicted in FIG. 11 or FIG. 12 has a tilting or helicoidal surface that may sometimes give rise to a bending of the left and right optical axes. For this reason, it is preferable to use a wedged correction optical element 60. With the wedged correction optical element 60, it is thus possible to make correction for a shifting of the image center on the left and right optical axes, which may be caused by the tilting or helicoidal surface.

Figure 14:
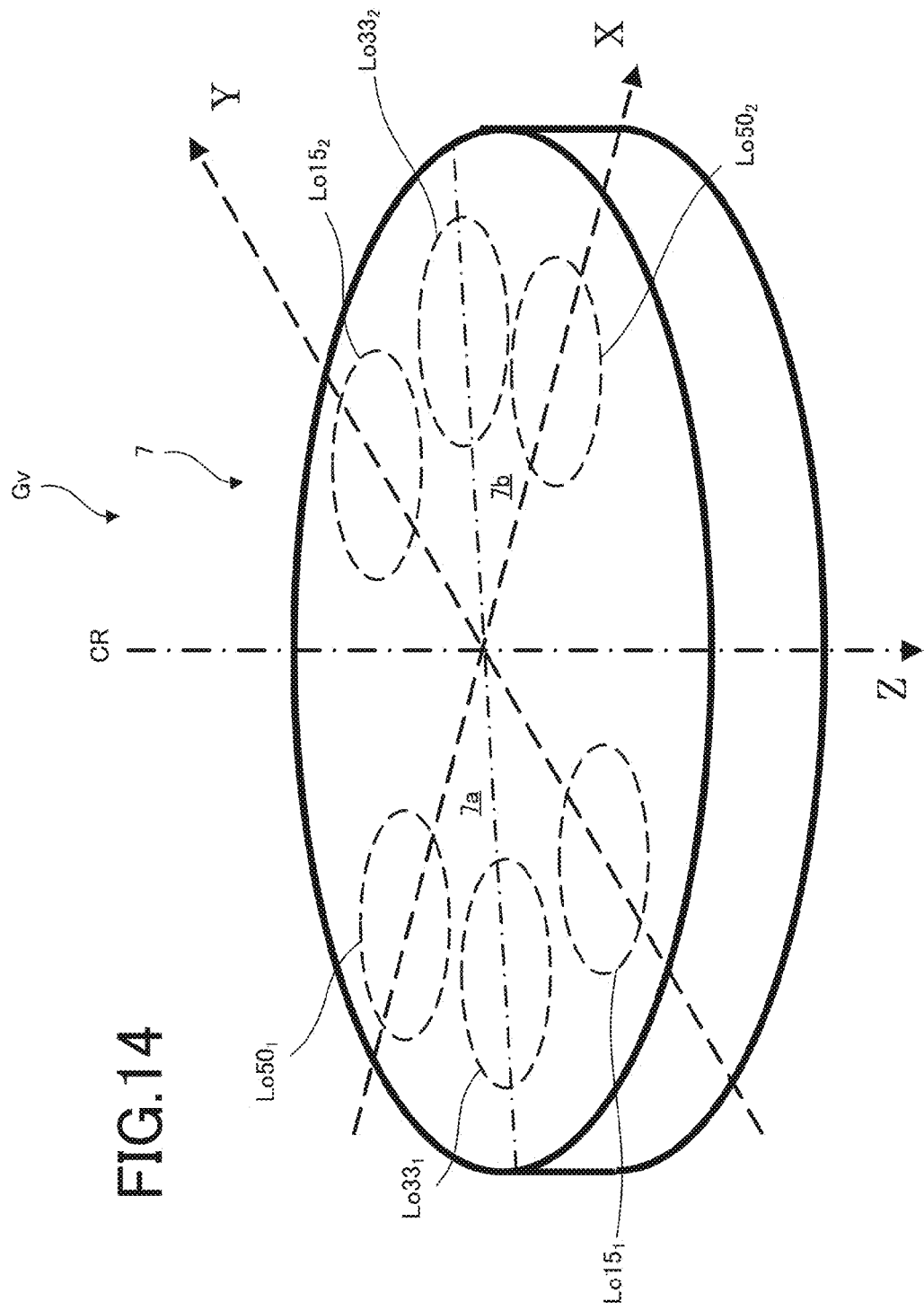
FIG. 14 is illustrative of one example of the variable optical element 7 having a free-form surface 7.

FIG. 14 is illustrative of one example of the variable optical element 7 including a free-form surface.

Preferably, the variable optical element 7 includes at least one curved surface having a varying partial curvature.

By allowing a portion of the curved surface to have a varying curvature, a light beam may selectively transmit through the optical paths taken by at least the first G1 and the second optical system G2 for focus adjustment.

It is then preferable that the curved surface is defined a free-form surface.

A surface having a shape varying from site to site is formed by the free-form surface, and designed such that at a far point, a light beam passes through a portion of the variable optical element 7 having an optically relatively weak refractive power or a negative refractive power and at a near point, a light beam passes through a portion of the variable optical element 7 having an optically relatively strong refractive power or a positive refractive power. This construction/arrangement makes it possible to adjust focus at both a far point and a near point.

Figure 15:
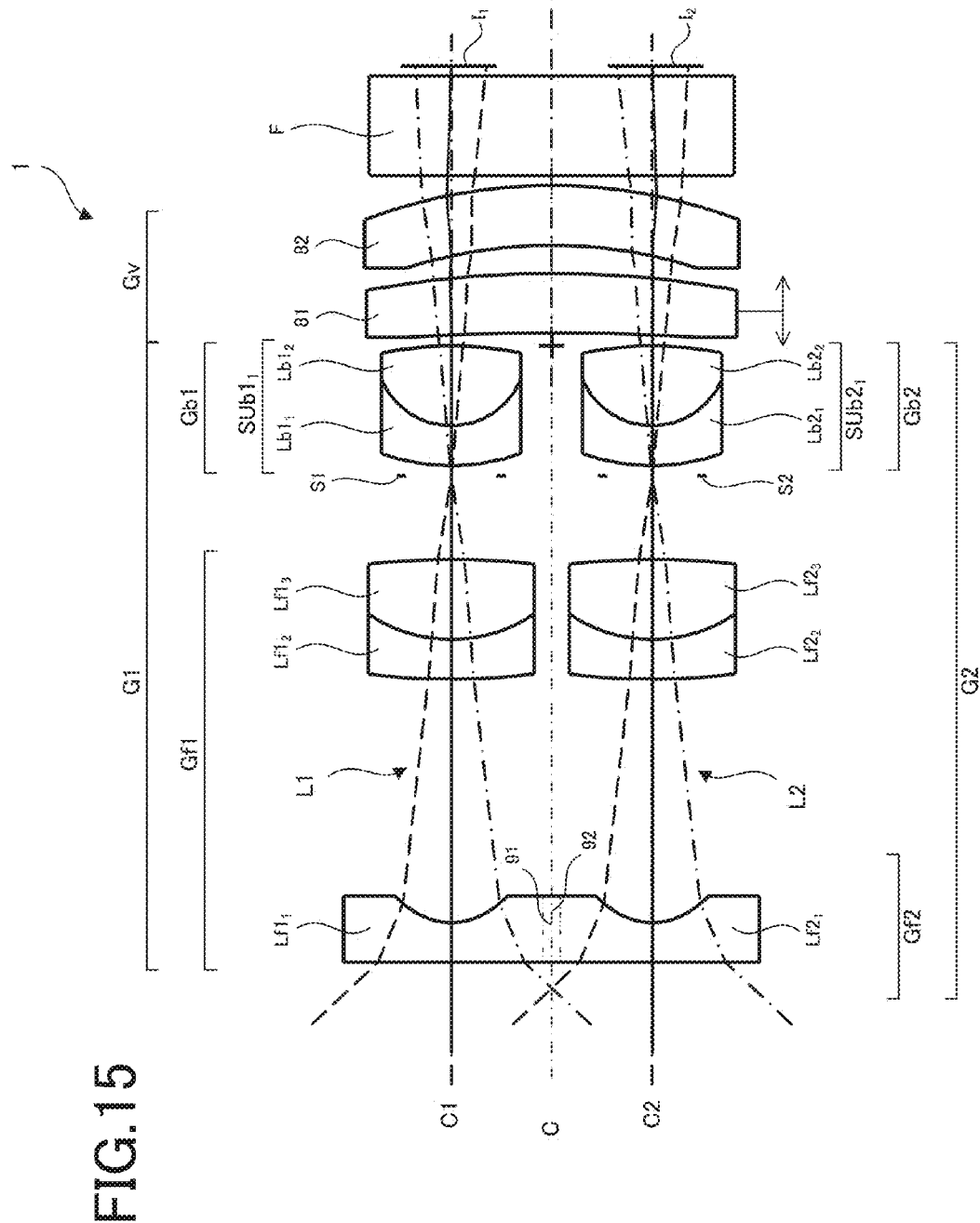
FIG. 15 is illustrative of one example of the variable optical system $G_V$ wherein at least one optical element 81 is capable of moving in the center axis direction.

FIG. 15 is illustrative of one example of the variable optical system $G_V$ including at least one optical element 8 that is movable in the center axis C direction.

Preferably, the variable optical system $G_V$ includes at least one positive or negative variable optical element 81 that is movable in the center axis C direction. As depicted in FIG. 15, the variable optical element 81 of the variable optical system $G_V$ is movable in the center axis C direction of the variable optical system $G_V$. This construction/arrangement ensures that as the object point moves, it causes the variable optical element 8 to move in the center axis C direction for focus adjustment of the first G1 and the second optical system G2.

It is preferable that the variable optical system $G_V$ is located with the center axis C of the optical system assembly halfway between the first C1 and the second center axis C2 and comprises two lenses: a positive lens 81 and a negative lens 82 that are rotationally symmetric with respect to the center axis C of the optical system assembly wherein at least one lens 81 of the two positive and negative lenses 81 and 82 is the variable optical element 81 that is movable in the center axis C direction of the optical system assembly.

Especially when the object point moving distance is long, it is required to move the variable optical element 81 having strong power; however, as an optical element having strong power is typically located near an image plane, it causes strong field curvature to occur. In a decentered optical system such as one intended herein, different field curvatures occur at left and right optical paths, resulting in very poor resolution. To avoid this, it is important to move either one of the positive and negative optical elements located in place thereby canceling out the field curvatures.

Preferably, the spacing or separation between the first C1 and the second center axis C2 should be not greater than 10 mm.

An ordinary stereoscopic imaging optical system has an entrance pupil separation of about 50 mm in order to obtain a three-dimensional appearance quite normally. A microscope has an entrance pupil separation of about 20 mm, and zooming or focusing is implemented using a complicated linkage mechanism or the like. A hard endoscope includes an imaging unit coming out from within the body so that a focusing mechanism or the like is easily mounted to that imaging unit.

By contrast, a stereoscopic imaging optical system used with an endoscope includes an imaging unit that is also inserted through the body cavity; so it is preferable to use an entrance pupil of simple structure that is not greater than 10 mm. It is therefore preferable to implement focusing and vergence for both eyes in a single operation by a single element.

As shown in FIG. 15, a planoconcave negative lens $Lf1_1$ in the first front group Gf1 may be provided with a first notch 91 that is obtained by cutting out a portion of the second front group Gf2 side, and a planoconcave negative lens $Lf2_1$ in the second front group Gf2 may be provided with a second notch 92 that is obtained by cutting out a portion of the first front group Gf1 side.

Preferably, the first notch 91 is in abutment on the second notch 92. By abutment of the first notch 91 on the second notch 92, it is possible to make short the distance between the first optical axis C1 of the first front group Gf1 and the second optical axis C2 of the second front group Gf2 thereby making the stereoscopic imaging optical system assembly 1 compact.

It is here to be noted that such notches may be provided in the corresponding lenses in the first Gf1 and the second front group Gf2 for abutment on each other.

A light-shielding member (not shown) may also be interposed between the first and second notches 91 and 92. As the light-shielding member is provided, flare light is less likely to enter between the first front group Gf1 and the second front group Gf2 even when the base length gets short.

The planoconcave negative lenses $Lf1_1$ and $Lf2_1$ may be integrally molded.

The object-side angle of view is preferably greater than 60°.

When the angle of view for observation is wide, adjustment of focus and inward angle on the object side gives rise to rotationally asymmetric image distortion. In the embodiment described here, the variable optical system $G_V$ is so located on the image plane side that the angle of view for observation can be wide.

The exemplary construction/arrangement of the variable optical system shown in FIGS. 4-6 may be applied to the variable optical elements 4, 5, 6 and 7 comprising not just a plane but also a tilting surface, a helicoidal surface, a radially tilting surface, and a free-form surface. The center axis of the variable optical system $G_V$ may be departing from halfway between the center axes of the first and second optical systems G1 and G2. Each of the surfaces of the variable optical element 4, 5, 6, 7 may be formed of a single first surface portion.

In addition, the variable optical system $G_V$ may comprise a combined construction/arrangement of the embodiments described herein. For instance, different surfaces may be applied to the object-side surface and image plane-side surface.

Figure 16:
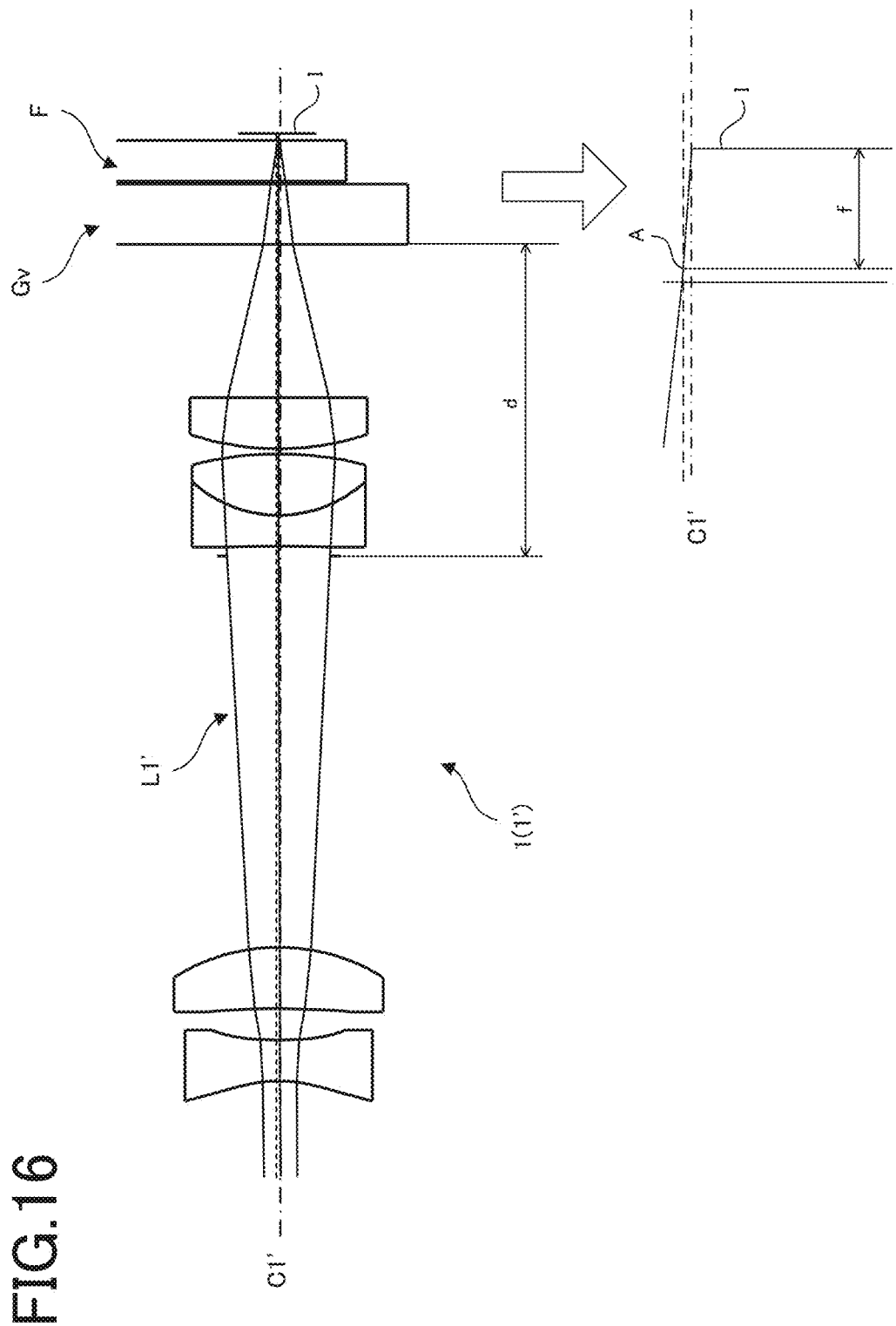
FIG. 16 is illustrative of the focal length f of the stereoscopic imaging optical system assembly 1 according to one embodiment of the invention.

FIG. 16 is indicative of the focal length f of the stereoscopic imaging optical system assembly 1 according to one embodiment of the invention.

The stereoscopic imaging apparatus according to the embodiment described here should preferably satisfy the following condition (1).

$$d/f<0.5 \tag{1}$$

where d is a distance between the variable optical system $G_V$ and the aperture S, and f is the focal length of the optical system assembly.

In the embodiment described here, the focal length of the stereoscopic imaging optical system assembly 1 is indicated by f. When the stereoscopic imaging optical system assembly 1 is decentered, the assembly is first cleared of decentration. A parallel beam from infinity enters an optical system 1', and an axial marginal ray L1' incident on the optical system 1' passes through the optical system 1', exiting out and reaching a position A where it is virtually bent. The focal length f of the stereoscopic imaging optical system assembly 1 is defined by a distance from that position A to an image plane I.

As the upper limit to Condition (1) is exceeded, the variable optical system $G_V$ is away from the aperture S. Upon transformation of focus and vergence, aberrations around the perimeter of an image go extremely worse, resulting in poor resolution.

The stereoscopic imaging apparatus according to the embodiment described here should preferably satisfy the following condition (2).

$$10<fb/f \tag{2}$$

where fb is the focal length of the variable optical system $G_V$, and f is the focal length of the optical system assembly.

As the lower limit to Condition (2) is not reached, the focal length of the variable optical system $G_V$ gets too short. This in turn leads to large field curvature, resulting in inability to obtain high resolution around the perimeter of the image.

More preferably, the stereoscopic imaging apparatus should satisfy the following condition (2').

$$50<|fb/f| \tag{2'}$$

where fb is the focal length of the variable optical system $G_V$, and f is the focal length of the optical system assembly.

As the lower limit to Condition (2') is not reached, the focal length of the variable optical system $G_V$ gets too short. This in turn leads to large field curvature, resulting in inability to obtain high resolution around the perimeter of the image.

Preferably, the stereoscopic imaging apparatus should satisfy the following condition (3).

$$0.3<dv/f \tag{3}$$

where dv is the amount of movement of the variable optical system $G_V$, and f is the focal length of the optical system assembly.

As the lower limit to Condition (3) is not reached, the range of focus adjustment in association with movement of the variable optical system $G_V$ gets too narrow to hold a sufficient distance from the near point to the far point.

The stereoscopic imaging optical system assembly 1 according to the embodiment described here is now explained with specific examples whose data will be given later. In a coordinate system used in the examples, the Z-axis positive direction is defined by the direction of the center axis of rotation CR toward the image plane, and the X-axis positive direction is defined by the direction from the center axis of rotation CR toward the second center axis C2.

Figure 17:
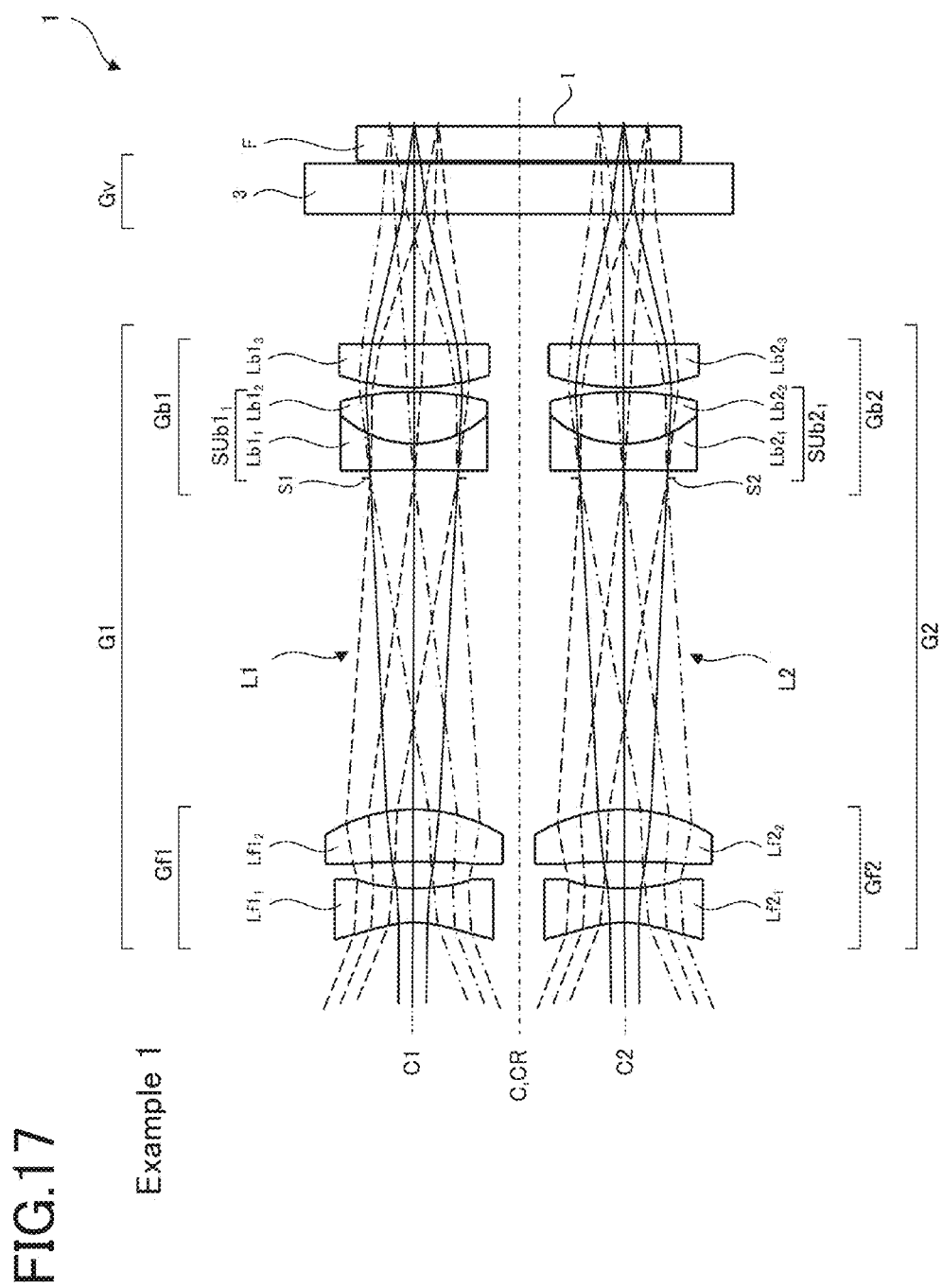
FIG. 17 is a sectional view of Example 1 of the stereoscopic imaging optical system assembly 1, as taken along its center axis C.
Figure 18:
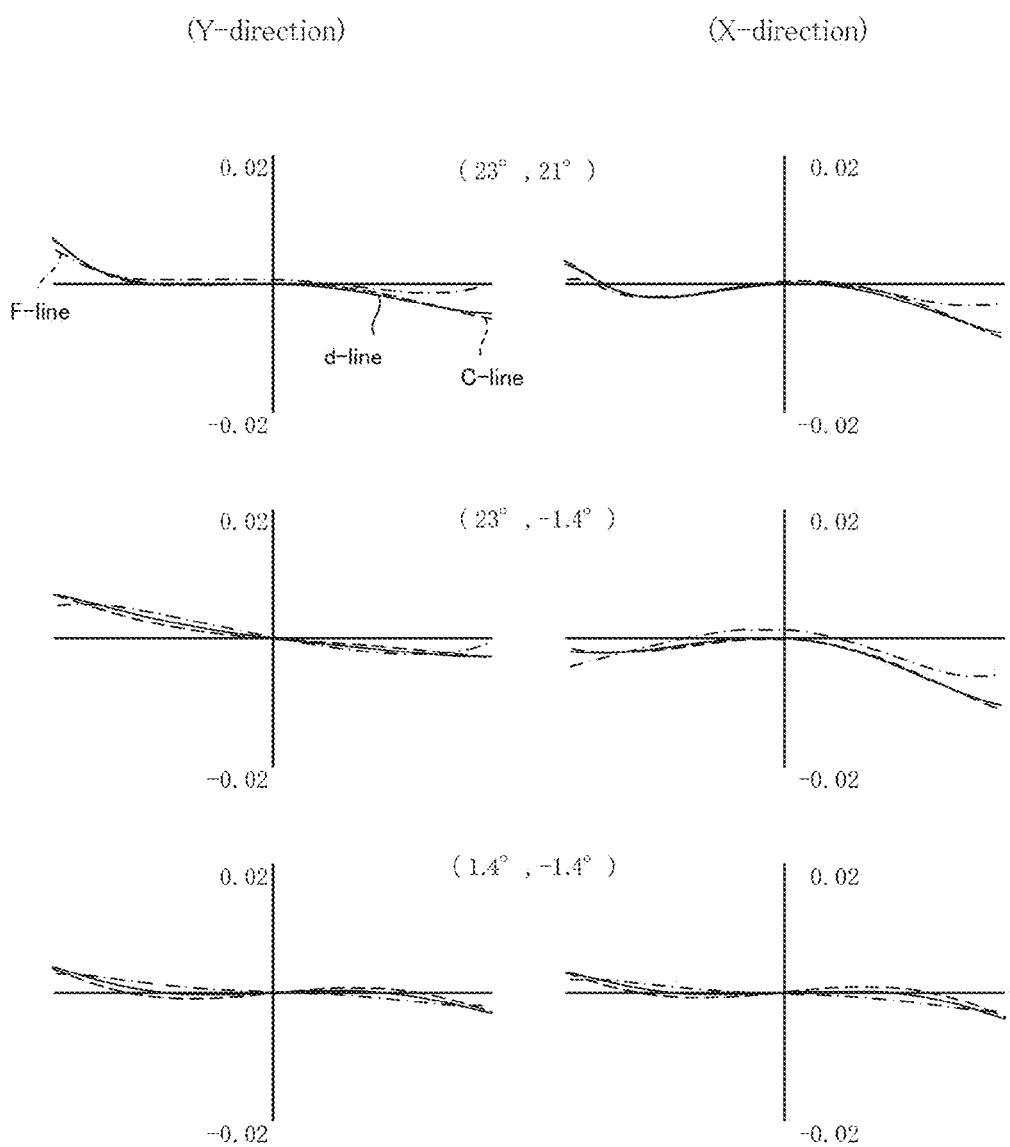
FIG. 18 is a transverse aberration diagram at a far point for Example 1 of the stereoscopic imaging optical system assembly 1.
Figure 19:
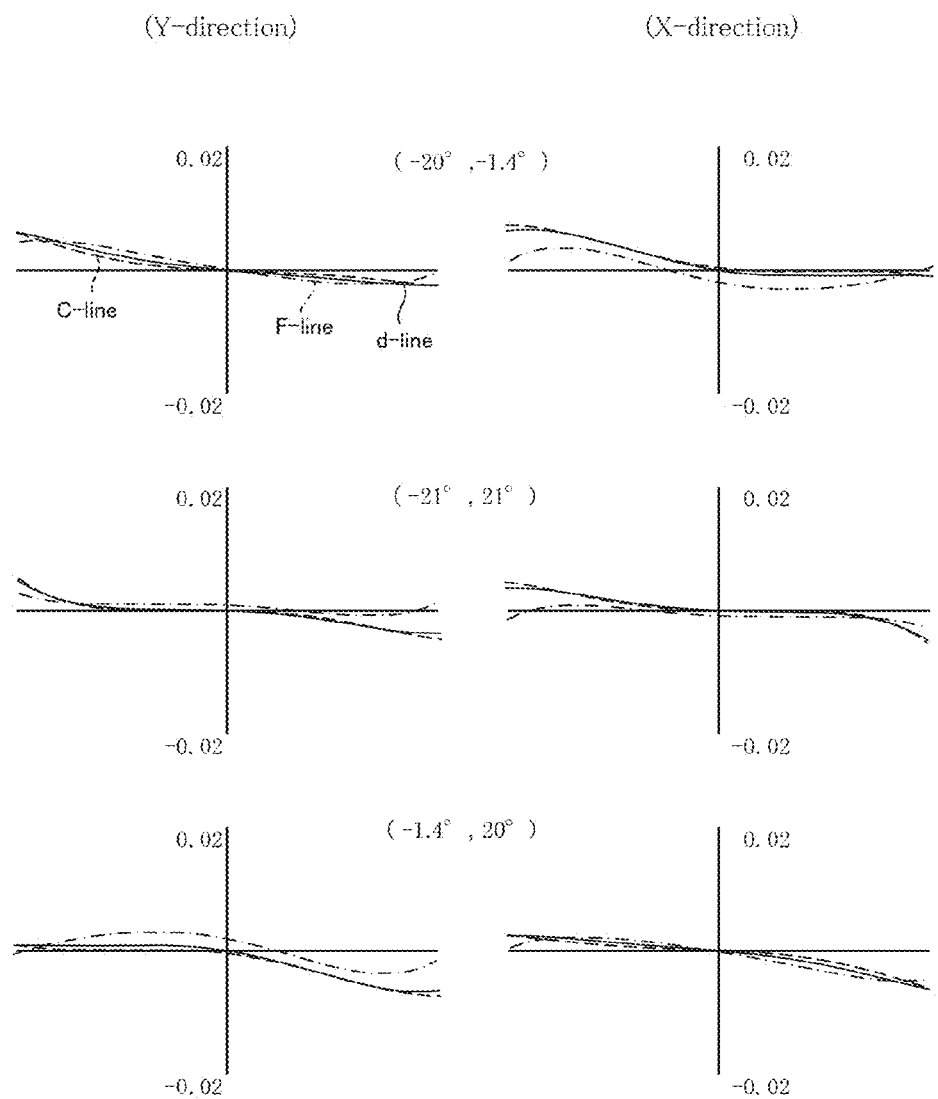
FIG. 19 is a transverse aberration diagram at a far point for Example 1 of the stereoscopic imaging optical system assembly 1.
Figure 20:
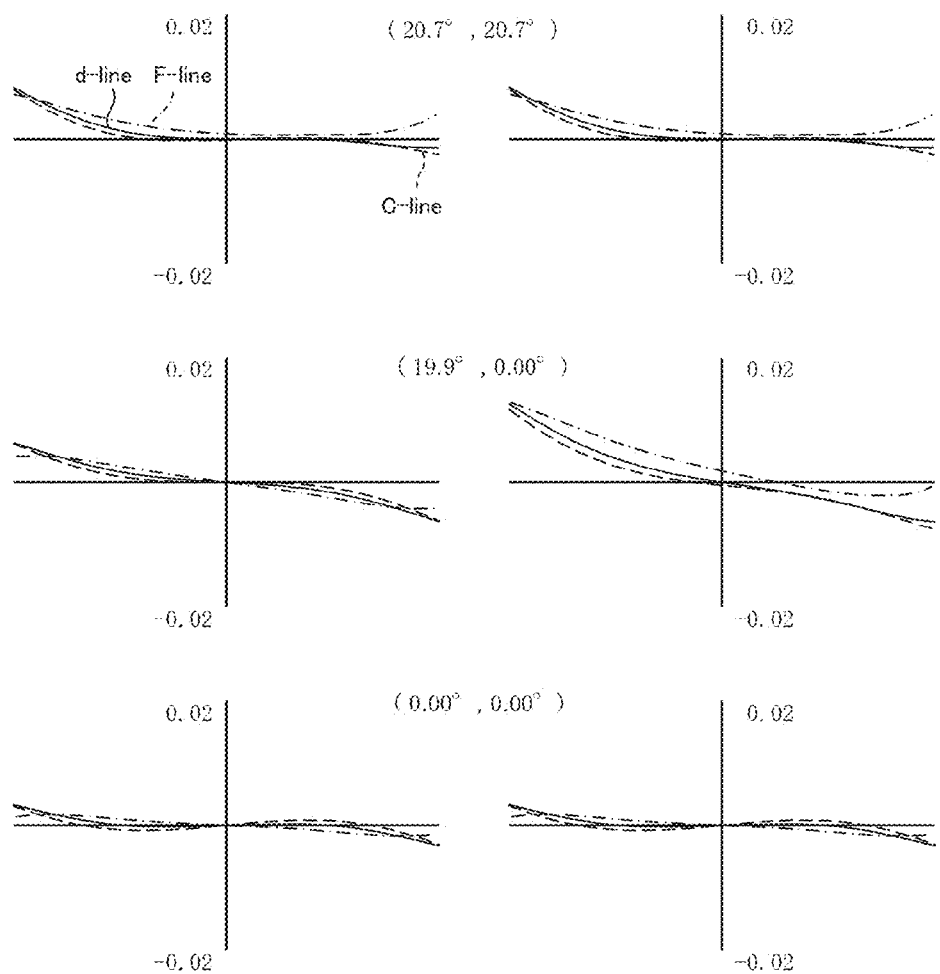
FIG. 20 is a transverse aberration diagram at a near point for Example 1 of the stereoscopic imaging optical system assembly 1.
Figure 21:
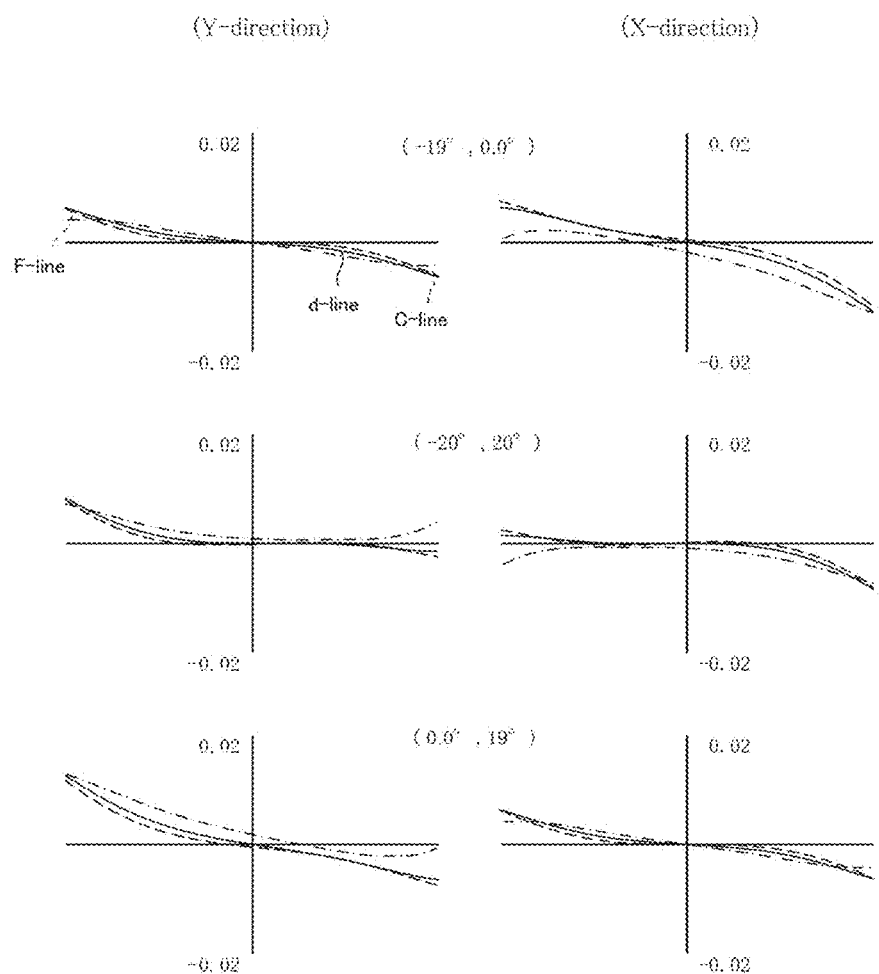
FIG. 21 is a transverse aberration diagram at a near point for Example 1 of the stereoscopic imaging optical system assembly 1.
Figure 22:
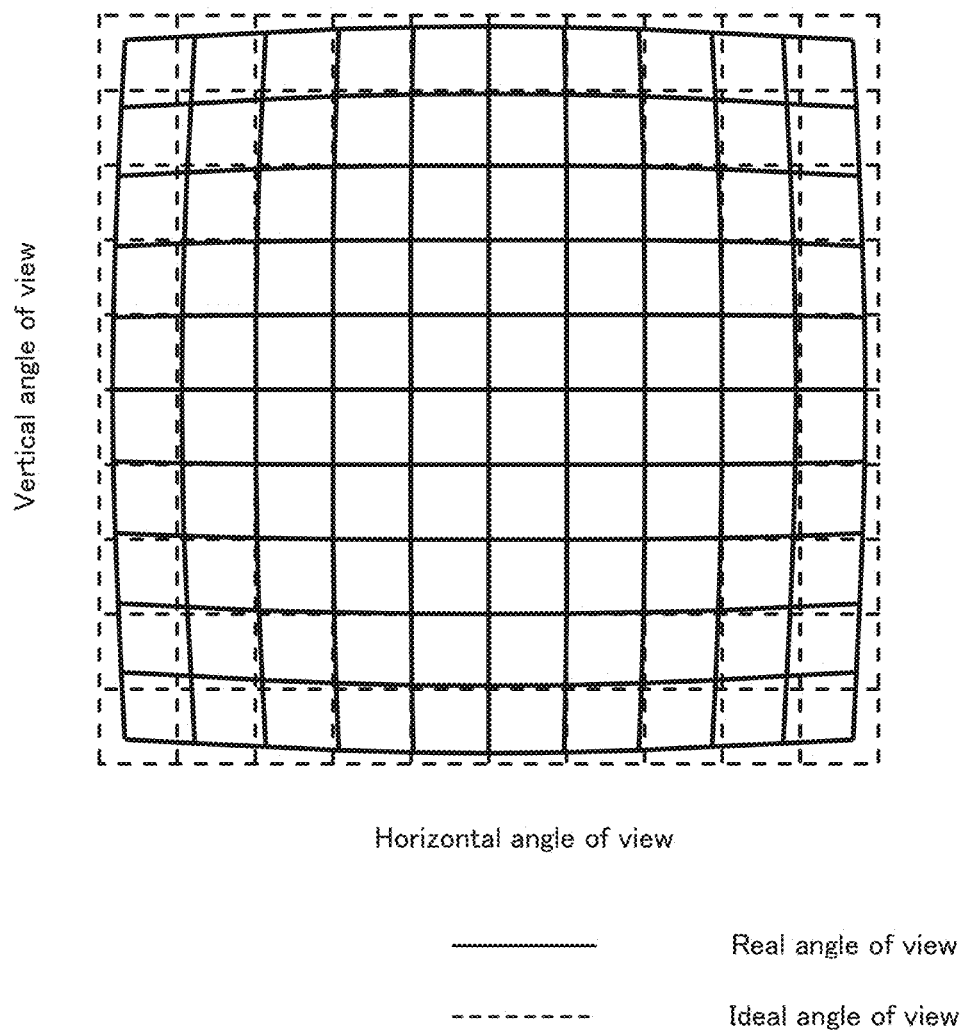
FIG. 22 is illustrative of image distortion in Example 1 of the stereoscopic imaging optical system assembly 1.

FIG. 17 is a sectional view of Example 1 of the stereoscopic imaging optical system assembly 1, as taken along the center axis C. FIGS. 18 and 19 are transverse aberration diagrams at a far point for Example 1 of the stereoscopic imaging optical system assembly 1. FIGS. 20 and 21 are transverse aberration diagrams at a near point for Example 1 of the stereoscopic imaging optical system assembly 1. FIG. 22 is indicative of image distortion in Example 1 of the stereoscopic imaging optical system assembly 1.

In the transverse aberration diagrams, the angles indicated at the center stand for the angles of view in the vertical direction, and transverse aberrations at those angles in the Y (meridional) direction and X (sagittal) direction are shown. Note here that the minus sign affixed to the angles of view means a clockwise angle with respect to the X-axis positive direction. The same will hold for the following transverse aberration diagrams.

As shown in FIG. 17, Example 1 of the stereoscopic imaging optical system assembly 1 comprises, in order from an object side to an image plane side, a first optical system G1 with a first center axis C1 as an optical axis, a second optical system G2 with a second center axis C2 parallel with the first center axis C1 as an optical axis, and a variable optical system $G_V$ having a single center axis C.

Parallel arrangement of the first G1 and the second optical system G2 makes stereoscopic observations possible.

The first optical system G1 includes, in order from the object side to the image plane side, a first front group Gf1 including a double-concave negative lens $Lf1_1$ and a positive meniscus lens $Lf1_2$ convex on the image plane side, a first aperture S1, and a first rear group Gb1 including a first rear-group cemented lens $SUb1_1$ consisting of a double-concave negative lens $Lb1_1$ and a double-convex positive lens $Lb1_2$ and a positive meniscus lens $Lb1_3$ convex on the object side.

The second optical system G2 includes, in order from the object side to the image plane side, a second front group Gf2 including a double-concave negative lens $Lf2_1$ and a positive meniscus lens $Lf2_2$ convex on the image plane side, a second aperture S2, and a second rear-group cemented lens $SUb2_1$ consisting of a double-concave negative lens $Lb2_1$ and a double-convex positive lens $Lb2_2$ and a positive meniscus lens $Lb2_3$ convex on the object side.

The variable optical system $G_V$ takes a form of the variable optical element 3 shown in FIG. 3, and is rotatable with the center axis C as the center axis of rotation CR. This optical system $G_V$ further includes passage holes $3a_{11}, 3b_{11}$ through which a light beam passes when the object point is 1 mm. The thickness of the first planes $3a_1, 3b_1$ through which a light beam passes when the object point is 15 mm is 0.679 mm, and the thickness of the second planes $3a_2, 3b_2$ through which a light beam passes when the object point is 50 mm is 0.755 mm.

There is a filter F located in front of the image plane I.

A first light beam L1 incident on the first front group Gf1 from a first object plane (not shown) passes through the double-concave negative lens $Lf1_1$, positive meniscus lens $Lf1_2$, first aperture S1, cemented lens $SUb1_1$ in the first lens group Gb1, and positive meniscus lens $Lb1_3$, leaving the first rear group Gb1, and then entering the variable optical system $G_V$.

A second light beam L2 incident on the second front group Gf2 from a second object plane (not shown) passes through the double-concave negative lens $Lf2_1$, positive meniscus lens $Lf2_2$, second aperture S2, cemented lens $SUb2_1$ in the second rear lens group Gb2, and positive meniscus lens $Lb2_2$, and exits out of the second rear group Gb2, then entering the variable optical system $G_V$.

The first L1 and the second light beam L2 incident on the variable optical element 3 forming the variable optical system $G_V$ pass through the passage holes $3a_{11}, 3b_{11}$ when the object point is 1 mm, transmit through the first planes $3a_1, 3b_1$ when the object point is 15 mm, and transmit through the second planes $3a_2, 3b_2$ when the object point is 50 mm. Then, the first L1 and the second light beam L2 enter the image plane through the filter F.

Figure 23:
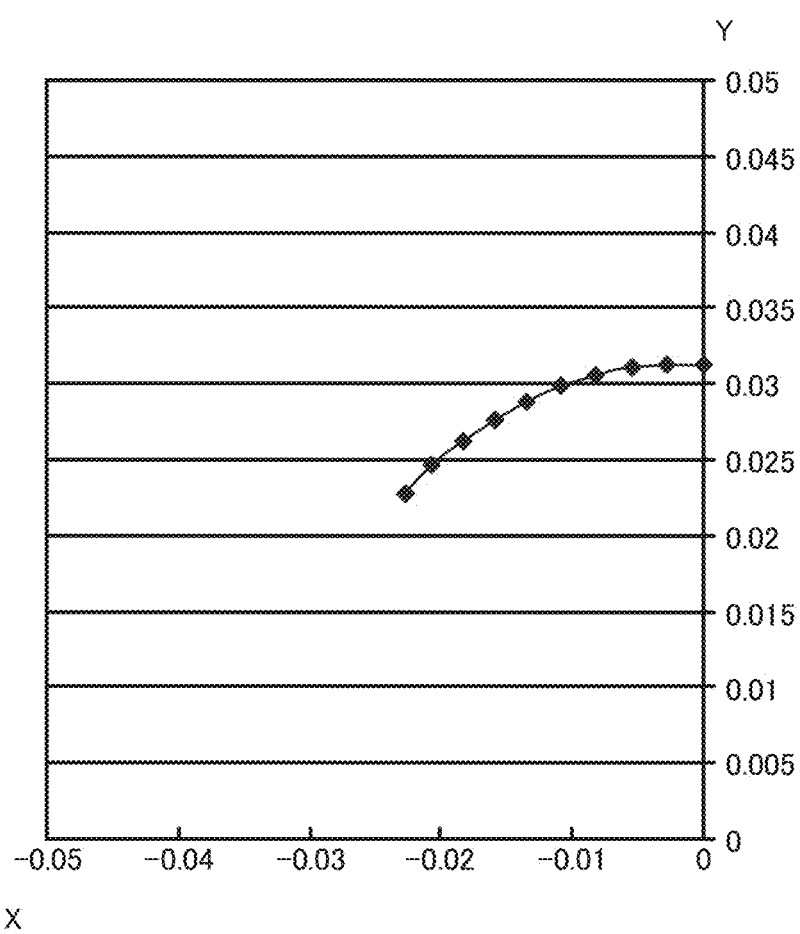
FIG. 23 is illustrative of image movement in Example 2 of the stereoscopic imaging optical system assembly 1.

FIG. 23 is illustrative of movement of an image in Example 2 of the stereoscopic imaging optical system assembly 1.

In Example 2 of the stereoscopic imaging optical system assembly 1 (not shown), the variable optical element 4 having such structure as depicted in FIG. 7 is applied to Example 1 of the stereoscopic imaging optical system assembly 1. Note here that the lens data on Example 2 are the same as in Example 1; so optical path and aberration diagrams are left out.

The variable optical element 4 of Example 2 includes a tilting surface, as shown in FIG. 7. The tilting surface has a tilt angle α of 2.467° that is an angle of the first surface portion 4a with respect to the XY plane at the first boundary step 4ab and an angle of the second surface portion 4b with respect to the XY plane at the second boundary step 4ba.

For focusing from a 50-mm object point to a 15-mm object point, the variable optical element 4 is rotated 45° with the center axis CR as center. For focusing from the 15-mm object point to a 1-mm object point, the variable optical element 4 is rotated 45° with the center axis CR as center. The thickest portion of the variable optical system $G_V$ is 0.754 mm and the thinnest portion is 0.709 mm, and the first 4a and the second surface portion 4b tilt continuously.

In Example 2 of the stereoscopic imaging optical system assembly 1, the image point moves in such an orbit as depicted in FIG. 23. The image point moves about 6% with respect to the image height. To keep this movement small, it is preferable that the variable optical system $G_V$ is located in the vicinity of the image plane.

In Example 3 of the stereoscopic imaging optical system assembly 1 (not shown), the variable optical element 5 having such structure as depicted in FIG. 8 is applied to Example 1 of the stereoscopic imaging optical system assembly 1. Note here that the lens data on Example 3 are the same as in Example 1; so optical path and aberration diagrams are left out.

The variable optical element 5 of Example 3 includes a helicoidal surface, as depicted in FIG. 8. The thickest portion of the variable optical element 5 is 0.754 mm, and the thinnest portion is 0.709 mm. The first 5a, and the second surface portion 5b has a continuous helicoidal shape. Even upon rotation of the variable optical element 5, the tilt of the surface through the optical path is kept invariably constant with no movement of the image point, because the variable optical element 5 has a continuous helicoidal shape.

The arrangement comprising the variable optical element 5 having such structure as depicted in FIG. 8 applied to Example 1 of the stereoscopic imaging optical system assembly 1 is preferable because light beams $Lo1_1$, $Lo1_2$ from the 1-mm object point, too, transmit through the first 5a and the second surface portion 5b of the helicoidal surface with no movement of the object point.

In Example 4 of the stereoscopic imaging optical system assembly 1 (not shown), the variable optical element 6 having such structure as depicted in FIGS. 10 and 14 is applied to Example 1 of the stereoscopic imaging optical system assembly 1.

The variable optical element 6 of Example 4 includes a radially tilting surface as depicted in FIG. 10 on the object side and a free-form surface as depicted in FIG. 14 on the image plane side. Upon application of the variable optical element 6 having such structure as depicted in FIGS. 10 and 14 to Example 1 of the stereoscopic imaging optical system assembly 1, it is located with varying surface separations. Note here that the radially tilting surface and free-form surface may be used with separate single optical elements.

At a portion of the variable optical element 6 through which light beams $Lo50_1$, $Lo50_2$ transmit when the object point is 50 mm, the variable optical element 6 has a thickness of 0.820 mm, and tilts 1.196° in a direction in which the center axis of rotation CR side is downward. The variable optical element 6 changes continuously from there, and at a portion of the variable optical element 6 through which light beams $Lo10_1$, $Lo10_2$ pass when the object point is 10 mm, the variable optical element 6 has a thickness of 0.700 mm and tilts 1.196° in a direction in which the center axis of rotation CR side is upward. In Example 4, the light beams $Lo50_1$, $Lo50_2$ at the time when the object point is 50 mm and the light beams $Lo10_1$, $Lo10_2$ at the time when the object point is 10 mm are located by 90° rotation of the variable optical element 6 for the sake of illustration only; they may be determined as desired.

It is here to be noted that the free-form surface of Example 4 has the same construction and arrangement as in Example 5 to be described later.

Figure 24:
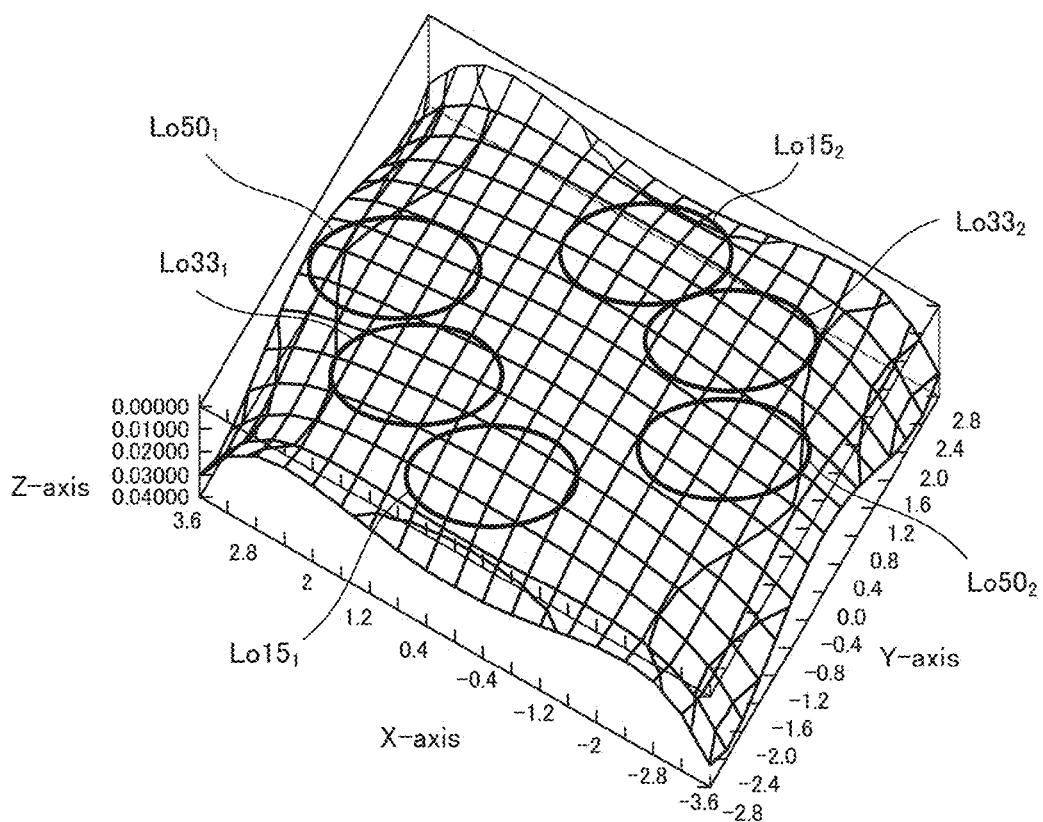
FIG. 24 is illustrative of the free-form surface shape of the variable optical element 7 in the variable optical system $G_V$ according to Example 5.
Figure 25:
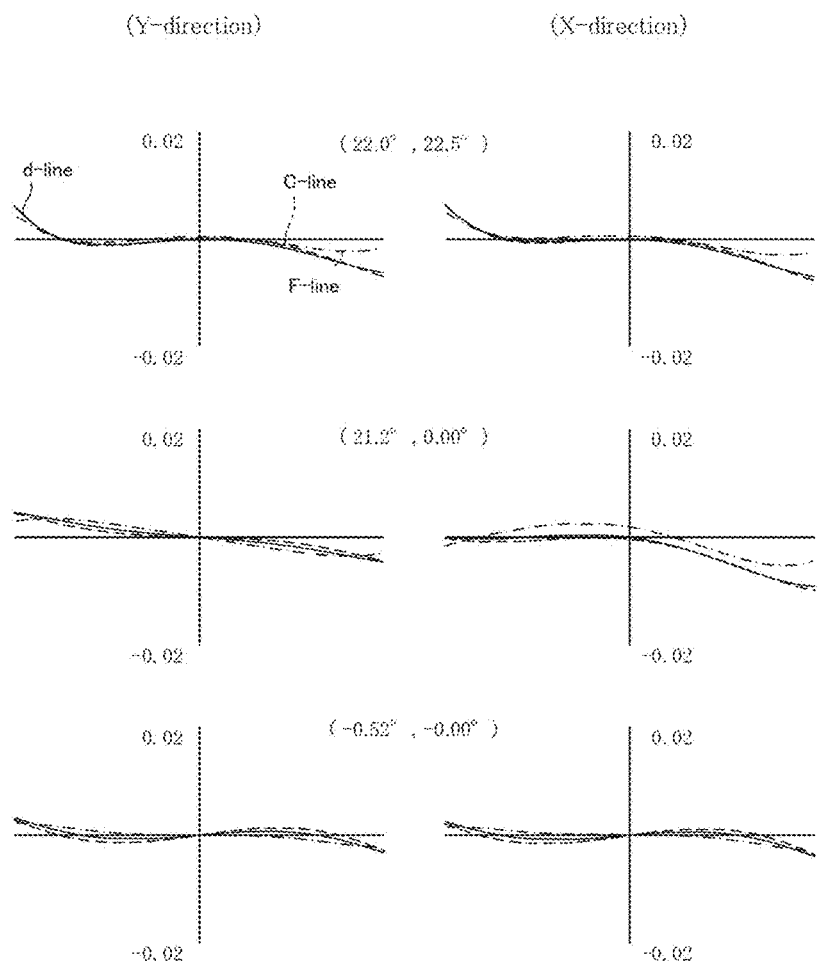
FIG. 25 is an aberration diagram at a far point for Example 5 of the stereoscopic imaging optical system assembly 1.
Figure 26:
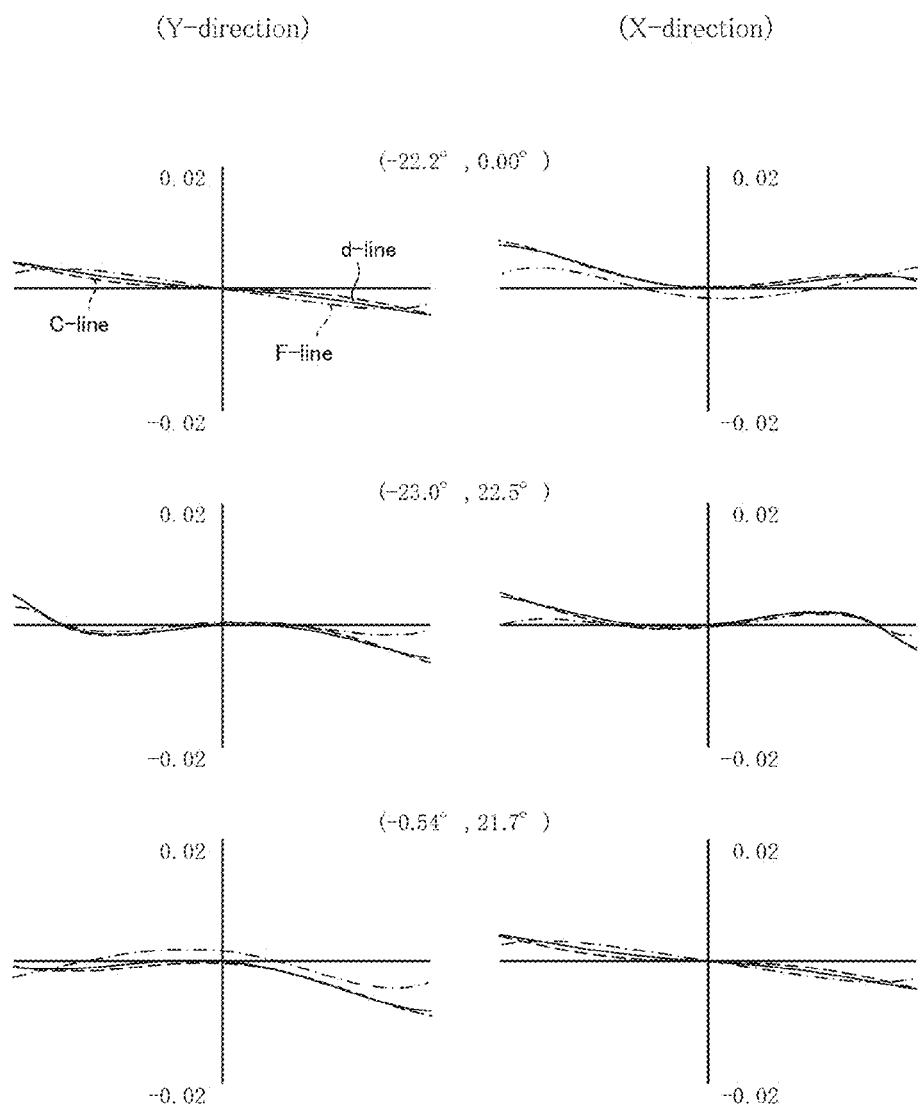
FIG. 26 is an aberration diagram at a far point for Example 5 of the stereoscopic imaging optical system assembly 1.
Figure 27:
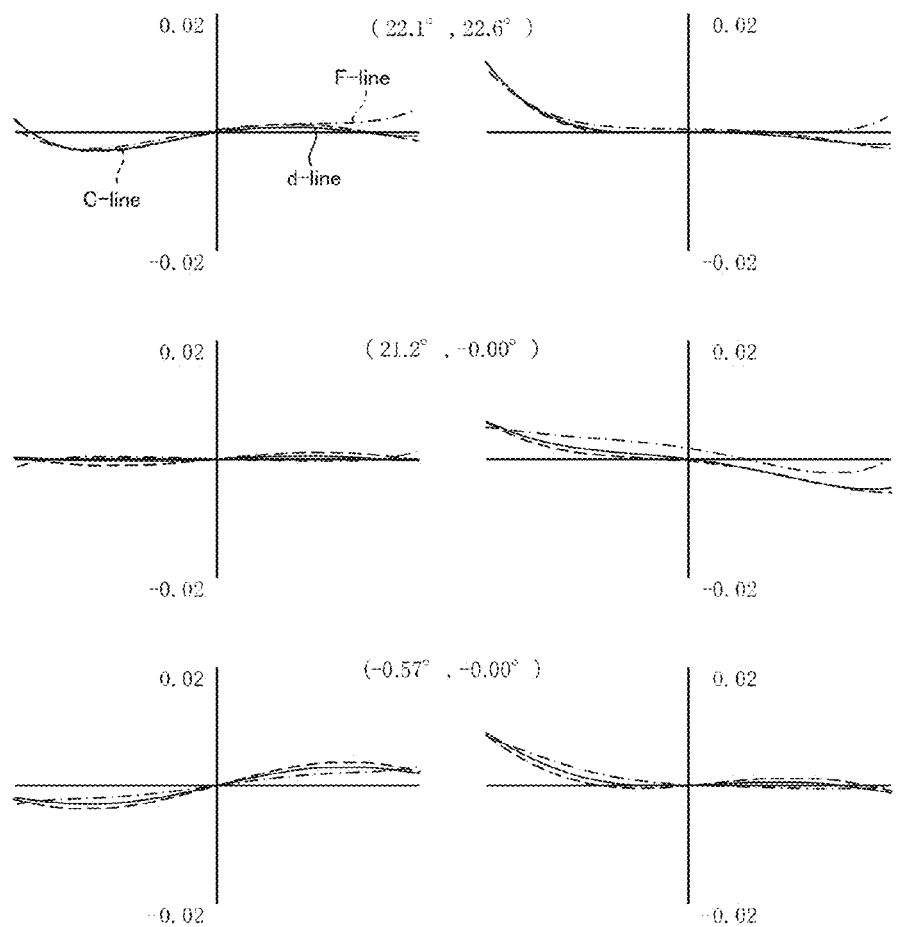
FIG. 27 is an aberration diagram at a near point for Example 5 of the stereoscopic imaging optical system assembly 1.
Figure 28:
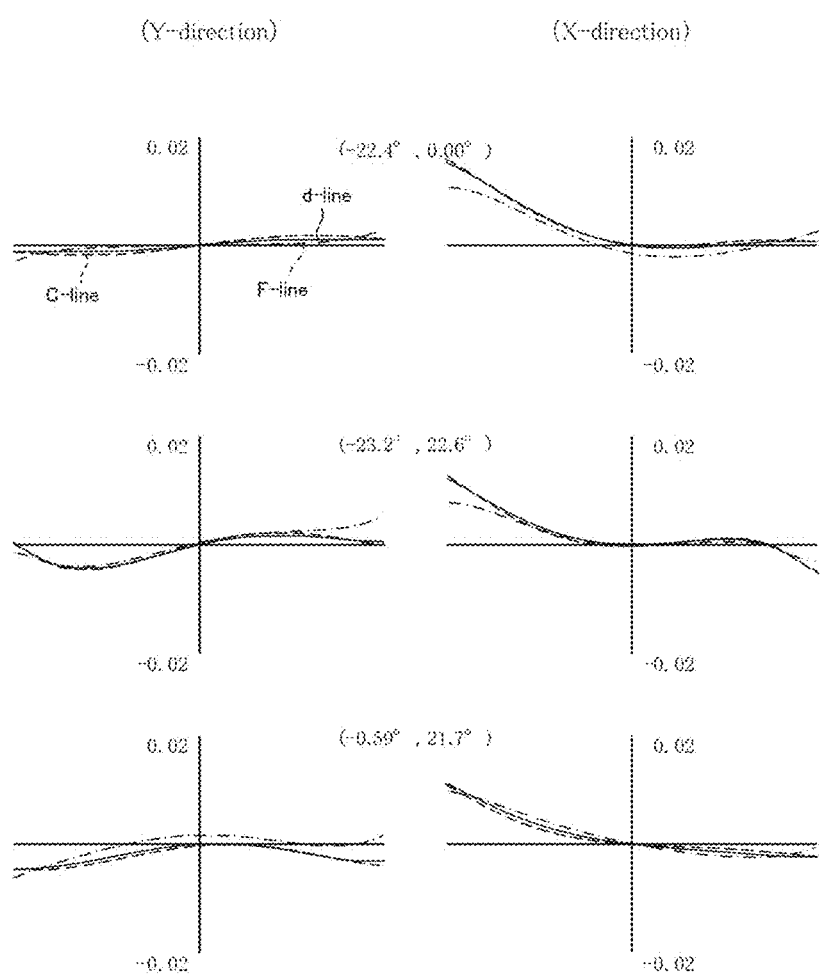
FIG. 28 is an aberration diagram at a near point for Example 5 of the stereoscopic imaging optical system assembly 1.

FIG. 24 is illustrative of the free-form surface shape of the variable optical element 7 forming the variable optical system $G_V$ in Example 5. FIGS. 25 and 26 are aberration diagrams at a far point for Example 5 of the stereoscopic imaging optical system assembly 1, and FIGS. 27 and 28 are aberration diagrams at a near point for Example 5 of the stereoscopic imaging optical system assembly 1.

In Example 5 of the stereoscopic imaging optical system assembly 1, the variable optical element 7 having such structure as depicted in FIG. 14 is applied to Example 1 of the stereoscopic imaging optical system assembly 1. Note here that lens data on Example 5 are the same as in Example 1; so any optical path diagram is omitted, and that the free-form surface of Example 5 has the same construction and arrangement as in Example 4.

The variable optical system $G_V$ of Example 5 includes the variable optical element 7. As shown in FIG. 24, the variable optical element 7 includes a smooth free-form surface that effects a partial curvature change for focusing. In the variable optical element 7 forming the variable optical system $G_V$ in Example 5, an area used for the 15-mm object point, relatively more convex than an area used for the 50-mm object point, is rotated for continuous focusing.

Figure 29:
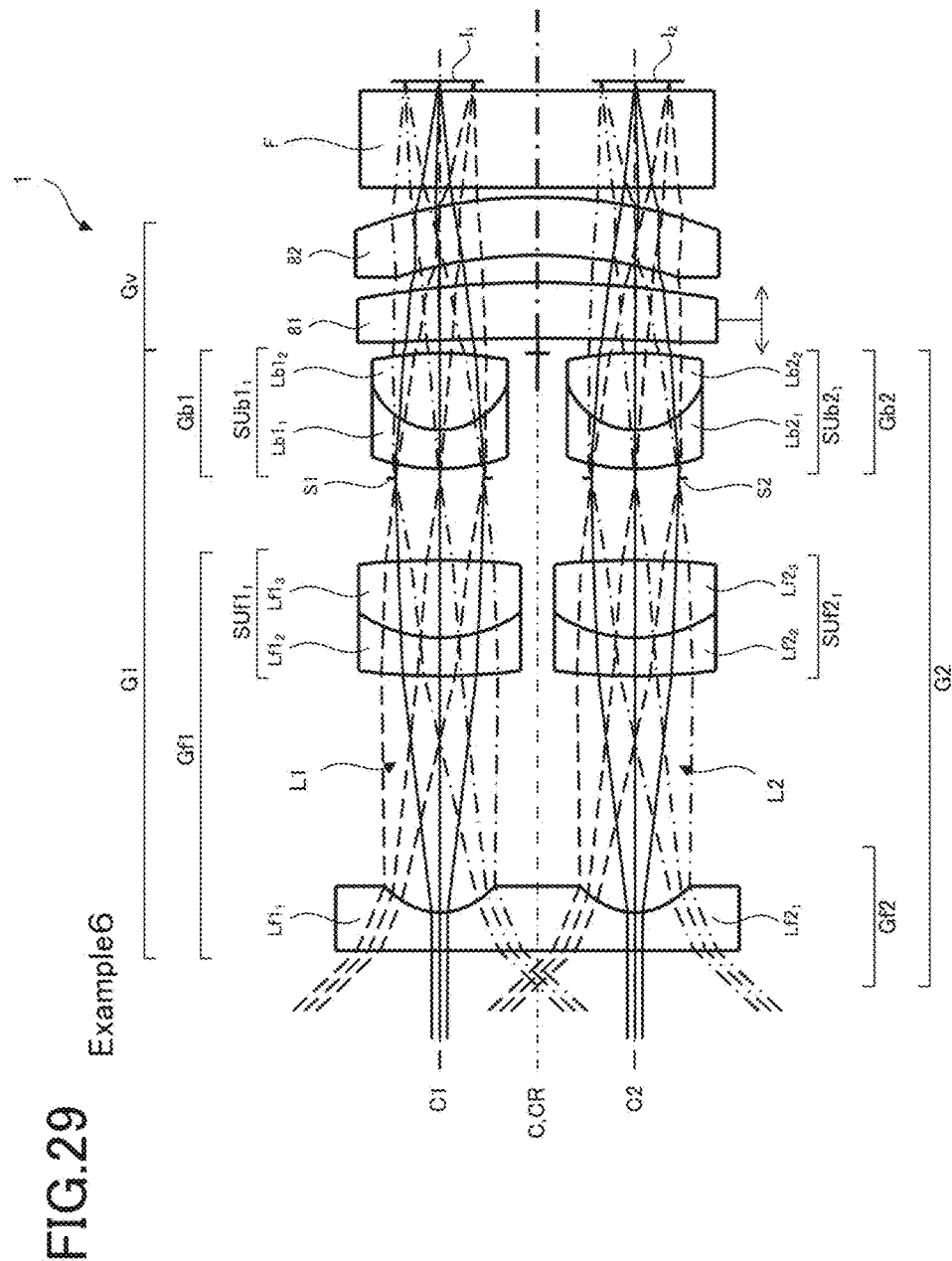
FIG. 29 is a sectional view of Example 6 of the stereoscopic imaging optical system assembly 1, as taken along its center axis C.
Figure 30:
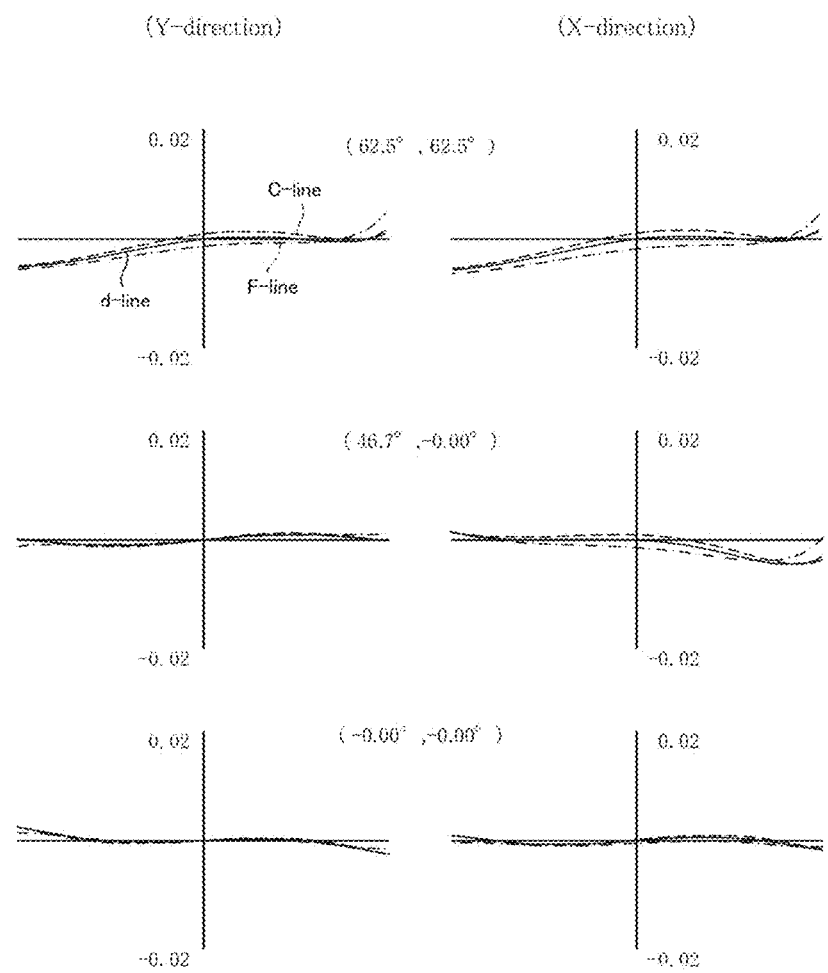
FIG. 30 is an aberration diagram at a far point for Example 6 of the stereoscopic imaging optical system assembly 1.
Figure 31:
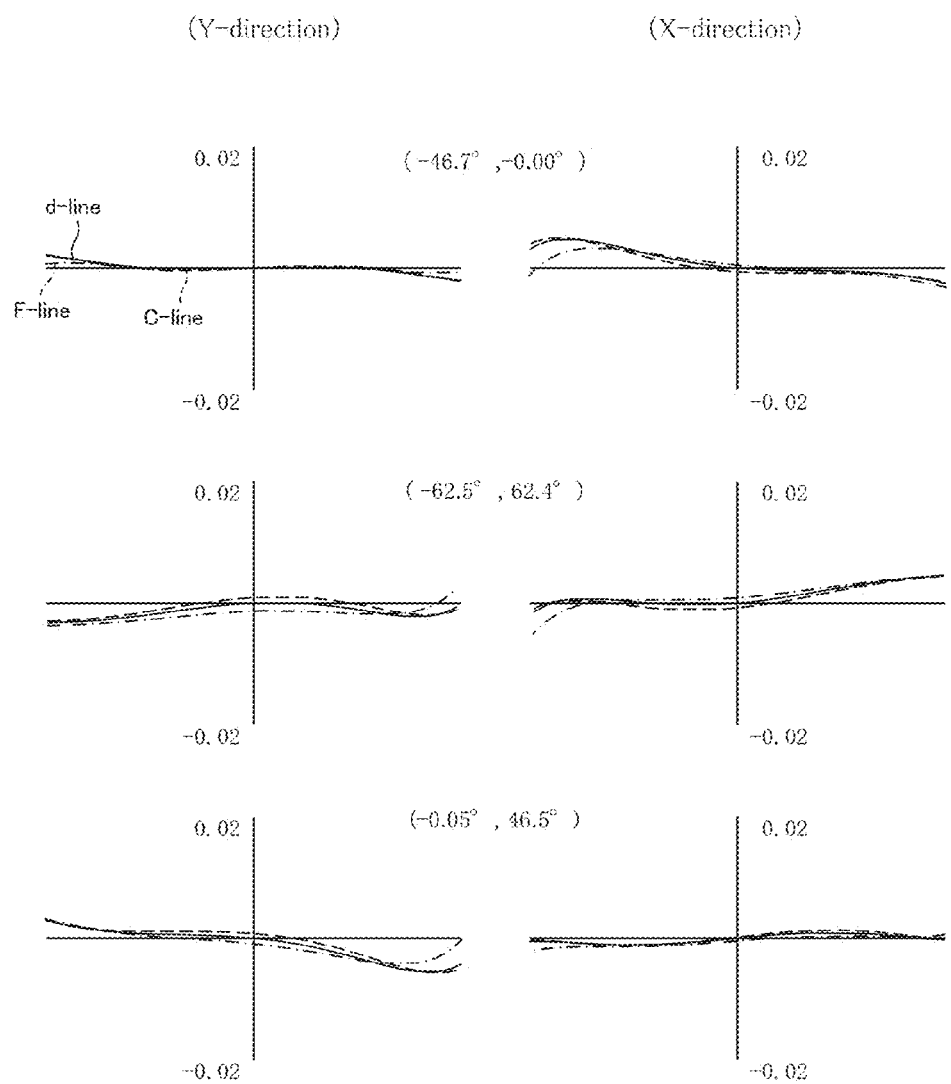
FIG. 31 is an aberration diagram at a far point for Example 6 of the stereoscopic imaging optical system assembly 1.
Figure 32:
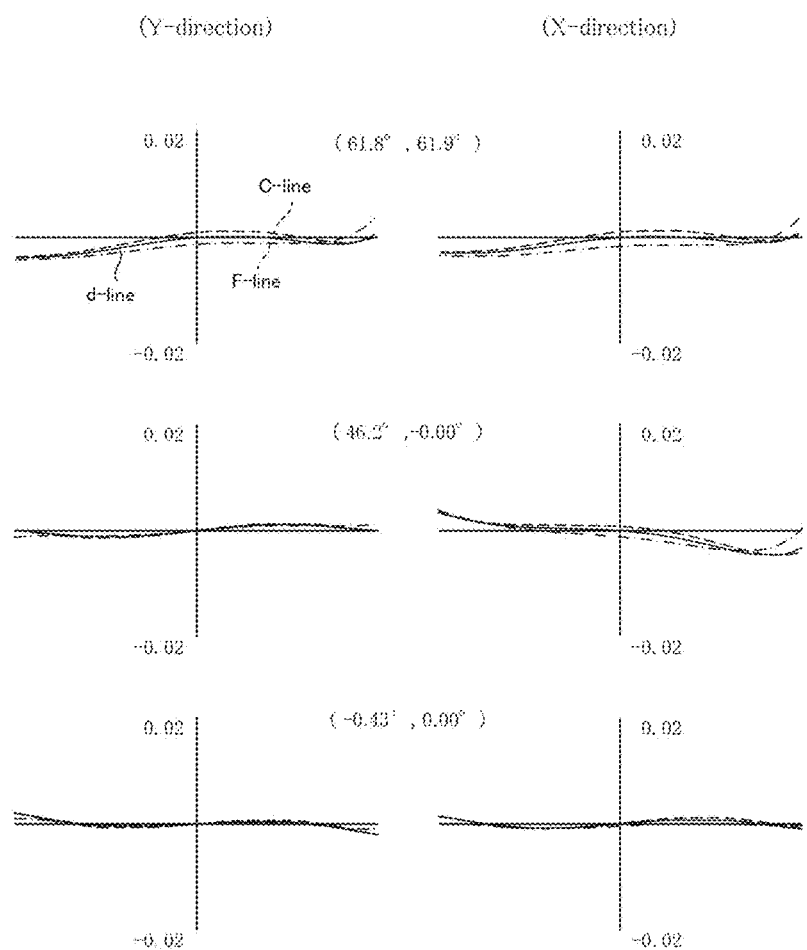
FIG. 32 is an aberration diagram at a near point for Example 6 of the stereoscopic imaging optical system assembly 1.
Figure 33:
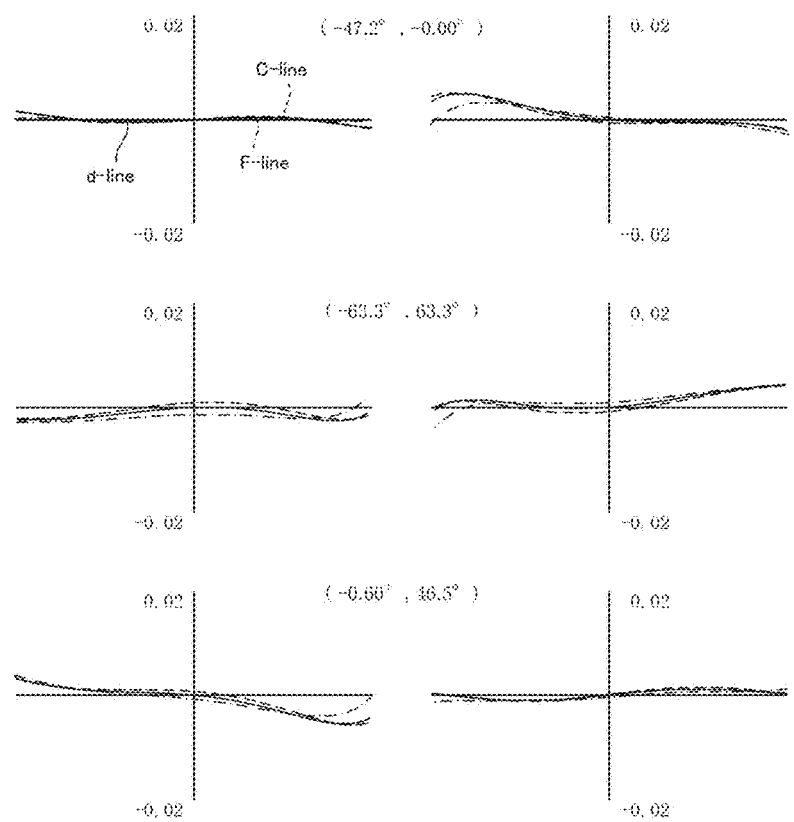
FIG. 33 is an aberration diagram at a near point for Example 6 of the stereoscopic imaging optical system assembly 1.
Figure 34:
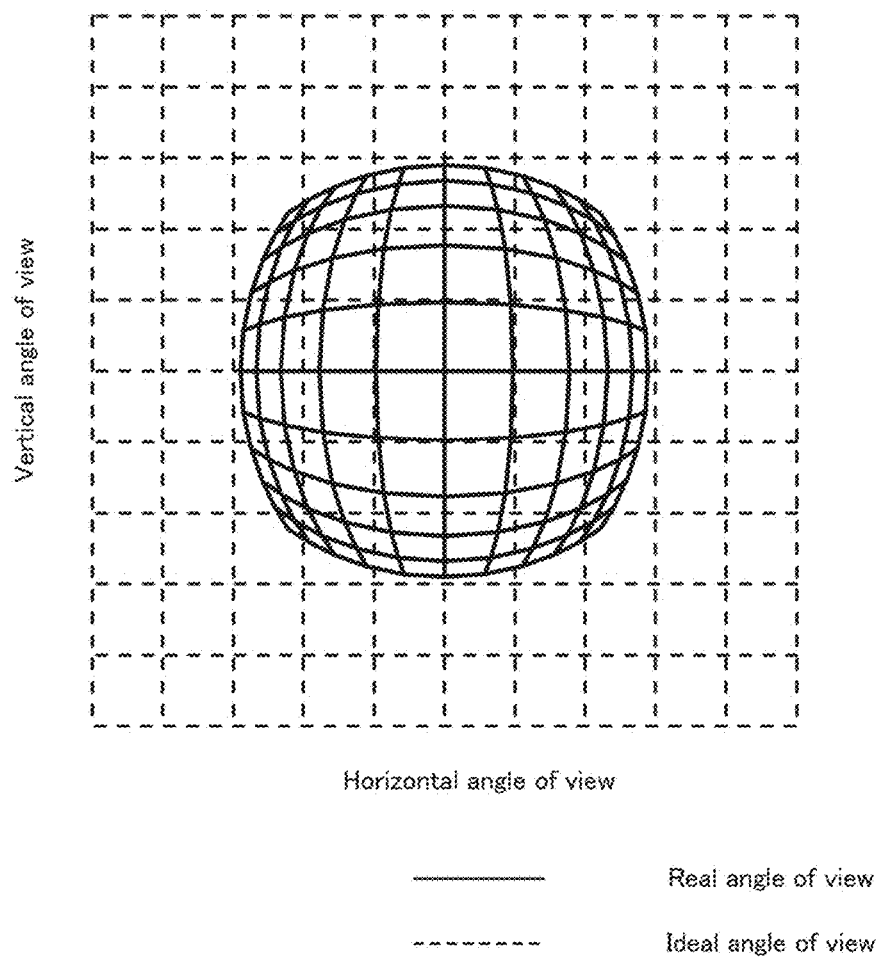
FIG. 34 is illustrative of image distortion in Example 6 of the stereoscopic imaging optical system assembly 1.

FIG. 29 is a sectional view of Example 6 of the stereoscopic imaging optical system assembly 1, as taken along the center axis C. FIGS. 30 and 31 are transverse aberration diagrams at a far point for Example 6 of the stereoscopic imaging optical system assembly 1, and FIGS. 32 and 33 are transverse aberration diagrams at a near point for Example 6 of the stereoscopic imaging optical system assembly 1. FIG. 34 is illustrative of image distortion in Example 6 of the stereoscopic imaging optical system assembly 1.

As shown in FIG. 29, Example 6 of the stereoscopic imaging optical system assembly 1 comprises, in order from the object side to the image plane side, a first optical system G1 with the first center axis C1 as an optical axis, a second optical system G2 with the first center axis C2 located in parallel with the center axis C1 as an optical axis, and a variable optical system $G_V$ having a single center axis C.

Parallel arrangement of the first G1 and the second optical system G2 makes stereoscopic observations possible.

The first optical system G1 includes, in order from the object side to the image plane side, a first front group Gf1 comprising a plano-double-concave negative lens $Lf1_1$, a first front-group cemented lens $SUf1_1$ consisting of a negative meniscus lens $Lf1_2$ convex on the object side and a double-convex positive lens $Lf1_2$, a first aperture S1, and a first rear group Gb1 comprising a first rear-group cemented lens $SUb1_1$ consisting of a negative meniscus lens $Lb1_1$ convex on the object side and a double-convex positive lens $Lb1_2$.

The second optical system G2 includes, in order from the object side to the image plane side, a plano-double-concave negative lens $Lf2_2$, a second front-group cemented lens $SUf2_1$ consisting of a negative meniscus lens $Lf2_2$ convex on the object side and a double-convex positive lens $Lf2_3$, a second aperture S2, and a second rear-group cemented lens $SUb2_1$ consisting of a negative meniscus lens $Lb2_1$ convex on the object side and a double-convex positive lens $Lb2_2$.

The variable optical system $G_V$ includes a first lens 81 comprising a positive meniscus lens convex on the image plane side and a second lens 82 comprising a negative meniscus lens convex on the image plane side. The first lens 81 forms a variable optical element and is movable in the center axis C direction. Focusing from a 33-mm object point to the 10-mm object point may be implemented by movement of the first lens 81 in the center axis C direction.

There is also a filter F located in front of the first image plane $I_1$, and the second image plane $I_2$.

A first light beam L1 incident on the first front group Gf1 from the first object plane (not shown) passes through the planoconcave negative lens $Lf1_1$, first front-group cemented lens $SUf1_1$, first aperture S1 and first rear-group cemented lens $SUb1_1$, and exits out of the first rear group Gb1, then entering the variable optical system $G_V$.

A second light beam L2 incident on the second front group Gf2 from the second object plane (not shown) passes through the planoconcave negative lens $Lf2_1$, second front-group cemented lens $SUf2_1$, second aperture S2 and second rear-group cemented lens $SUb2_1$, and exits out of the second rear group Gb2, then entering the variable optical system $G_V$.

The first and second light beams L1 and L2 incident on the variable optical system $G_V$ transmit through the first 81 and the second lens 82. Then, they enter the first and second image planes $I_1$ and $I_2$ through the filter F.

Figure 36:
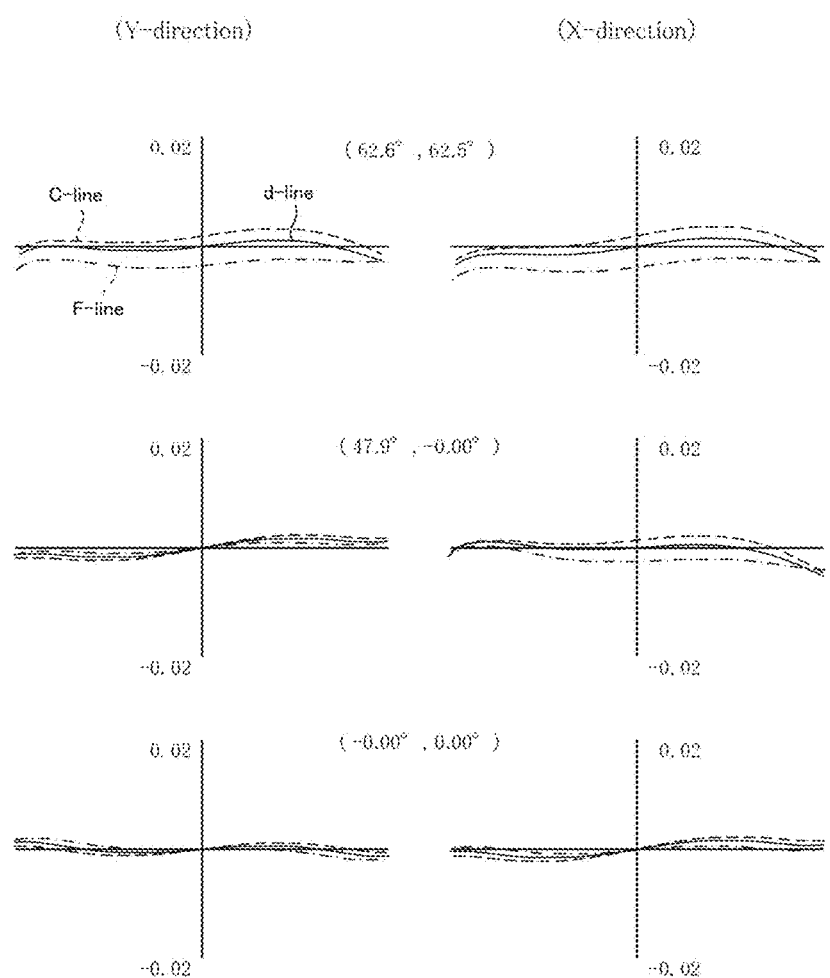
FIG. 36 is an aberration diagram at a far point for Example 7 of the stereoscopic imaging optical system assembly 1.
Figure 37:
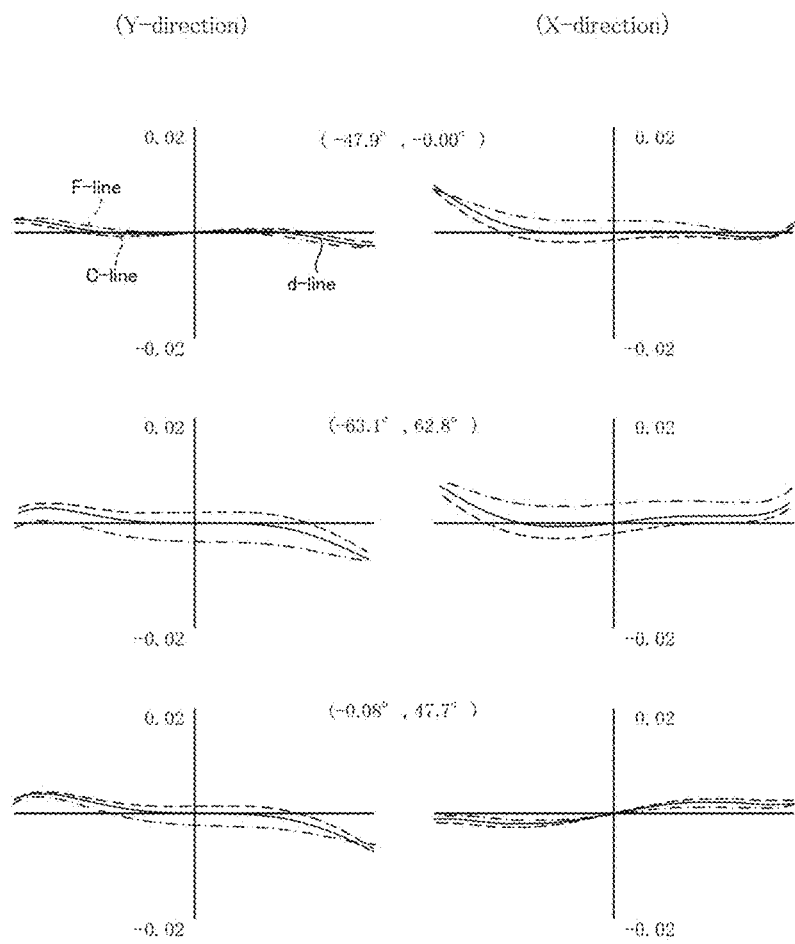
FIG. 37 is an aberration diagram at a far point for Example 7 of the stereoscopic imaging optical system assembly 1.
Figure 38:
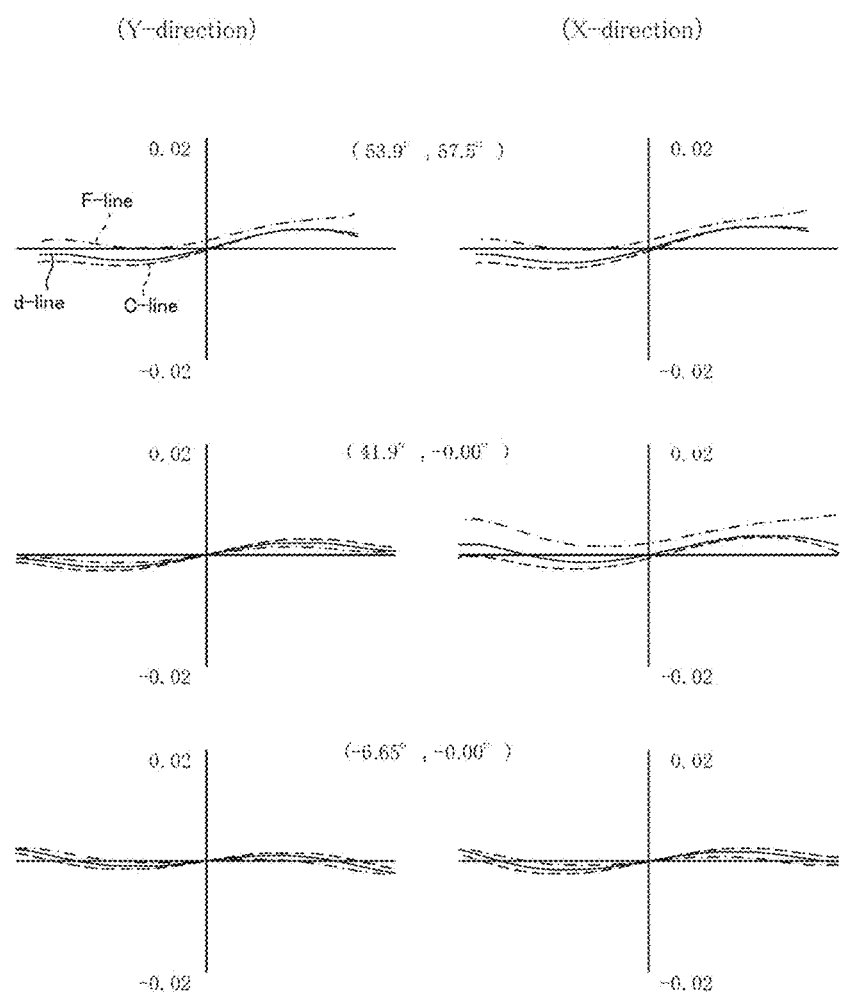
FIG. 38 is an aberration diagram at a near point for Example 7 of the stereoscopic imaging optical system assembly 1.
Figure 39:
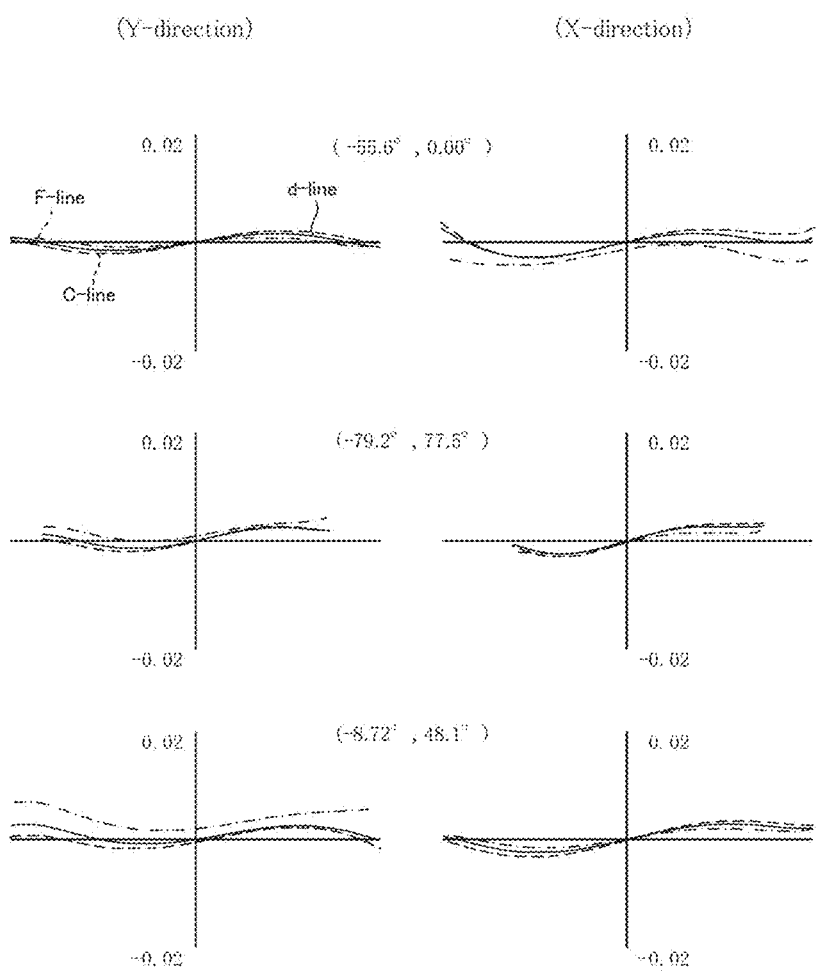
FIG. 39 is an aberration diagram at a near point for Example 7 of the stereoscopic imaging optical system assembly 1.
Figure 40:
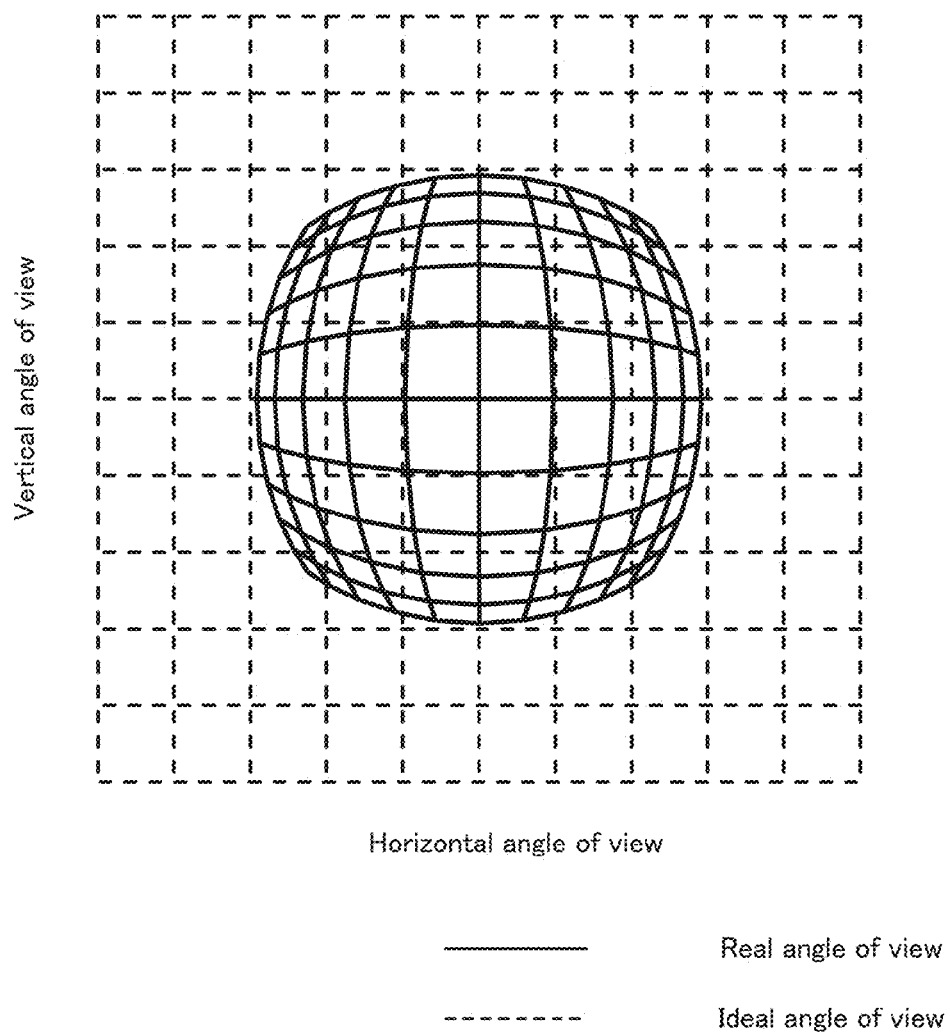
FIG. 40 is illustrative of image distortion in Example 7 of the stereoscopic imaging optical system assembly 1.

FIG. 37 is a sectional view of Example 7 of the stereoscopic imaging optical system assembly 1, as taken along the center axis C. FIGS. 36 and 37 are transverse aberration diagrams at a far point for Example 7 of the stereoscopic imaging optical system assembly 1, and FIGS. 38 and 39 are transverse aberration diagrams at a near point for Example 7 of the stereoscopic imaging optical system assembly 1. FIG. 40 is illustrative of image distortion in Example 7 of the stereoscopic imaging optical system assembly 1.

Figure 35:
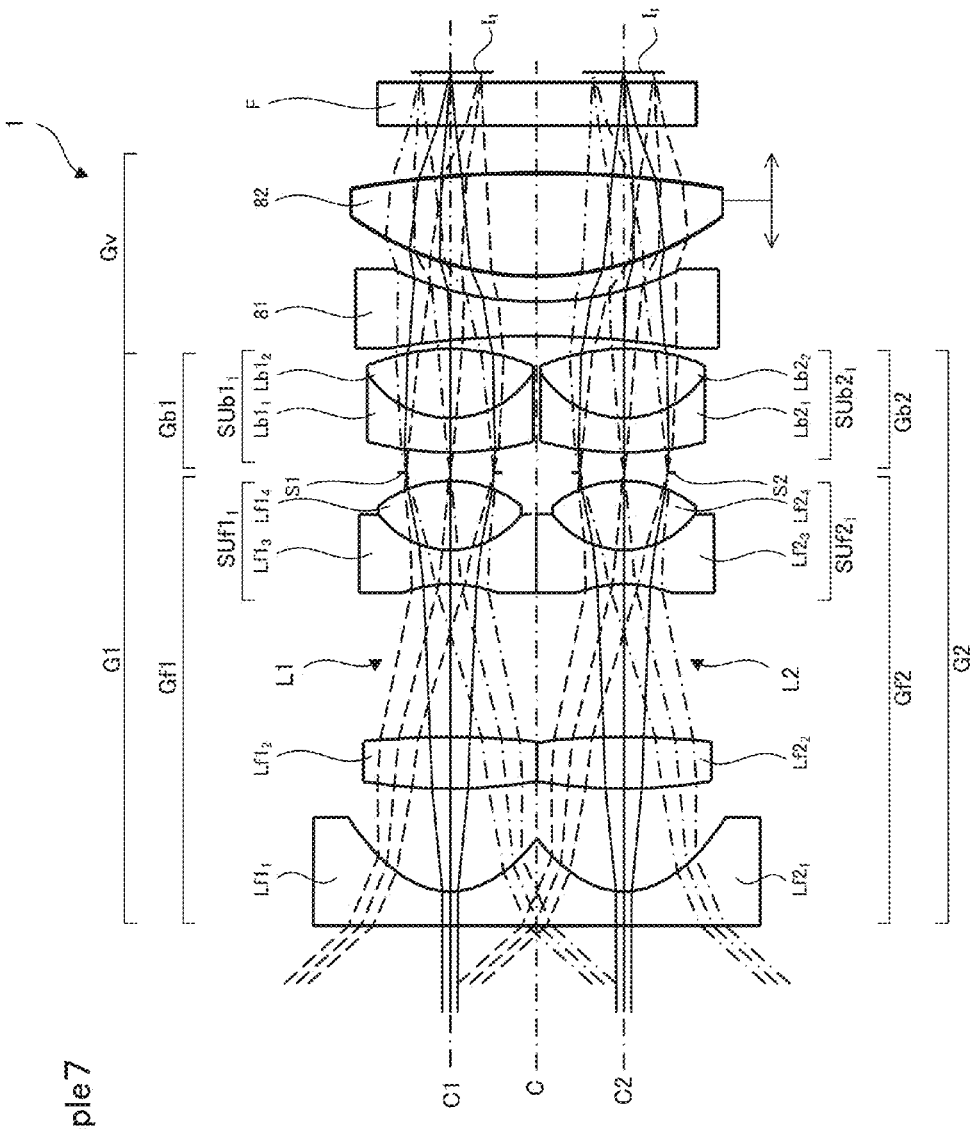
FIG. 35 is a sectional view of Example 7 of the stereoscopic imaging optical system assembly 1, as taken along its center axis C.

As shown in FIG. 35, Example 7 of the stereoscopic imaging optical system assembly 1 comprises, in order from the object side to the image plane side, a first optical system G1 with the first center axis C1 as an optical axis, a second optical system G2 with the second center axis C2 located in parallel with the center axis C1 as an optical axis, and a variable optical system $G_V$ having a single center axis C.

Parallel arrangement of the first G1 and the second optical system G2 makes stereoscopic observations possible.

The first optical system G1 includes, in order from the object side to the image plane side, a first front group Gf1 comprising a planoconcave negative lens $Lf1_1$, a double-convex positive lens $Lf2_2$, a first front-group cemented lens $SUf1_1$ consisting of a double-concave negative lens $Lf1_3$ and a double-convex positive lens $Lf1_4$, a first aperture S1, and a first rear group Gb1 comprising a first rear-group cemented lens $SUb1_1$ consisting of a negative meniscus lens $Lb1_1$ convex on the object side and a double-convex positive lens $Lb1_2$.

The second optical system G2 includes, in order from the object side to the image plane side, a second front group Gf2 comprising a planoconcave negative lens $Lf2_1$, a double-convex positive lens $Lf2_2$, and a second front-group cemented lens $SUf2_1$ consisting of a double-concave negative lens $Lf2_3$ and a double-convex positive lens $Lf2_4$, a second aperture S2, and a second rear group Gb2 comprising a second rear-group cemented lens $SUb2_1$ consisting of a negative meniscus lens $Lb2_1$ convex on the object side and a double-convex positive lens $Lb2_2$.

The variable optical system $G_V$ includes a first lens 81 comprising a double-concave negative lens and a second lens 82 comprising a double-convex positive lens. The second lens 82 forms a variable optical element that is movable in the center axis C direction. Focusing from the 33-mm object point to a 0-mm object point may be implemented by movement of the second lens 82 in the center axis C direction.

There is a filter F located in front of the first image plane $I_1$, and the second image plane $I_2$.

A first light beam L1 incident on the front group Gf1 from the first object plane (not shown) passes through the planoconcave negative lens $Lf1_1$, double-convex positive lens $Lf1_2$, first front-group cemented lens $SUf1_1$, first aperture S1 and first rear-group cemented lens $SUb1_1$ and exits out of the first rear group Gb1, then entering the variable optical system $G_V$.

A second light beam L2 incident on the second front group Gf2 from the second object plane (not shown) passes through the planoconcave negative lens $Lf2_1$, double-convex positive lens $Lf2_2$, second front-group cemented lens $SUf2_1$, second aperture S2 and second rear-group cemented lens $SUb2_1$ and exits out of the second rear group Gb2, then entering the variable optical system $G_V$.

The first and second light beams L1 and L2 incident on the variable optical system $G_V$ transmit through the first and second lenses 81 and 82. Then, they enter the first and second image planes $I_1$ and $I_2$ through the filter F.

Figure 41:
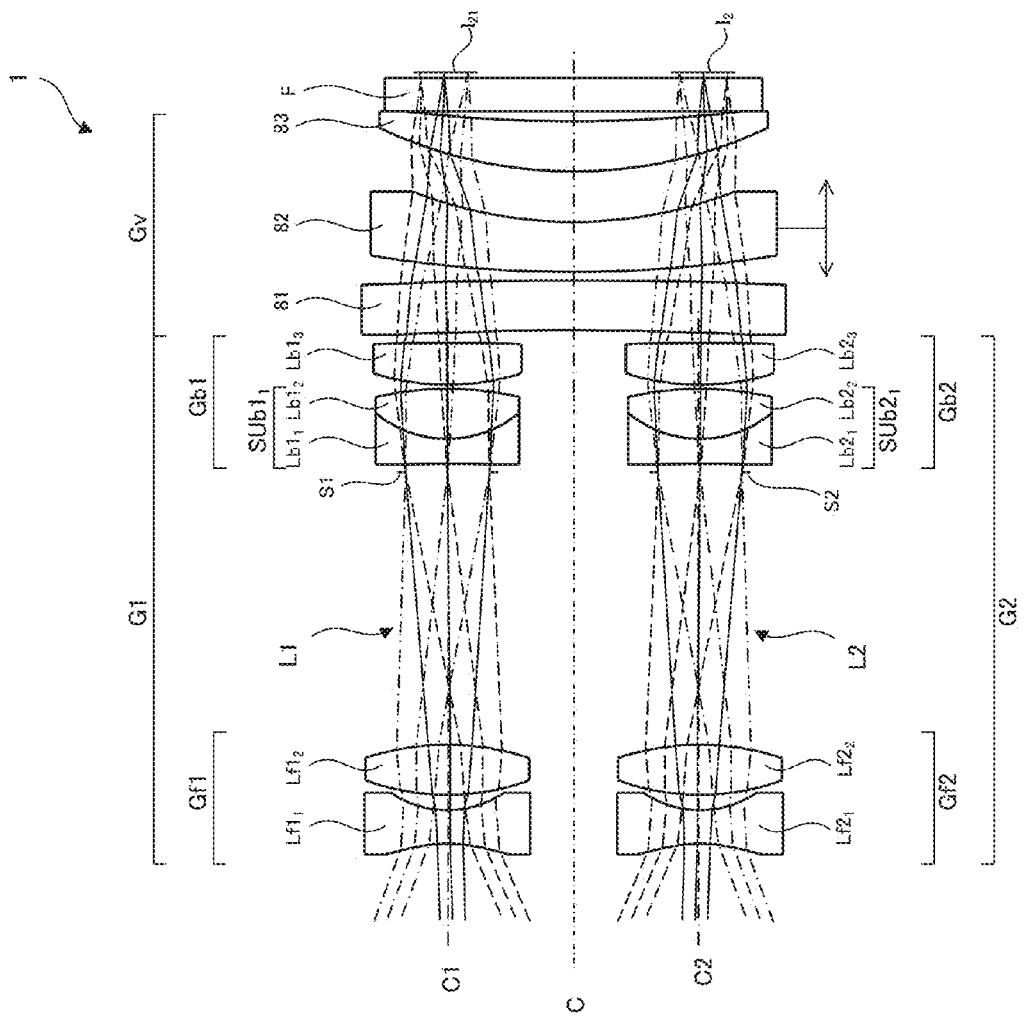
FIG. 41 is a sectional view of Example 8 of the stereoscopic imaging optical system assembly 1, as taken along its center axis C.
Figure 42:
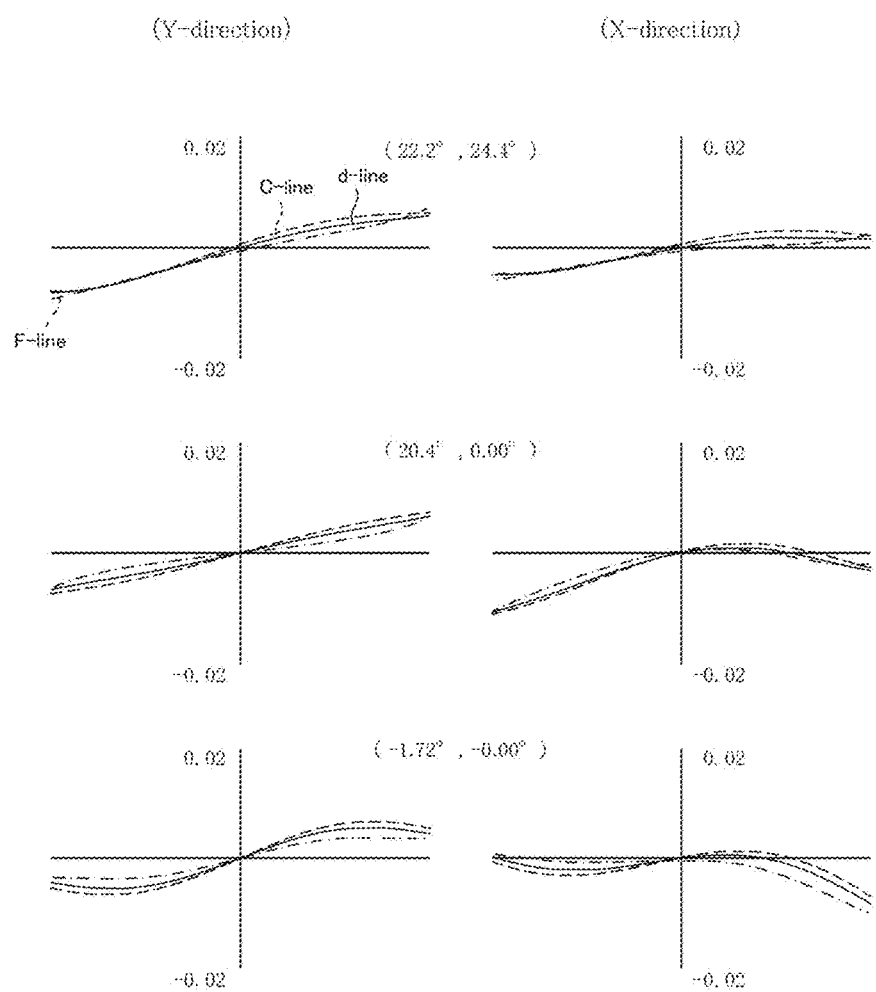
FIG. 42 is an aberration diagram at a far point for Example 8 of the stereoscopic imaging optical system assembly 1.
Figure 43:
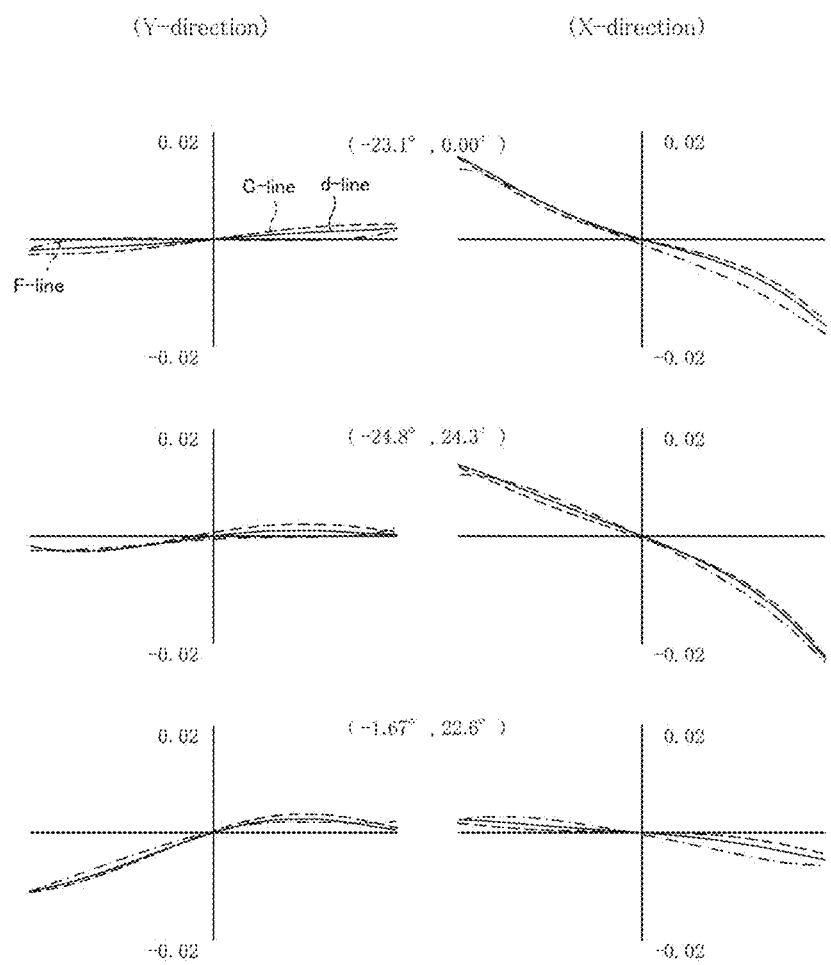
FIG. 43 is an aberration diagram at a far point for Example 8 of the stereoscopic imaging optical system assembly 1.
Figure 44:
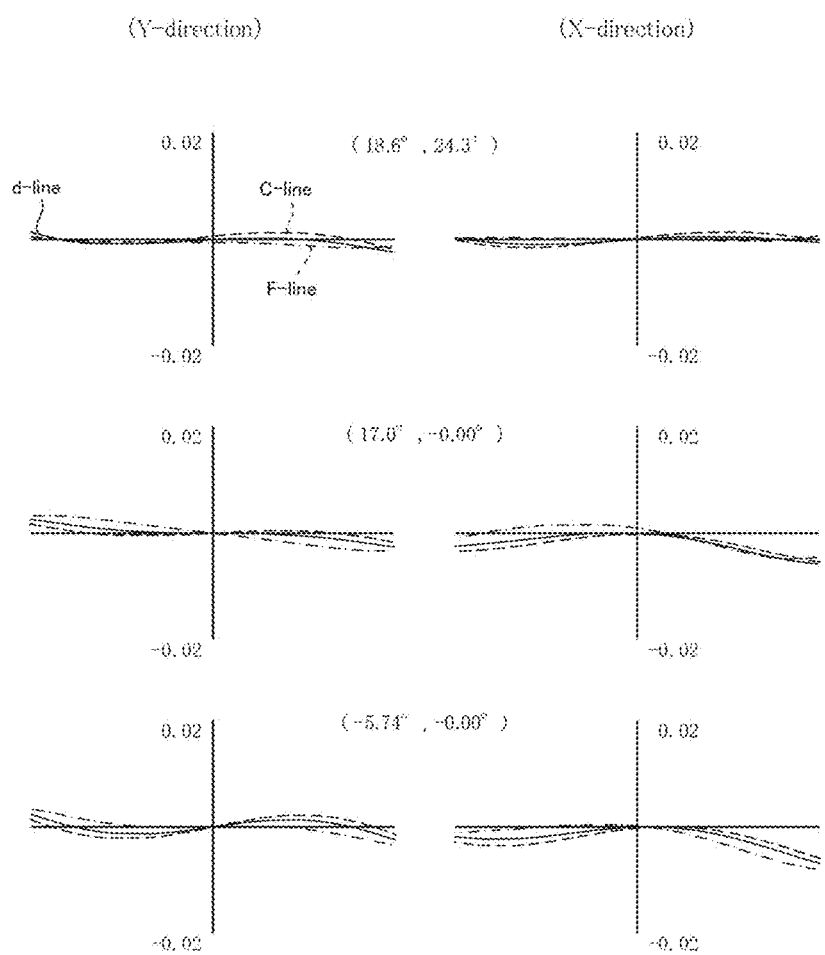
FIG. 44 is an aberration diagram at a near point for Example 8 of the stereoscopic imaging optical system assembly 1.
Figure 45:
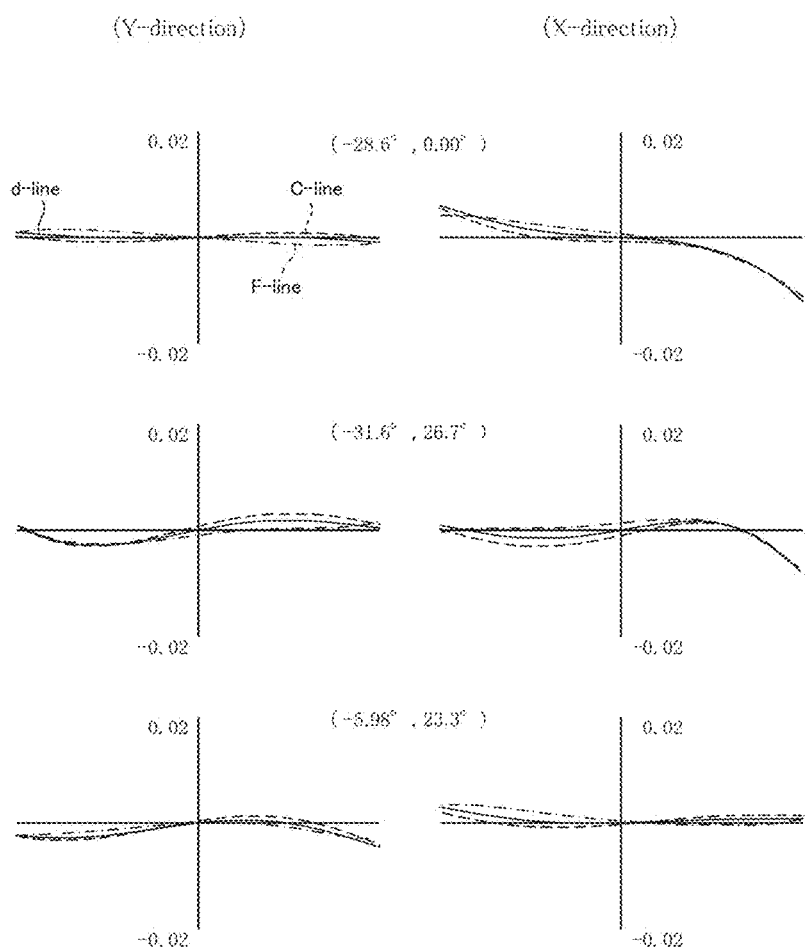
FIG. 45 is an aberration diagram at a near point for Example 8 of the stereoscopic imaging optical system assembly 1.
Figure 46:
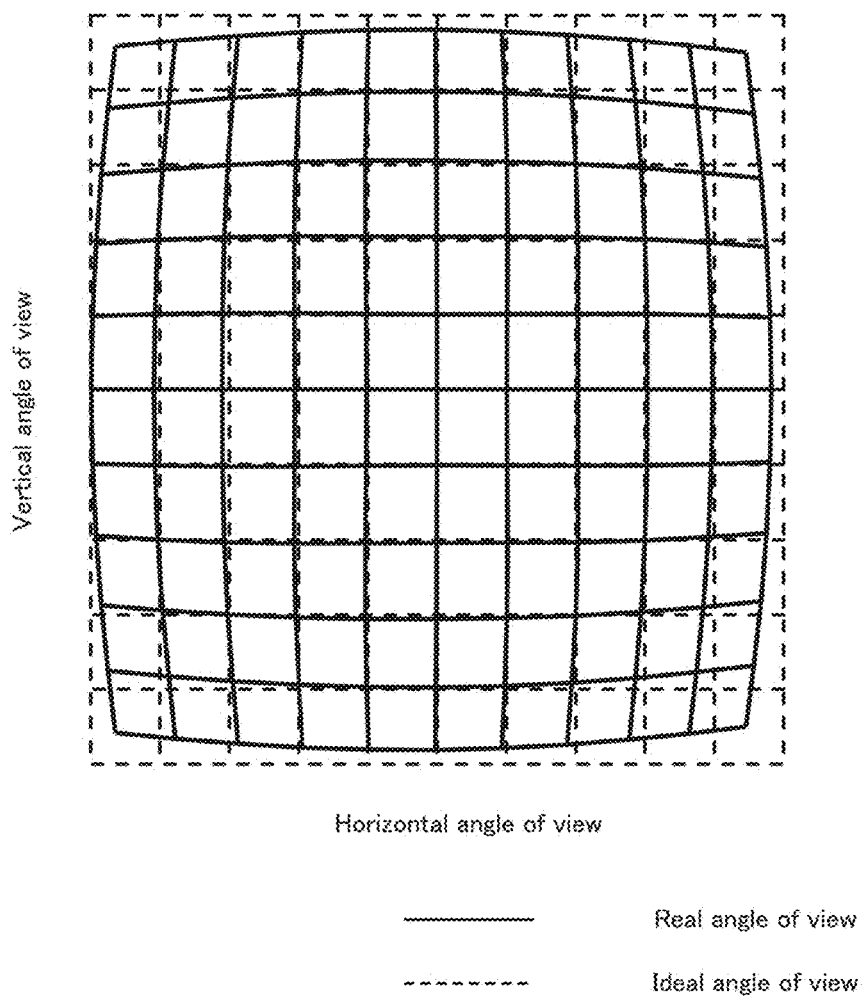
FIG. 46 is illustrative of image distortion in Example 8 of the stereoscopic imaging optical system assembly 1.

FIG. 41 is a sectional view of Example 8 of the stereoscopic imaging optical system assembly 1, as taken along the center axis C. FIGS. 42 and 43 are transverse aberration diagrams at a far point for Example 8 of the stereoscopic imaging optical system assembly 1, and FIGS. 44 and 45 are transverse aberration diagrams at a near point for Example 8 of the stereoscopic imaging optical system assembly 1. FIG. 46 is illustrative of image distortion in Example 8 of the stereoscopic imaging optical system assembly 1.

As shown in FIG. 41, Example 8 of the stereoscopic imaging optical system assembly 1 comprises, in order from the object side to the image plane side, a first optical system G1 with the first center axis C1 as an optical axis, a second optical system G2 with the second center axis C2 located in parallel with the center axis C2 as an optical axis, and a variable optical system $G_V$ having a single center axis C.

Parallel arrangement of the first G1 and the second optical system G2 makes stereoscopic observations possible.

The first optical system G1 includes, in order from the object side to the image plane side, a first front group Gf1 comprising a double-concave negative lens $Lf1_1$ and a double-convex positive lens $Lf1_2$, a first aperture S1, and a first rear group G1 comprising a first rear-group cemented lens $SUb1_1$ consisting of a double-concave negative lens $Lb1_1$ and a double-convex positive lens $Lb1_2$ and a double-convex positive lens $Lb1_3$.

The second optical system G2 includes, in order from the object side to the image plane side, a second front group Gf2 comprising a double-concave negative lens $Lf2_1$ and a double-convex positive lens $Lf2_2$, a second aperture S2, and a second rear group Gb2 comprising a second rear-group cemented lens $SUb2_1$ consisting of a double-concave negative lens $Lb2_1$ and a double-convex positive lens $Lb2_2$ and a double-convex positive lens $Lb2_3$.

The variable optical system $G_V$ includes a first lens 81 comprising a negative meniscus lens convex on the image plane side, a second lens 82 comprising a negative meniscus lens convex on the object side, and a third lens 83 comprising a positive meniscus lens convex on the object side. The second lens 82 forms a variable optical element that is movable in the center axis C direction. By movement of the second lens 82 in the center axis C direction, vergence control from 62.500 mm to 18.750 mm may be implemented.

There is a filter F in front of the first and second image planes $I_1$ and $I_2$.

A first light beam L1 incident on the first front group Gf1 from the first object plane (not shown) passes through the planoconcave negative lens $Lf1_1$, double-convex positive lens $Lf1_2$, first aperture S1, first rear-group cemented lens $SUb1_1$ and double-convex positive lens $Lb1_3$ and exits out of the first rear group Gb1, then entering the variable optical system $G_V$.

A second light beam L2 incident on the second front group Gf2 from the second object plane (not shown) passes through the planoconcave negative lens $Lf2_1$, double-convex positive lens $Lf2_2$, second aperture S2, second rear-group cemented lens $SUb2_1$ and double-convex positive lens $Lb2_3$, and exits out of the second rear group Gb2, then entering the variable optical system $G_V$.

The first and second light beams L1 and l2 incident on the variable optical system $G_V$ transmit through the first, second and third lenses 81, 82 and 83. Then, they enter the first and second image planes $I_1$ and $I_2$ through the filter F.

Figure 47:
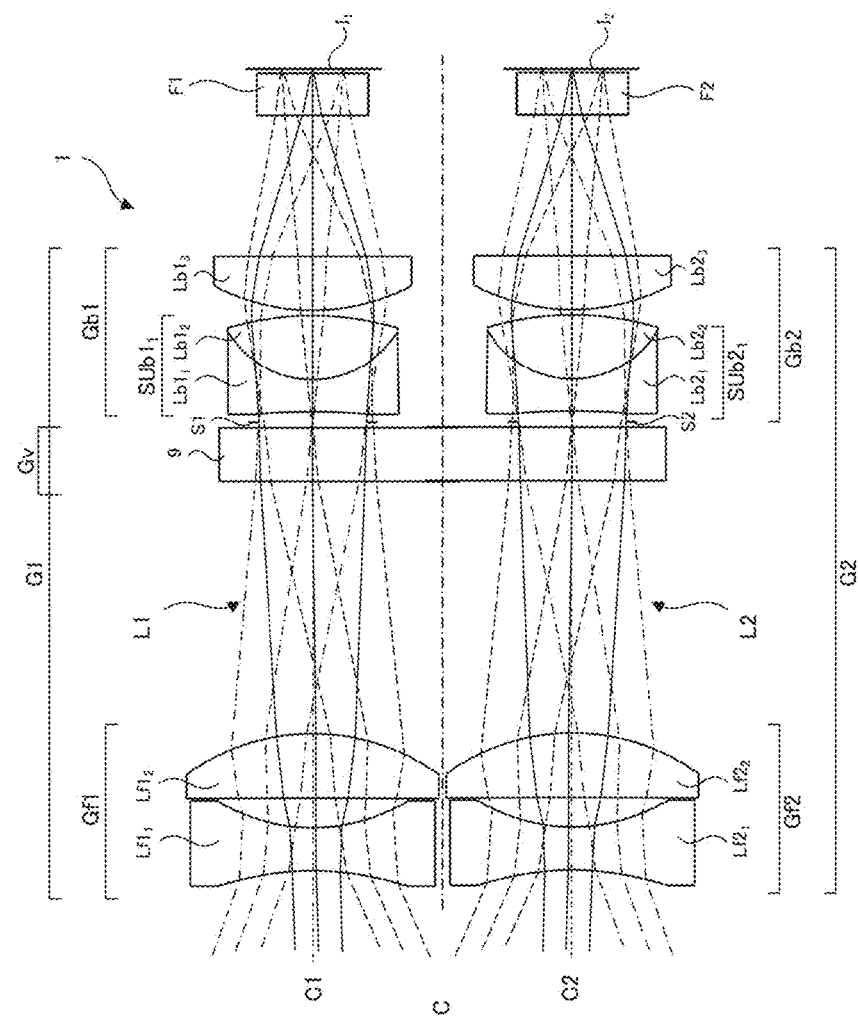
FIG. 47 is a sectional view of Example 9 of the stereoscopic imaging optical system assembly 1, as taken along its center axis C.
Figure 48:
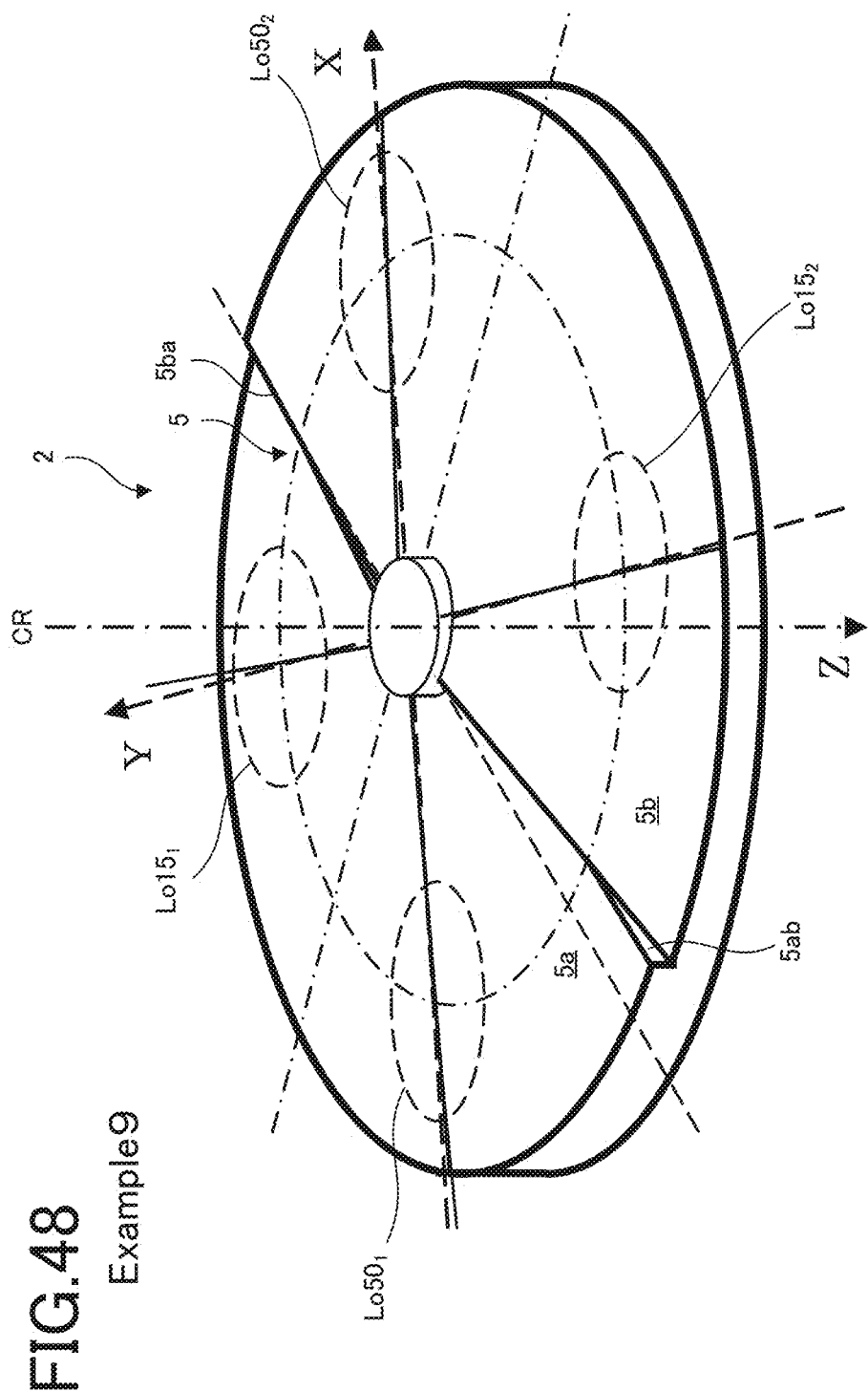
FIG. 48 is illustrative in conception of the object side surface of the variable optical element 9 in Example 9.
Figure 49:
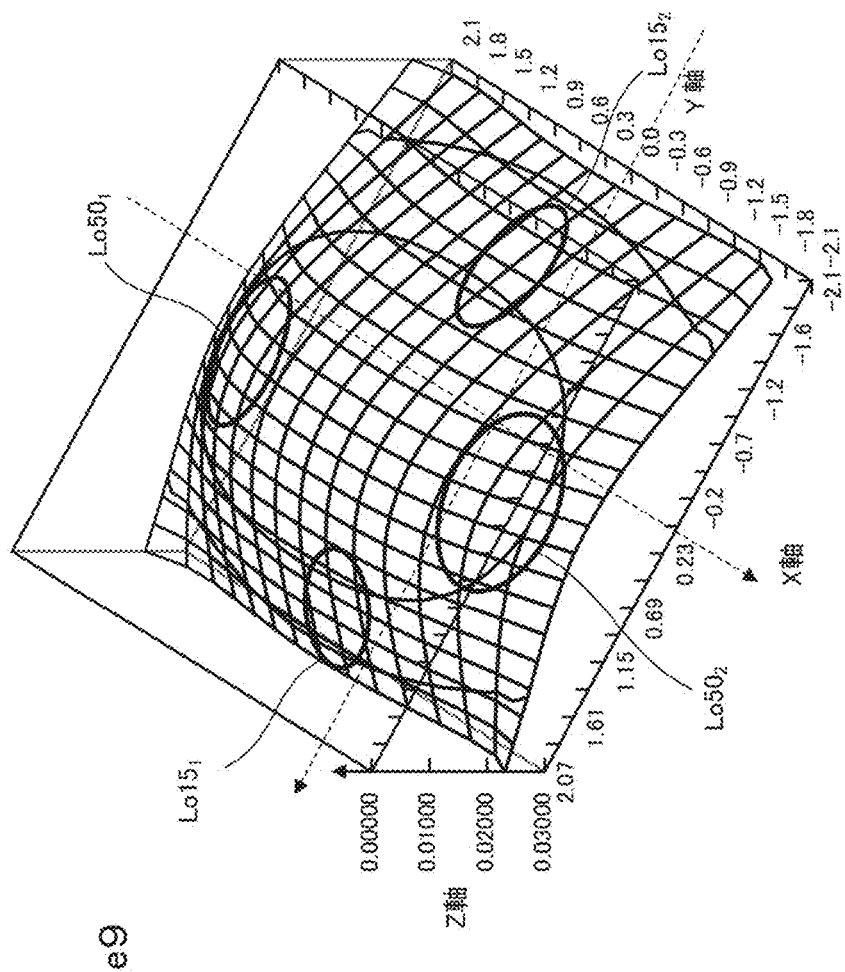
FIG. 49 is illustrative in conception of the image plane side surface of the variable optical element 9 in Example 9.
Figure 50:
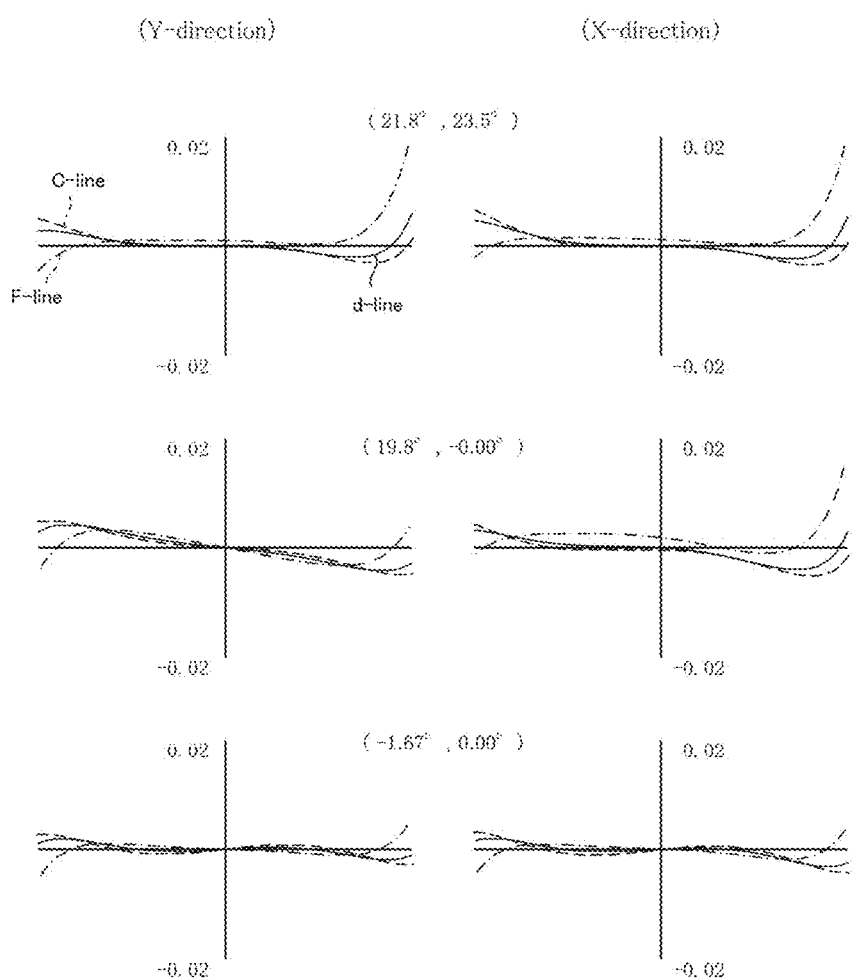
FIG. 50 is an aberration diagram at a far point for Example 9 of the stereoscopic imaging optical system assembly 1.
Figure 51:
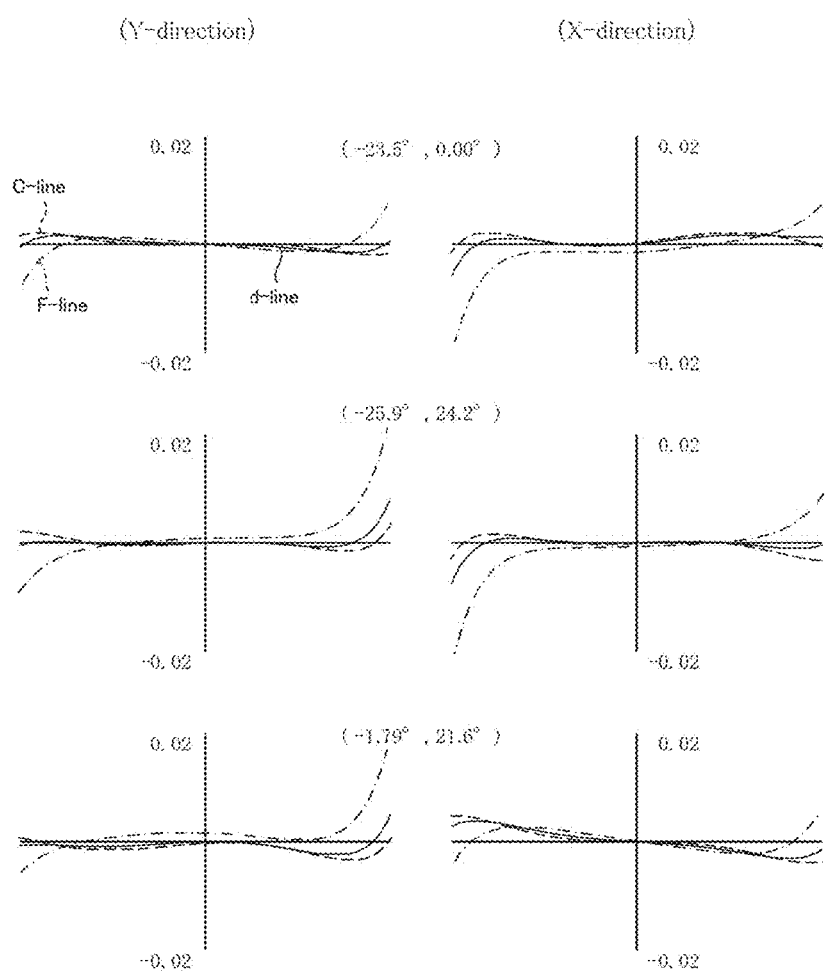
FIG. 51 is an aberration diagram at a far point for Example 9 of the stereoscopic imaging optical system assembly 1.
Figure 52:
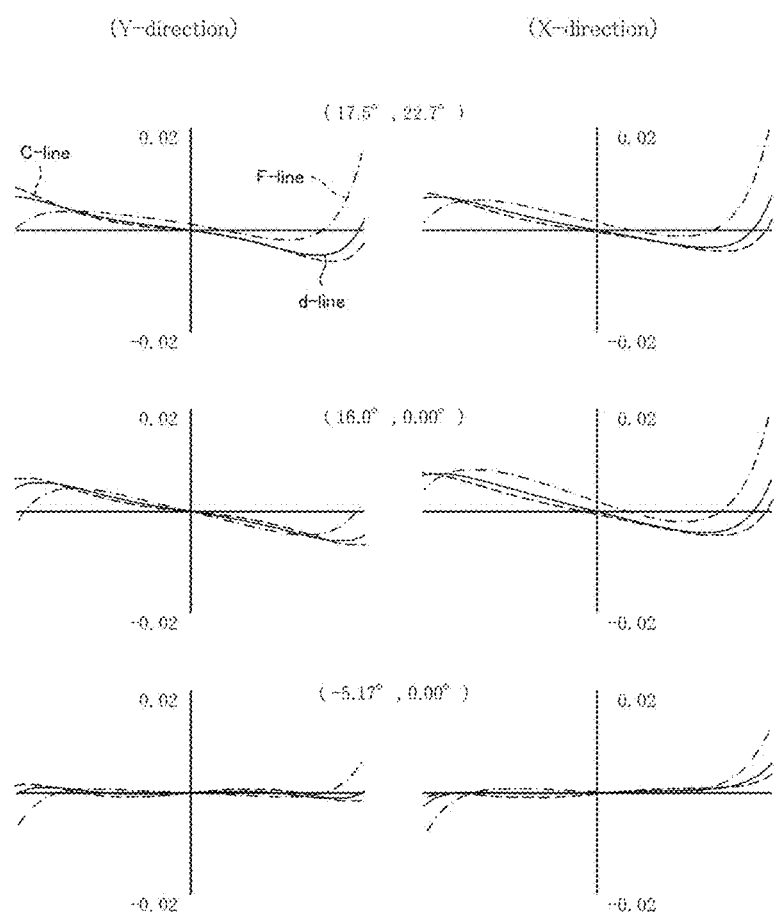
FIG. 52 is an aberration diagram at a near point for Example 9 of the stereoscopic imaging optical system assembly 1.
Figure 53:
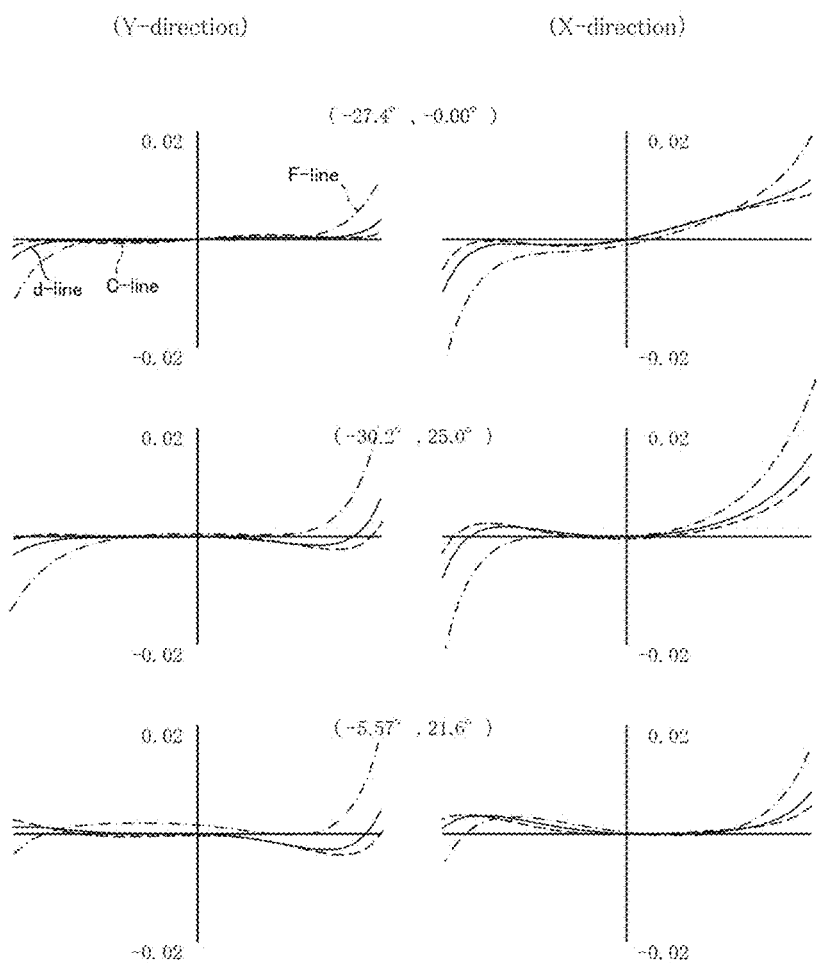
FIG. 53 is an aberration diagram at a near point for Example 9 of the stereoscopic imaging optical system assembly 1.
Figure 54:
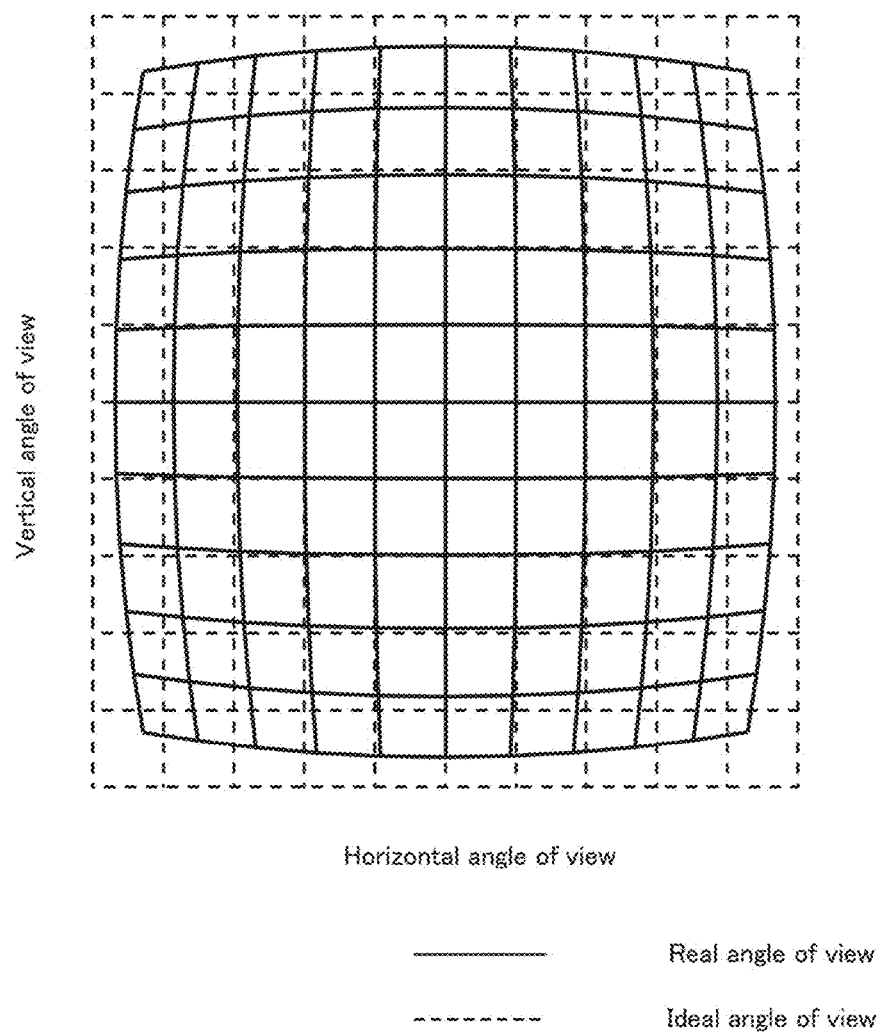
FIG. 54 is illustrative of image distortion in Example 9 of the stereoscopic imaging optical system assembly 1.

FIG. 47 is a sectional view of Example 9 of the stereoscopic imaging optical system assembly 1, as taken along the center axis C. FIG. 48 is illustrative in conception of the object-side surface of the variable optical element in Example 9, and FIG. 49 is illustrative in conception of the image plane side-surface of the variable optical element in Example 9. FIGS. 50 and 51 are transverse aberration diagrams at a far point for Example 9 of the stereoscopic imaging optical system assembly 1, and FIGS. 52 and 53 are transverse aberration diagrams at a near point for Example 9 of the stereoscopic imaging optical system assembly 1. FIG. 54 is representative of image distortion in Example 9 of the stereoscopic imaging optical system assembly 1.

As shown in FIG. 47, Example 9 of the stereoscopic imaging optical system assembly 1 includes, in order from the object side to the image plane side, a first front group Gf1 of a first optical system G1 with the first center axis C1 as an optical axis, a second front group Gf2 of a second optical system G2 with the second center axis C2 arranged in parallel with the first center axis C1 as an optical axis, a variable optical system $G_V$ having a single center axis C, and a second rear group Gb2 of the second optical system G2 with the second center axis C2 arranged in parallel with the first center axis C1 as an optical axis.

Parallel arrangement of the first and second optical systems G1 and G2 makes stereoscopic observations possible. The separation between the first C1 and the second center axis C2 is 3 mm.

The first front group Gf1 of the first optical system G1 includes, in order from the object side to the image plane side, a double-concave negative lens $Lf1_1$ and a positive meniscus lens $Lf1_2$ convex on the image plane side, and the rear group Gb1 includes a first aperture S1, a first rear-group cemented lens $SUb1_1$ consisting of a double-concave negative lens $Lb1_1$ and a double-convex positive lens $Lb1_2$, and a positive meniscus lens $Lb1_3$ convex on the object side.

The second front group Gf2 of the second optical system G2 includes, in order form the object side to the image plane side, a double-concave negative lens $Lf2_1$ and a positive meniscus lens $Lf2_2$ convex on the image plane side, and the second rear group Gb2 includes a second aperture S2, a second rear-group cemented lens $SUb2_1$ consisting of a double-concave negative lens $Lb2_1$ and a double-convex positive lens $Lb2_2$, and a positive meniscus lens $Lb2_3$ convex on the object side.

The variable optical system $G_V$ includes a variable optical element including, in order from the object side to the image plane side, the radially tilting helicoidal surface shown in FIG. 48, and the free-form surface shown in FIG. 49.

As shown in FIG. 48, the variable optical element 9 has a radially tilting helicoidal surface on the object side. At a portion of the variable optical element 9 through which light beams $Lo50_1$, $Lo50_2$ from the 50-mm object point pass, it tilts 0.044° in a direction in which the center axis of rotation CR side is upward. The variable optical element 9 changes continuously from there and at a portion thereof through which the light beams $Lo15_1$, $Lo15_2$ from the 15-mm object point pass, it tilts 2.094° in a direction in which the center axis of rotation CR side is upward. The center thickness of the light beams is kept invariably at 0.625 mm all around. In Example 9, the light beams $Lo50_1$, $Lo50_2$ from the 50-mm object point and the light beams $Lo15_1$, $Lo15_2$ from the 15-mm object point are rotated 90° as an example; however, they may be rotated as desired.

As depicted in FIG. 49, the variable optical element 9 has a smooth free-form surface to effect a partial curvature change for focusing. In the variable optical element 9 forming the variable optical system $G_V$ of Example 9, an area used for the 15-mm object point, relatively more convex than an area used for the 50-mm object point, is rotated for continuous focusing.

A first filter F1 and a second filter F2 are located in front of the first image planes $I_1$ and $I_2$, respectively.

A first light beam L1 incident on the first front group Gf1 from the first object plane (not shown) passes through the double-concave negative lens $Lf1_1$, positive meniscus lens $Lf1_2$ convex on the image plane side, variable optical element 9, first aperture S1, first rear-group cemented lens $SUb1_1$ and positive meniscus lens $Lb1_3$ convex on the object side and exits out of the first rear group Gb1, then entering the first image plane $I_1$ through the first filter F1.

A second light beam L2 incident on the second front group Gf2 from the first object plane (not shown) passes through the double-concave negative lens $Lf2_1$, positive meniscus lens $Lf2_2$ convex on the image plane side, variable optical element 9, second aperture S2, second rear-group cemented lens $SUb2_1$ and positive meniscus lens $Lb2_3$ convex on the object side and exits out of the second rear group Gb2, then entering the second image plane $I_2$ through the second filter F2.

Figure 55:
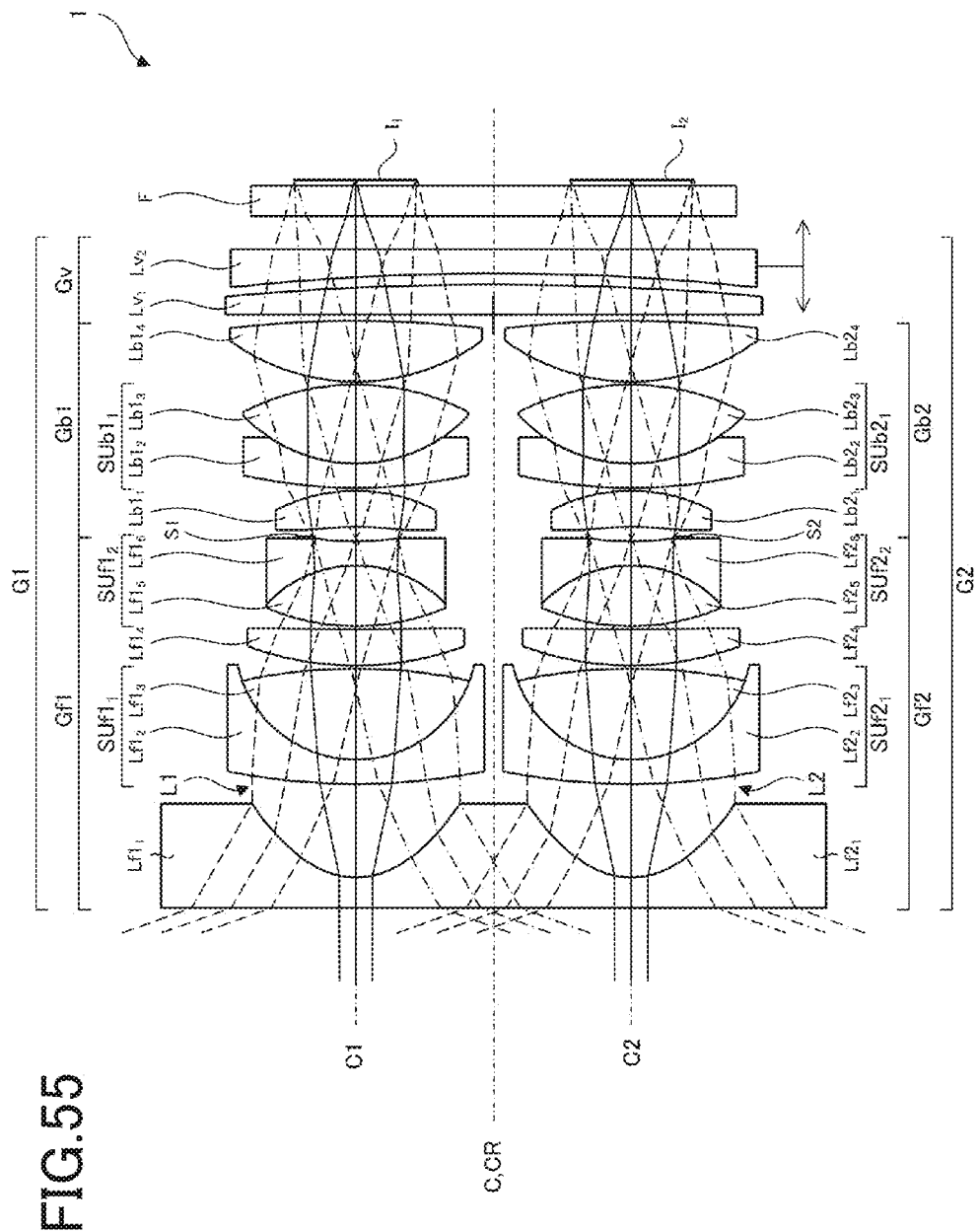
FIG. 55 is a sectional view of Example 10 of the stereoscopic imaging optical system assembly 1, as taken along its center axis C.
Figure 56A:
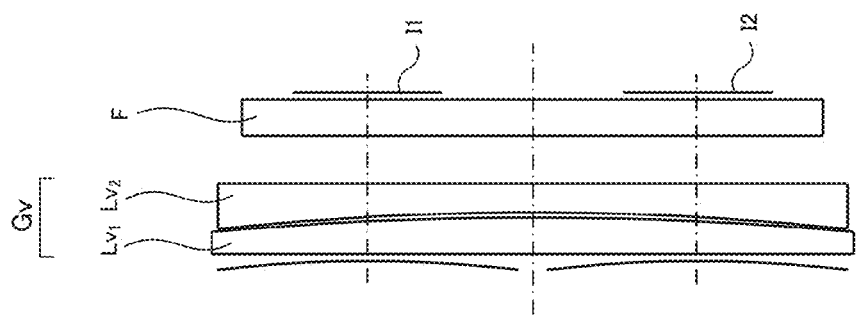
FIGS. 56A, 56B and 56C are illustrative of the variable optical system $G_V$ in Example 10 of the stereoscopic imaging optical system assembly 1.
Figure 56B:
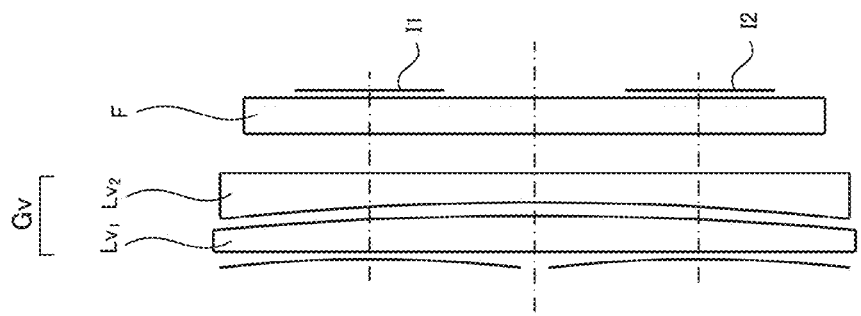
Figure 56C:
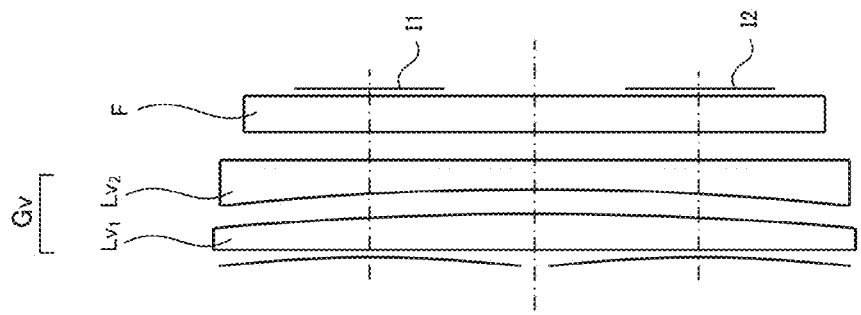
Figure 58:
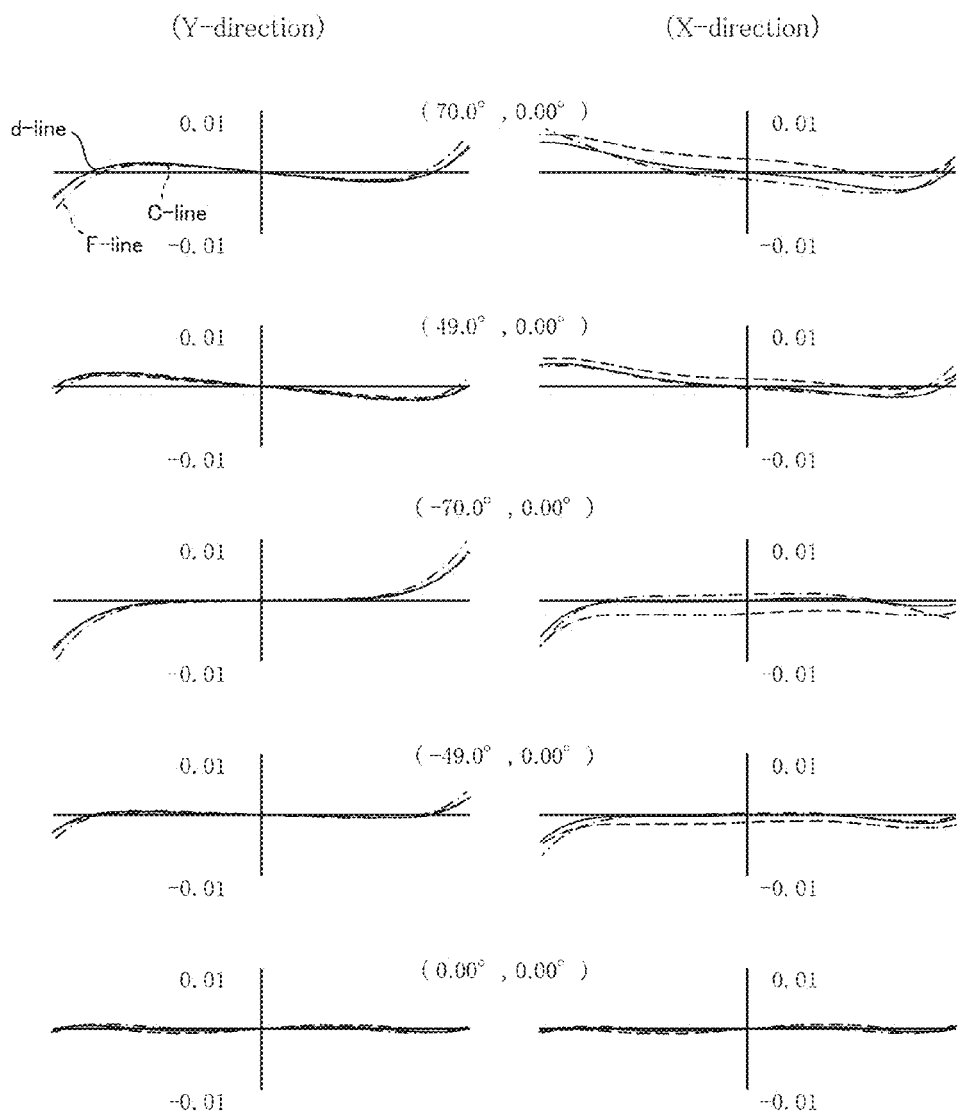
FIG. 58 is an aberration diagram in an intermediate state for Example 10 of the stereoscopic imaging optical system assembly 1.
Figure 59:
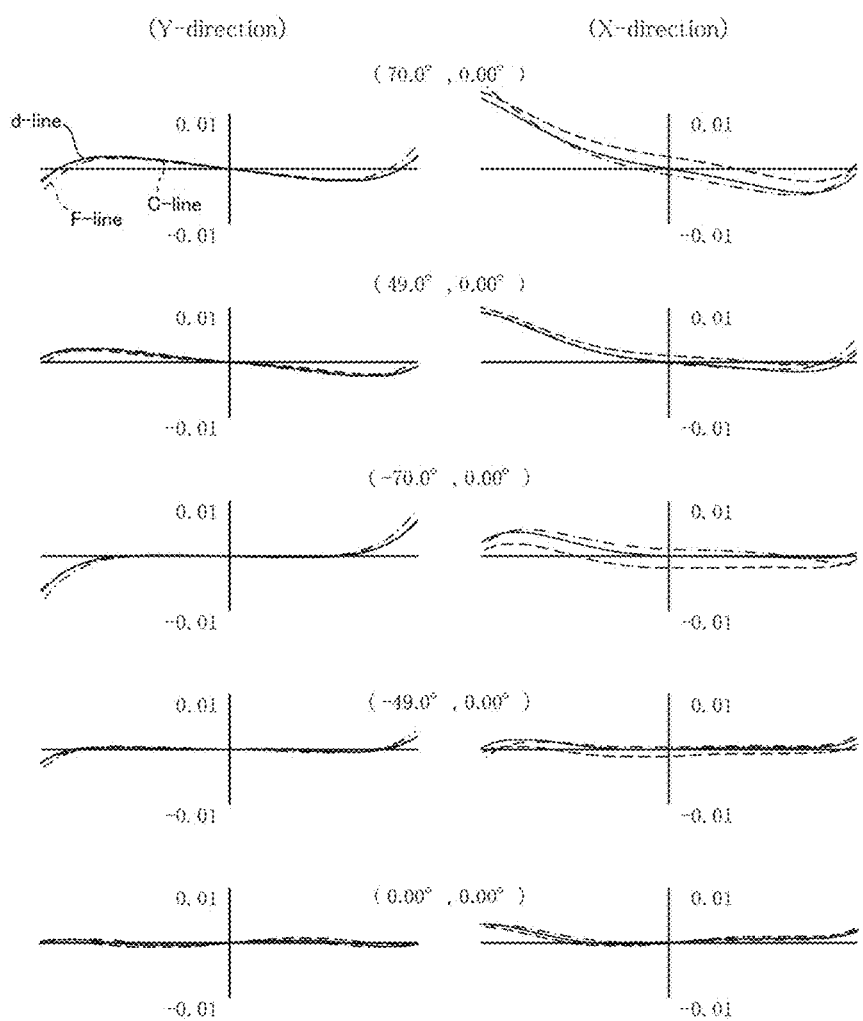
FIG. 59 is an aberration diagram at a near point for Example 10 of the stereoscopic imaging optical system assembly 1.
Figure 60:
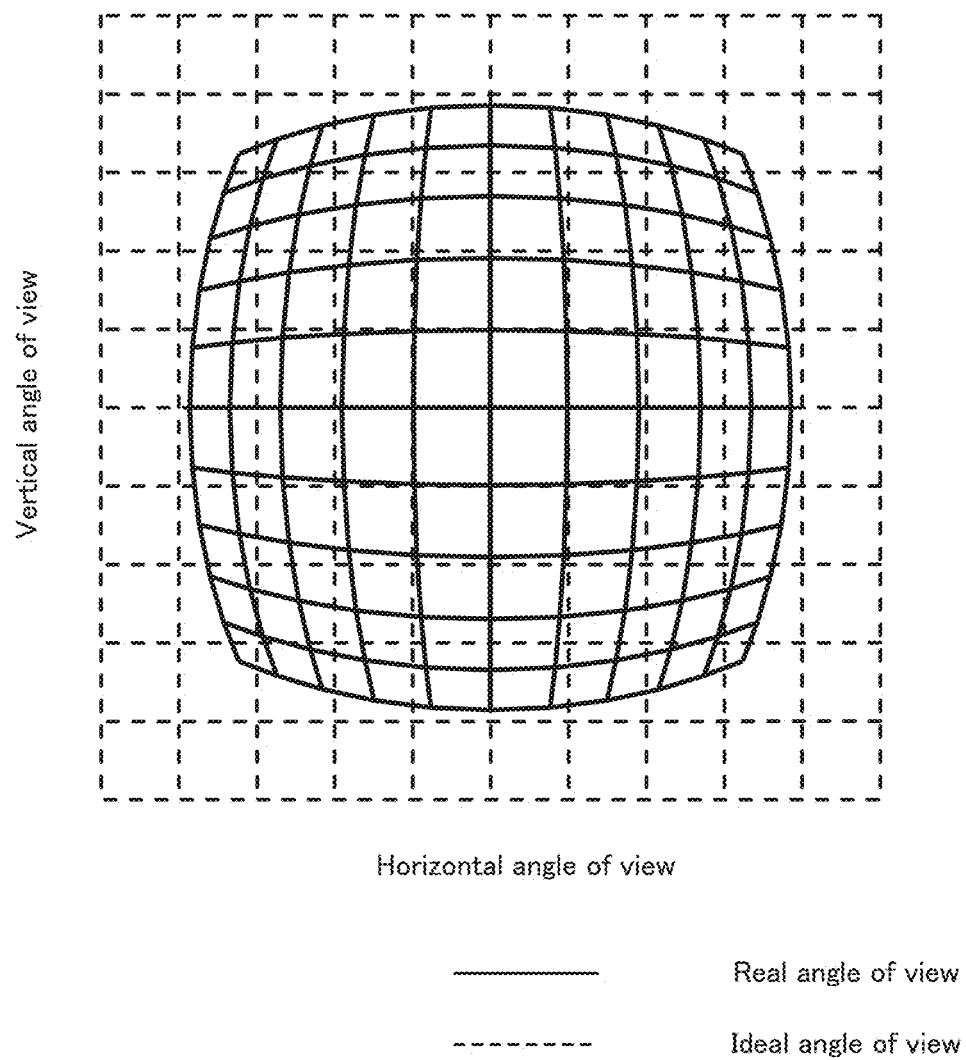
FIG. 60 is illustrative of image distortion in Example 10 of the stereoscopic imaging optical system assembly 1.

FIG. 55 is a sectional view of Example 10 of the stereoscopic imaging optical system assembly 1, as taken along the center axis C, and FIGS. 56A, 56B and 56C are sectional views of the variable optical system $G_V$ in Example 10, as taken along the center axis C. FIG. 57 is a transverse aberration diagram at a far point for Example 10 of the stereoscopic imaging optical system assembly 1, and FIG. 58 is a transverse aberration diagram at a near point for Example 10 of the stereoscopic imaging optical system assembly 1. FIG. 59 is a transverse aberration diagram at a near point for Example 10 of the stereoscopic imaging optical assembly 1, and FIG. 60 is illustrative of image distortion in Example 10 of the stereoscopic imaging optical system assembly 1.

As shown in FIG. 55, Example 10 of the stereoscopic imaging optical system assembly 1 includes, in order from the object side to the image plane side, a first optical system G1 comprising a first front group Gf1, a first stop S1 and a first rear group Gb1 with the first center axis C1 as an optical axis, a second optical system Gb2 comprising a second front group Gf2, a second stop S2 and a second rear group Gb2 with the second center axis C2 located in parallel with the first center axis C1 as an optical axis, and a variable optical system $G_V$ having a single center axis C.

In the stereoscopic imaging optical system assembly 1, parallel arrangement of the first G1 and the second optical system G2 makes stereoscopic observations possible.

The first front group Gf1 of the first optical system G1 includes, in order from the object side to the image plane side, a planoconcave negative lens $Lf1_1$ that is planar on the object side, a first front-group first cemented lens $SUf1_1$ consisting of a negative meniscus lens $Lf1_2$ convex on the object side and a double-convex positive lens $Lf1_3$, a positive meniscus lens $Lf1_4$ convex on the object lens, and a first front-group second cemented lens $SUf1_2$ consisting of a double-convex positive lens $Lf1_5$ and a double-concave negative lens $Lf1_6$.

The first rear group Gb1 of the first optical system G1 includes a positive meniscus lens $Lb1_1$ convex on the image plane side, a first rear-group cemented lens $SUb1_1$ consisting of a negative meniscus lens $Lb1_2$ convex on the object side and a double-convex positive lens $Lb1_3$, and a double-convex positive lens $Lb1_4$.

The second front group Gf2 of the second optical system G2 includes, in order from the object side to the image plane side, a planoconcave negative lens $Lf2_1$ that is planar on the object side, a second front-group first cemented lens $SUf2_1$ consisting of a negative meniscus lens $Lf2_2$ convex on the object side and a double-convex positive lens $Lf2_3$, a positive meniscus lens $Lf2_4$ convex on the object side, and a second front-group second cemented lens $SUf2_2$ consisting of a double-convex positive lens $Lf2_5$ and a double-concave negative lens $Lf2_6$.

The second rear group Gb2 of the second optical system G2 includes a positive meniscus lens $Lb2_1$ convex on the image plane side, a second rear-group cemented lens $SUb2_1$ consisting of a negative meniscus lens $Lb2_2$ convex on the object side and a double-convex positive lens $Lb2_3$, and a double-convex positive lens $Lb2_4$.

The variable optical system GV includes, in order from the object side to the image plane side, a plano-convex positive lens $L_{V1}$ that is planar on the object side, and a planoconcave negative lens $L_{V2}$ that is planar on the image plane side. The planoconcave negative lens $L_{V2}$ forms a variable optical element.

There is a filter F located in front of the first and second image planes $I_1$ and $I_2$.

A first light beam L1 incident on the first front group Gf1 from the first object plane (not shown) passes through the double-concave negative lens $Lf1_1$, first front-group first cemented lens $SUf1_1$, positive meniscus lens $Lf1_4$, first front-group second cemented lens $SUf1_2$, first aperture S1, positive meniscus lens $Lb1_1$, first rear-group cemented lens $SUb1_1$ and double-convex positive lens $Lb1_4$ and exits out of the first rear group Gb1. Then, the light beam enters the variable optical system $G_V$, passes through the planoconvex positive lens $L_{V1}$ and planoconcave negative lens $L_{V2}$ and exits out of the variable optical system $G_V$, entering the first image plane $I_1$ through the filter F.

A second light beam L2 incident on the second front group Gf2 from the second object plane (not shown) passes through the double-concave negative lens $Lf2_1$, second front-group first cemented lens $SUf2_1$, positive meniscus lens $Lf2_4$, second front-group second cemented lens $SUf2_2$, second aperture S2, positive meniscus lens $Lb2_1$, second rear-group cemented lens $SUb2_1$ and double-convex positive lens $Lb2_4$ and exits out of the second rear group Gb2. Then, the light beam enters the variable optical system $G_V$, passes through the planoconvex positive lens $L_{V1}$ and planoconcave negative lens $L_{V2}$ and exits out of the variable optical system $G_V$, entering the second image plane $I_2$ through the filter F.

Figure 61A:
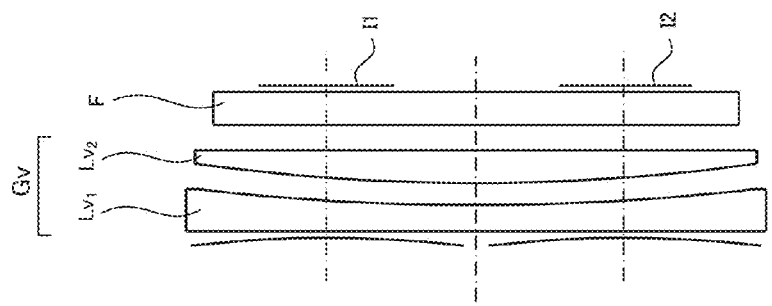
FIGS. 61A, 61B and 61C are illustrative of the variable optical system $G_V$ in Example 11 of the stereoscopic imaging optical system assembly 1.
Figure 61B:
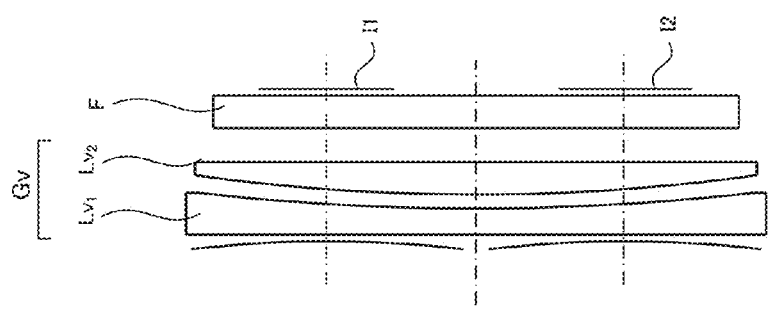
Figure 61C:
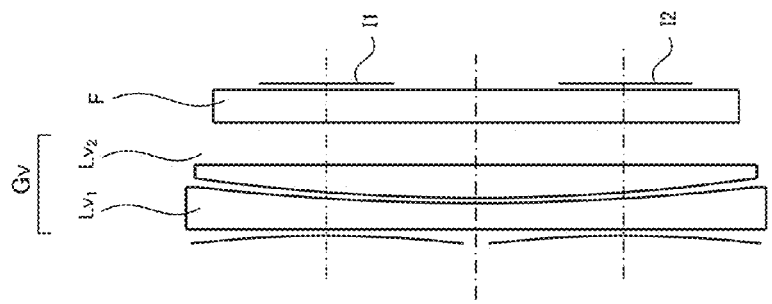
Figure 62:
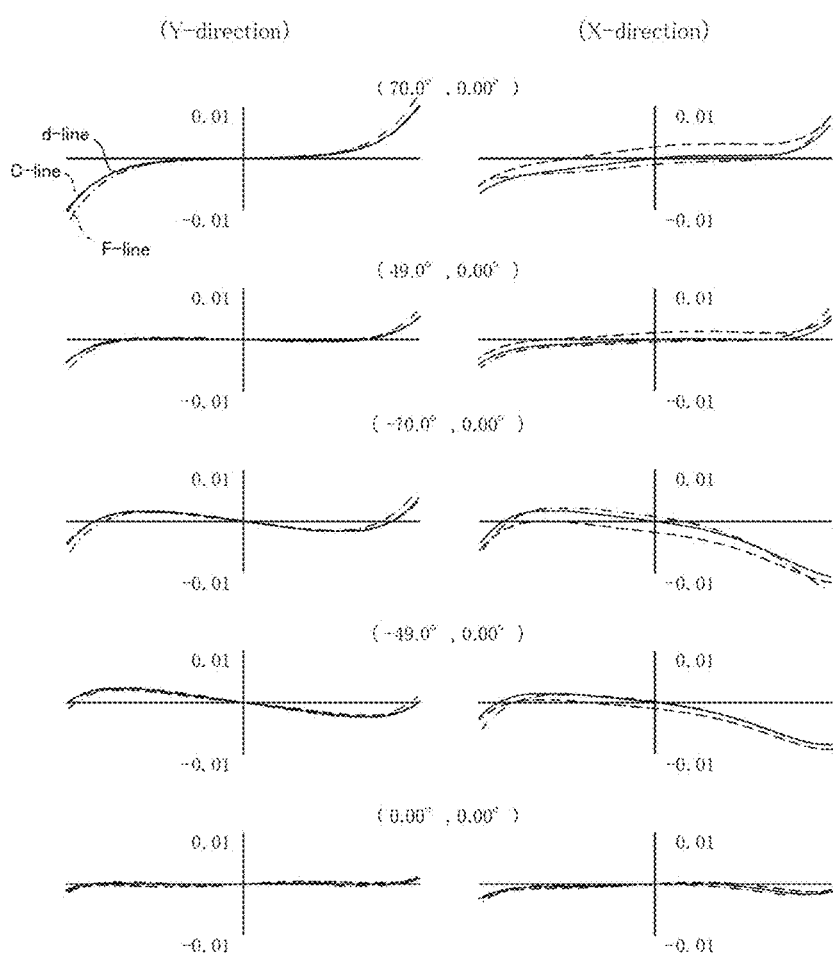
FIG. 62 is an aberration diagram at a far point for Example 11 of the stereoscopic imaging optical system assembly 1.
Figure 63:
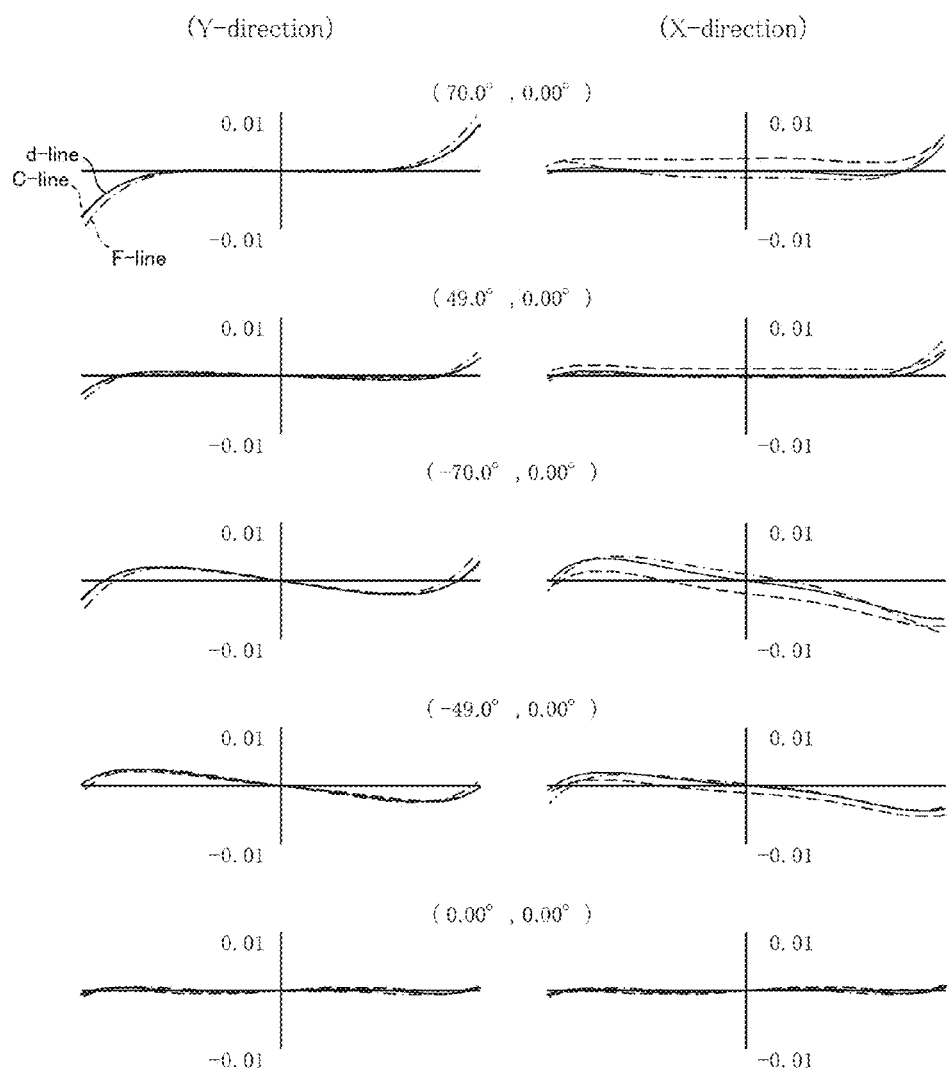
FIG. 63 is an aberration diagram in an intermediate state for Example 11 of the stereoscopic imaging optical system assembly 1.
Figure 64:
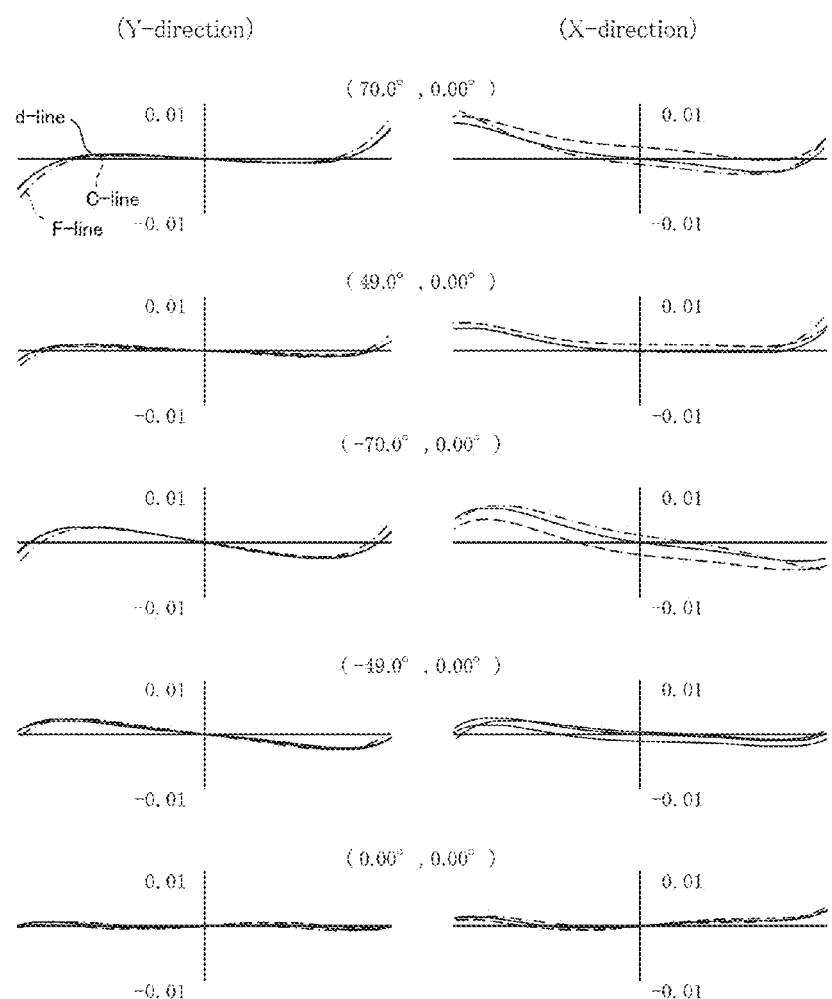
FIG. 64 is an aberration diagram at a near point for Example 11 of the stereoscopic imaging optical system assembly 1.
Figure 65:
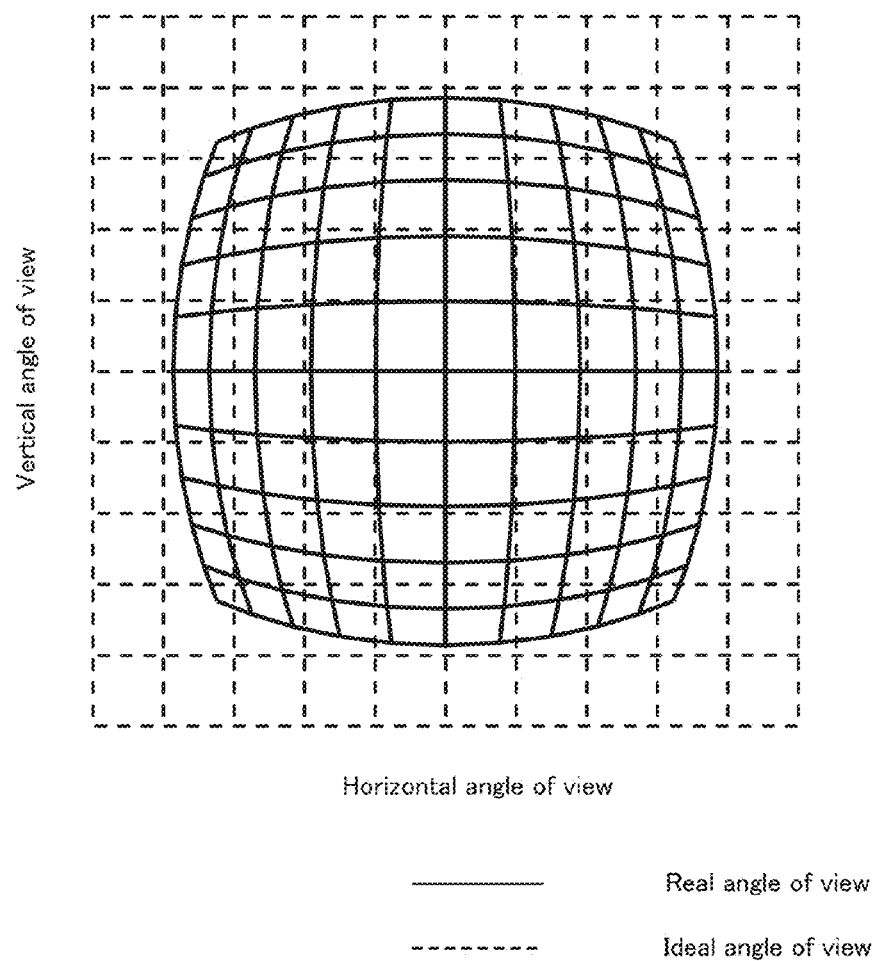
FIG. 65 is illustrative of image distortion in Example 11 of the stereoscopic imaging optical system assembly 1.

FIGS. 61A, 61B and 61C are sectional views of the variable optical system $G_V$ of Example 11, as taken along the center axis C. FIG. 62 is a transverse aberration diagram at a far point for Example 11 of the stereoscopic imaging optical system assembly 1. FIG. 63 is a transverse aberration diagram in an intermediate state for Example 11 of the stereoscopic imaging optical system assembly 1, and FIG. 64 is a transverse aberration diagram at a near point for Example 11 of the stereoscopic imaging optical system assembly 1. FIG. 65 is representative of image distortion in Example 11 of the stereoscopic imaging optical system assembly 1.

In Example 11 of the stereoscopic imaging optical system assembly 1, the variable optical system $G_V$ used in Example 10 of the stereoscopic imaging optical system assembly 1 shown in FIG. 15 is modified. Therefore, only the variable optical system $G_V$ is here explained.

The variable optical system $G_V$ used in Example 11 includes, in order from the object side to the image plane side, a planoconcave negative lens $L_{V1}$ that is planar on the object side and a planoconvex positive lens $L_{V2}$ that is planar on the image plane side. The planoconvex positive lens $L_{V2}$ forms a variable optical element.

A first light beam L1 incident on the first front group Gf1 from the first object plane (not shown) passes through the double-concave negative lens $Lf1_1$, first front-group first cemented lens $SUf1_1$, positive meniscus lens $Lf1_4$, first front-group second cemented lens $SUf1_2$, first aperture S1, positive meniscus lens $Lb1_1$, first rear-group cemented lens $SUb1_1$ and double-convex positive lens $Lb1_4$ and exits out of the first rear group Gb1. Then, the light beam enters the variable optical system $G_V$ and passes through the planoconcave negative lens $L_{V1}$ and planoconvex positive lens $L_{V2}$ and exits out of the variable optical system $G_V$, entering the first image plane $I_1$ through the filter F.

A second light beam L2 incident on the second front group Gf2 from the second object plane (not shown) passes through the double-concave negative lens $Lf2_1$, second front-group first cemented lens $SUf2_1$, positive meniscus lens $Lf2_4$, second front-group second cemented lens $SUf2_2$, second aperture S2, positive meniscus lens $Lb2_1$, second rear-group cemented lens $SUb2_1$ and double-convex positive lens $Lb2_4$ and exits out of the second rear group Gb2. Then, the light beam enters the variable optical system $G_V$, passes through the planoconcave negative lens $L_{V1}$ and planoconvex positive lens $L_{V2}$ and exits out of the variable optical system $G_V$, entering the second image plane $I_2$ through the filter F.

Figure 66C:
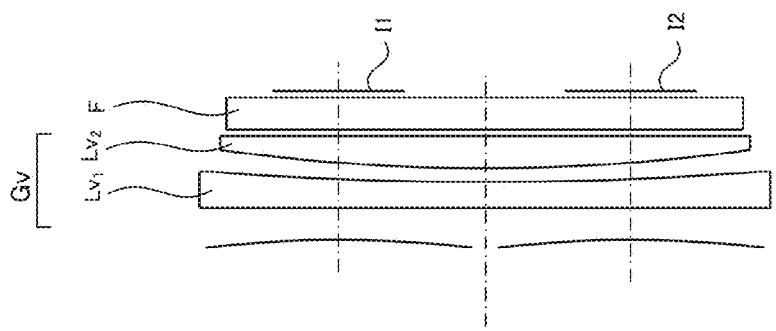
FIGS. 66A, 66B and 66C are illustrative of the variable optical system $G_V$ in Example 12 of the stereoscopic imaging optical system assembly 1.
Figure 66B:
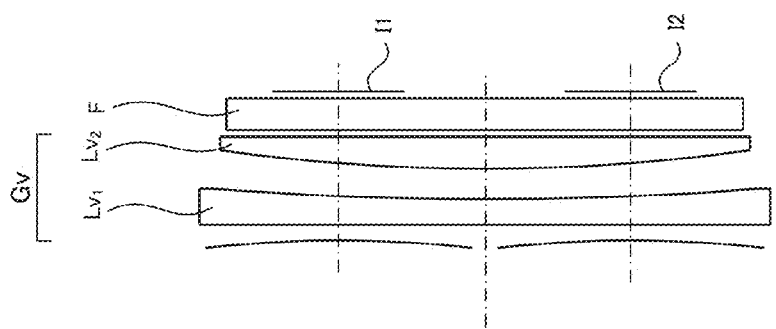
Figure 66A:
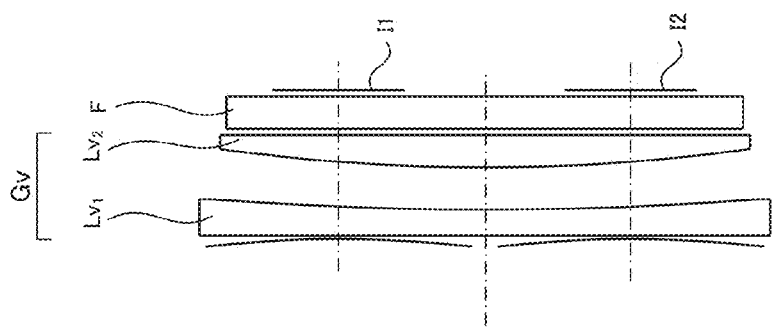
Figure 70:
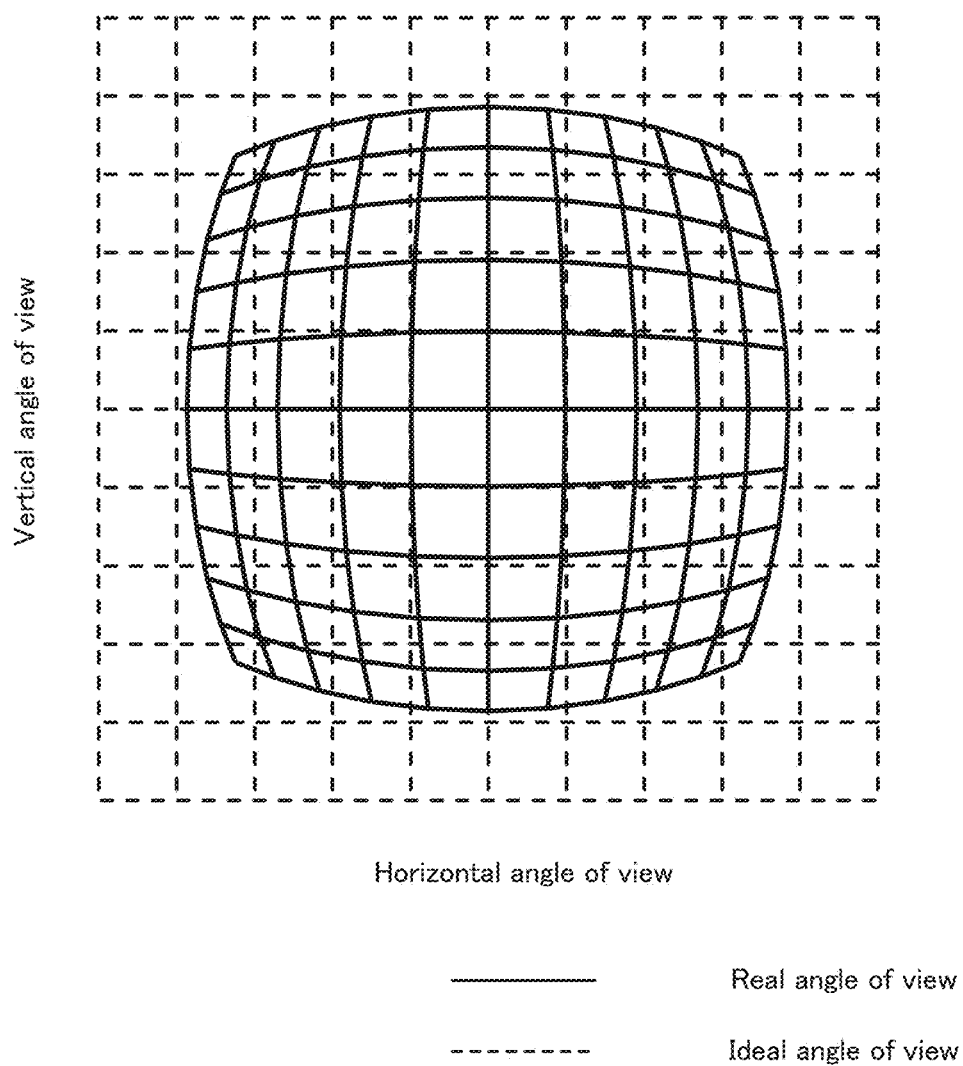
FIG. 70 is illustrative of image distortion in Example 12 of the stereoscopic imaging optical system assembly 1.

FIGS. 66A, 66B and 66C are sectional views of the variable optical system $G_V$ in Example 12, as taken along the center axis C. FIG. 67 is a transverse aberration diagram at a far point for Example 12 of the stereoscopic imaging optical system assembly 1. FIG. 68 is a transverse aberration diagram in an intermediate state for Example 12 of the stereoscopic imaging optical system assembly 1, and FIG. 69 is a transverse aberration diagram at a near point for Example 12 of the stereoscopic imaging optical system assembly 1. FIG. 70 is representative of image distortion in Example 12 of the stereoscopic imaging optical system assembly 1.

In Example 12 of the stereoscopic imaging optical system assembly 1, the variable optical system $G_V$ used in Example 11 of the stereoscopic imaging optical system assembly 1 shown in FIGS. 61A, 61B and 61C is modified. Therefore, only the variable optical system $G_V$ is here explained.

The variable optical system $G_V$ used in Example 12 includes, in order from the object side to the image plane side, a planoconcave negative lens $L_{V1}$ that is planar on the object side and a planoconvex positive lens $L_{V2}$ that is planar on the image plane side. The planoconcave negative lens $L_{V1}$ forms a variable optical element.

A first light beam L1 incident on the first front group Gf1 from the first object plane (not shown) passes through the double-concave negative lens $Lf1_1$, first front-group first cemented lens $SUf1_1$, positive meniscus lens $Lf1_4$, first front-group second cemented lens $SUf1_2$, first aperture S1, positive meniscus lens $Lb1_1$, first rear-group cemented lens $SUb1_1$ and double-convex positive lens $Lb1_4$ and exits out of the first lens group Gb1. Then, the light beam enters the variable optical system $G_V$, passes through the planoconcave negative lens $L_{V1}$ and planoconvex positive lens $L_{V2}$ and emits out of the variable optical system $G_V$, entering the first image plane $I_1$ through the filter F.

A second light beam L2 incident on the second front group Gf2 from the second object plane (not shown) passes through the double-concave negative lens $Lf2_1$, second front-group first cemented lens $SUf2_1$, positive meniscus lens $Lf2_4$, second front-group second cemented lens $SUf2_2$, second aperture S2, positive meniscus lens $Lb2_1$, second rear-group cemented lens $SUb2_1$ and double-convex positive lens $Lb2_4$ and exits out of the second rear group Gb2. Then, the light beam enters the variable optical system $G_V$, passes through the planoconcave negative lens $L_{V1}$ and planoconvex positive lens $L_{V2}$ and exits out of the variable optical system $G_V$, entering the second image plane $I_2$ through the filter F.

Figure 71C:
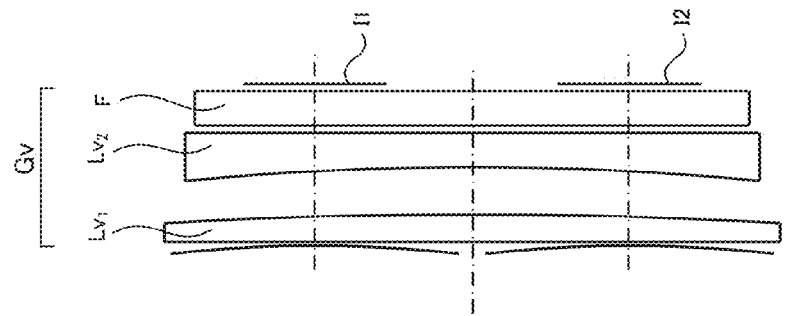
FIGS. 71A, 71B and 71C are illustrative of the variable optical system $G_V$ in Example 13 of the stereoscopic imaging optical system assembly 1.
Figure 71B:
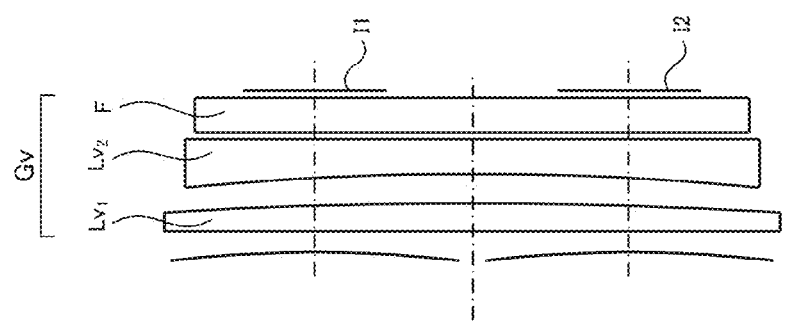
Figure 71A:
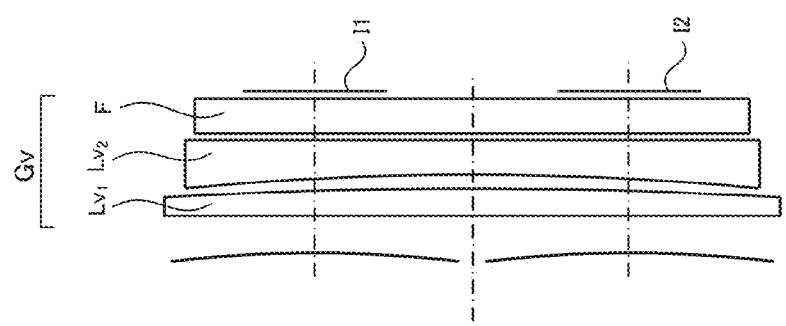
Figure 75:
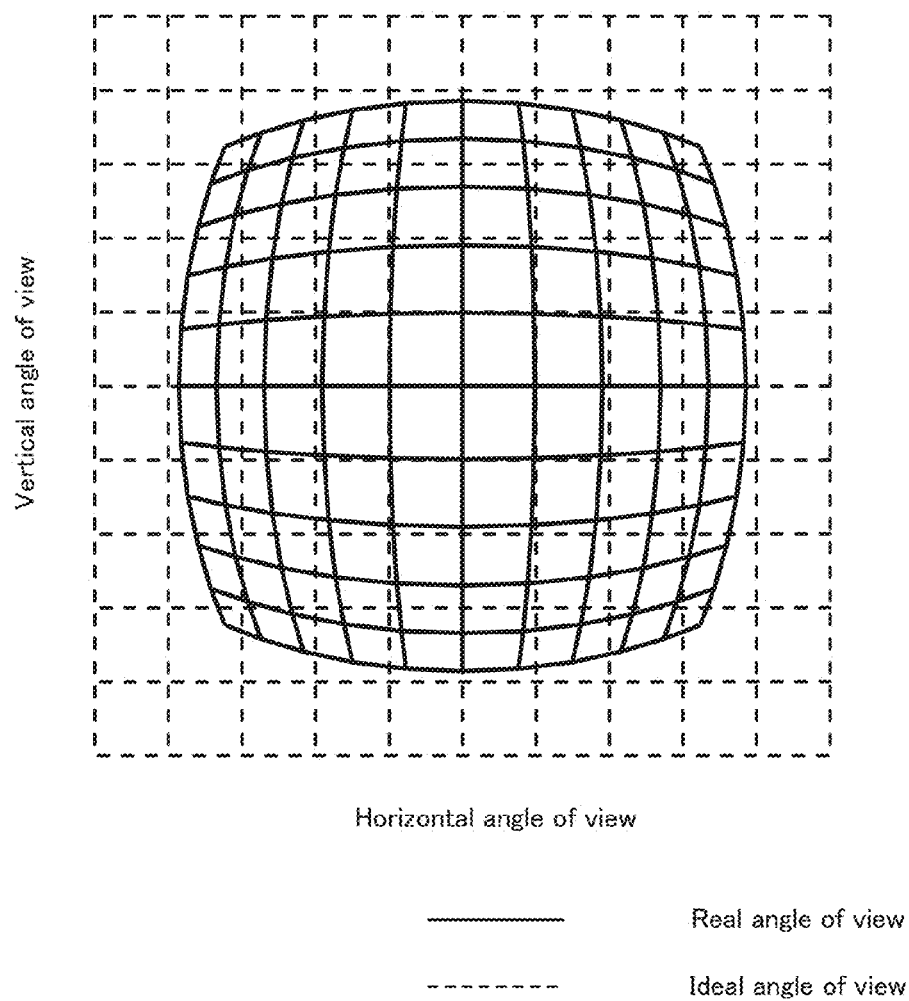
FIG. 75 is illustrative of image distortion in Example 13 of the stereoscopic imaging optical system assembly 1.

FIGS. 71A, 71B and 71C are sectional views of the variable optical system $G_V$ in Example 13, as taken along the center axis C. FIG. 72 is a transverse aberration diagram at a far point for Example 13 of the stereoscopic imaging optical system assembly 1. FIG. 73 is a transverse aberration diagram in an intermediate state for Example 13 of the stereoscopic imaging optical system assembly 1, and FIG. 74 is a transverse aberration diagram at a near point for Example 13 of the stereoscopic imaging optical system assembly 1. FIG. 75 is representative of image distortion in Example 13 of the stereoscopic imaging optical system assembly 1.

In Example 13 of the stereoscopic imaging optical system assembly 1, the variable optical system $G_V$ used in Example 12 of the stereoscopic imaging optical system assembly 1 shown in FIGS. 66A, 66B and 66C is modified. Therefore, only the variable optical system $G_V$ is here explained.

The variable optical system $G_V$ used in Example 13 includes, in order from the object side to the image plane side, a planoconvex positive lens $L_{V1}$ that is planar on the object side and a planoconcave negative lens $L_{V2}$ that is planar on the image plane side. The planoconvex positive lens $L_{V1}$ forms a variable optical element.

A first light beam L1 incident on the first front group Gf1 from the first object plane (not shown) passes through the double-concave negative lens $Lf1_1$, first front-group first cemented lens $SUf1_1$, positive meniscus lens $Lf1_4$, first front-group second cemented lens $SUf1_2$, first aperture S1, positive meniscus lens $Lb1_1$, first rear-group cemented lens $SUb1_1$ lens and double-convex positive lens $Lb1_4$ and exits out of the first rear group Gb1. Then, the light beam enters the variable optical system $G_V$, passes through the planoconvex positive lens $L_{V1}$ and planoconcave negative lens $L_{V2}$ and exits out of the variable optical system $G_V$, entering the first image plane $I_1$ through the filter F.

A second light beam L2 incident on the second front group Gf2 from the second object plane (not shown) passes through the double-concave negative lens $Lf2_1$, second front-group first cemented lens $SUf2_1$, positive meniscus lens $Lf2_4$, second front-group second cemented lens $SUf2_2$, second aperture S2, positive meniscus lens $Lb2_1$, second rear-group cemented lens $SUb2_1$ and double-convex positive lens $Lb2_4$ and exits out of the second rear group Gb2. Then, the light beam enters the variable optical system $G_V$, passes through the planoconvex positive lens $L_{V1}$ and planoconcave negative lens $L_{V2}$ and exits out of the variable optical system $G_V$, entering the second image plane $I_2$ through the filter F.

Figure 77C:
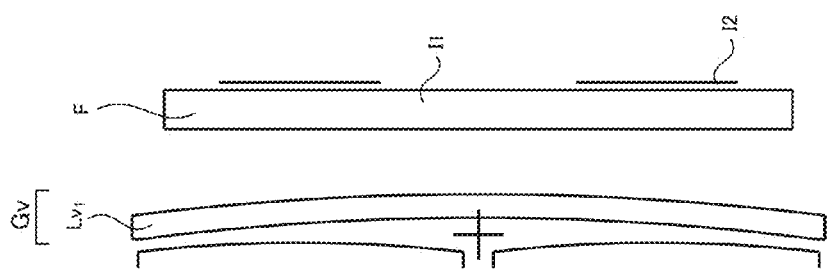
FIGS. 77A, 77B and 77C are illustrative of the variable optical system $G_V$ in Example 14, as taken along its center axis C.
Figure 77B:
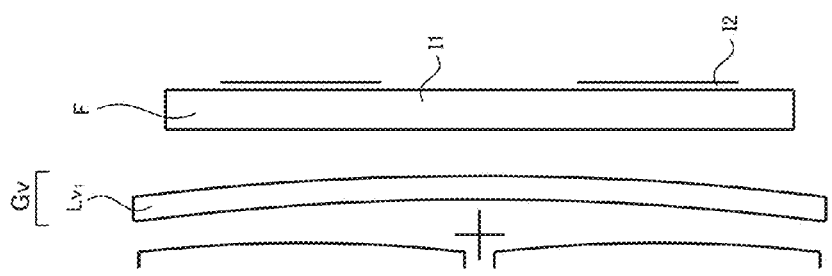
Figure 77A:
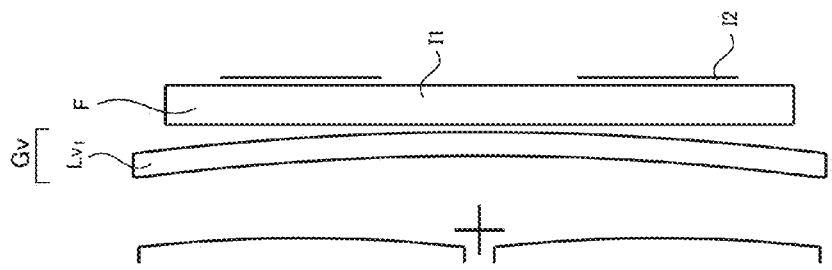
Figure 81:
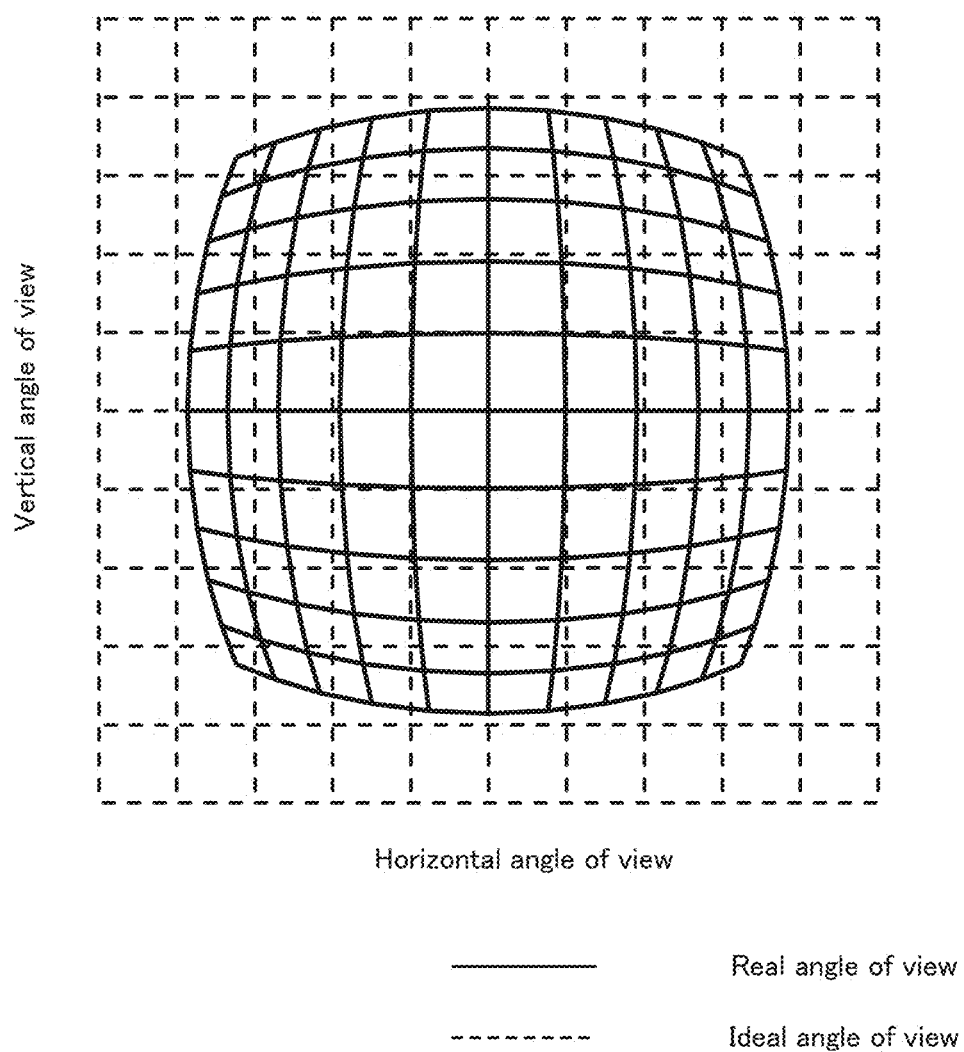
FIG. 81 is illustrative of image distortion in Example 14 of the stereoscopic imaging optical system assembly 1.

FIG. 76 is a sectional view of Example 14 of the stereoscopic imaging optical system assembly 1, and FIGS. 77A, 77B and 77C are sectional views of the variable optical system $G_V$ in Example 14, as taken along the center axis C. FIG. 78 is a transverse aberration diagram at a far point for Example 14 of the stereoscopic imaging optical system assembly 1. FIG. 79 is a transverse aberration diagram in an intermediate state for Example 14 of the stereoscopic imaging optical system assembly 1, and FIG. 80 is a transverse aberration diagram at a near point for Example 14 of the stereoscopic imaging optical system assembly 1. FIG. 81 is representative of image distortion in Example 14 of the stereoscopic imaging optical system assembly 1.

In Example 14 of the stereoscopic imaging optical system assembly 1, the variable optical system $G_V$ used in Example 13 of the stereoscopic imaging optical system assembly 1 shown in FIGS. 71A, 71B and 71C is modified. Therefore, only the variable optical system $G_V$ is here explained.

The variable optical system $G_V$ used in Example 14 includes, in order from the object side to the image plane side, a negative meniscus lens $L_{V1}$ that is concave on the object side. The negative meniscus lens $L_{V1}$ forms a variable optical element.

A first light beam L1 incident on the first front group Gf1 from the first object plane (not shown) passes through the double-concave negative lens $Lf1_1$, first front-group first cemented lens $SUf1_1$, positive meniscus lens $Lf1_4$, first front-group second cemented lens $SUf1_2$, first aperture S1, positive meniscus lens $Lb1_1$, first rear-group cemented lens $SUb1_1$ and double-convex positive lens $Lb1_4$ and exits out of the first rear group Gb1. Then, the light beam enters the variable optical system $G_V$, passes through the negative meniscus lens $L_{V1}$ and exits out of the variable optical system $G_V$, entering the first image plane $I_1$ through the filter F.

A second light beam L2 incident on the second front group Gf2 from the second object plane (not shown) passes through the double-concave negative lens $Lf2_1$, second front-group first cemented lens $SUf2_1$, positive meniscus lens $Lf2_4$, second front-group second cemented lens $SUf2_2$, second aperture S2, positive meniscus lens $Lb2_1$, second rear-group cemented lens $SUb2_1$ and double-convex positive lens $Lb2_4$ and exits out of the second rear group Gb2. Then, the light beam enters the variable optical system $G_V$, passes through the negative meniscus lens $L_{V1}$ and exits out of the variable optical system $G_V$, entering the second image plane $I_2$ through the filter F.

In what follows, constituting parameters of the examples will be given.

Of the optical surfaces forming the optical systems in each example, a specific surface and the subsequent surface are given a surface separation when they form together a coaxial optical system. The radii of curvature of surfaces, the refractive index and Abbe constant of a medium, etc. are given as conventional.

Given to each decentered surface are the amount of decentration of the coordinate system—on which that surface is defined—from the origin O (X, Y and Z in the X-, Y- and Z-axis directions) and the angles ($\alpha$, $\beta$, $\gamma$ (°)) of tilt of the coordinate system for defining each surface with the X-, Y- and Z-axes of the coordinate system defined on the origin as center. Then, the positive $\alpha$ and $\beta$ mean counterclockwise rotation with respect to the positive directions of the respective axes, and the positive $\gamma$ means clockwise rotation with respect to the positive direction of the Z-axis. Referring here to the $\alpha$, $\beta$, $\gamma$ rotation of the center axis of a certain surface, the coordinate system for defining each surface is first $\alpha$ rotated counterclockwise about the X-axis of the coordinate system defined on the origin of an optical system. Then, the center axis of the rotated surface is $\beta$ rotated counterclockwise about the Y-axis of a new coordinate system. Finally, the center axis is $\gamma$ rotated clockwise about the Z-axis of a rotated new coordinate system.

Refractive indices and Abbe constants on d-line (wavelength: 587.56 nm) basis are given, and length is given in mm. The decentration of each surface is expressed by the amount of decentration from the reference surface as described above. The symbol "∞" affixed to the radius of curvature is indicative of infinity, and * is affixed to surface separation changes.

Aspheric data include data about aspheric lens surfaces. Aspheric surface shape or configuration may be represented by $$Z=(y^2/r)/[1+\{1-(1+K)\cdot(y/r)^2\}^{1/2}]+i\,ay^4+by^6+cy^8+dy^{10}\cdots$$

In the aforesaid formula, r is a paraxial radius of curvature, K is a conic coefficient, and A4, A6 and A8 are the $4^{th}$, $6^{th}$ and $8^{th}$ order aspheric coefficients, respectively. Note here that the symbol "e" indicates that the subsequent numerical value is a power exponent having 10 as a base. For instance, "1.0e-5" means "$1.0\times10^{-5}$".

The surface shape of the free-form surface FFS used in the embodiments of the invention is defined by the following formula (a). Note here that the Z-axis of that defining formula is the axis of the free-form surface, and that a coefficient term with no data described is zero.

$$Z = (r^2/R)/\left[1 + \sqrt{\{1-(1+k)(r/R^2)\}}\right] + \sum_{j=1}^{66} C_j X^m Y^n \quad (a)$$

Here the first terms of Formula (a) is the spherical term, and the second term is the free-form surface term.

In the spherical term,
R is the radius of curvature of the apex,
k is the conic constant, and
r is $\sqrt{(X^2+Y^2)}$.
The free-form surface term is:

$$\sum_{j=1}^{66} C_j X^m Y^n =$$
$$C_1 + C_2 X + C_3 Y + C_4 X^2 + C_5 XY + C_6 Y^2 + C_7 X^3 + C_8 X^2 Y +$$
$$C_{10} Y^3 + C_{11} X^4 + C_{12} X^3 Y + C_{13} X^2 Y^2 + C_{14} XY^3 + C_{15} Y^4 +$$
$$C_{16} X^5 + C_{17} X^4 Y + C_{18} X^3 Y^2 + C_{19} X^2 Y^3 + C_{20} XY^4 + C_{21} Y^5 +$$
$$C_{22} X^6 + C_{23} X^6 + C_{23} X^5 Y + C_{24} X^4 Y^2 + C_{25} X^3 Y^3 + C_{26} X^2 Y^4 +$$
$$C_{27} XY^5 + C_{28} Y^6 + C_{29} X^7 + C_{30} X^6 Y + C_{31} X^5 Y^2 +$$
$$C_{32} X^4 Y^3 + C_{33} X^3 Y^4 + C_{34} X^2 Y^5 + C_{35} XY^6 + C_{36} Y^7$$

where $C_j$ (j is an integer of 1 or greater) is a coefficient.

Example 1

| Surface No. | Radius of curvature | Surface separation | Decentration |
|---|---|---|---|
| Object plane | ∞ | 50.000 | |
| 1 | Aspheric surface [1] | 0.500 | |
| 2 | Aspheric surface [2] | 0.383 | |
| 3 | −10.595 | 0.750 | |
| 4 | −2.377 | 4.782 | |
| 5 | Stop plane | 0.125 | |
| 6 | −15.941 | 0.375 | |
| 7 | 1.546 | 0.750 | |
| 8 | −4.136 | 0.063 | |
| 9 | 3.390 | 0.625 | |
| 10 | 336.258 | 1.875 | |
| 11 | ∞ | 0.000 | Decentration (1) |
| 12 | ∞ | 0.710 | Decentration (2) |
| 13 | ∞ | 0.065 | |
| 14 | ∞ | 0.500 | |
| 15 | ∞ | 0.050 | |
| Image plane | ∞ | | |

| Surface No. | Refractive index | Abbe constant |
|---|---|---|
| Object plane | | |
| 1 | 1.8830 | 40.7 |
| 2 | | |
| 3 | 1.9229 | 18.9 |
| 4 | | |
| 5 | | |
| 6 | 1.9229 | 18.9 |
| 7 | 1.8830 | 40.7 |
| 8 | | |
| 9 | 1.9229 | 18.9 |
| 10 | | |
| 11 | | |
| 12 | 1.8830 | 40.7 |
| 13 | | |
| 14 | 1.5163 | 64.1 |
| 15 | | |
| Image plane | | |

Aspheric surface [1]

| | | | | |
|---|---|---|---|---|
| Radius of curvature | | −1.516 | | |
| k | 0.0000e+000 | | | |
| a | 1.9351e−001 | b | −2.7113e−002 | |

Aspheric surface [2]

| | | | | |
|---|---|---|---|---|
| Radius of curvature | | 4.199 | | |
| k | 1.1576e+001 | | | |
| a | 4.2146e−002 | b | 1.0304e−001 | c | −8.9984e−002 |

Decentration [1]

| X | 1.500 | Y | 0.000 | Z | 0.000 |
|---|---|---|---|---|---|
| α | 0.000 | β | 0.000 | γ | 0.000 |

Decentration [2]

| X | 0.000 | Y | 0.000 | Z | 0.000 |
|---|---|---|---|---|---|
| α | 2.467 | β | 0.000 | γ | 0.000 |

Specifications

| | |
|---|---|
| Angle of view | 90° |
| Focal length | 0.915 |
| Stop diameter | φ 1.250 mm |
| Image size | φ 1.000 |
| Effective Fno | 2.171 |

Example 2

Example 2 is the same as Example 1.

Example 3

Example 3 is the same as Example 1.

Example 4

| Surface No. | Radius of curvature | Surface separation | Decentration |
|---|---|---|---|
| Object plane | ∞ | 50.000 | |
| 1 | Aspheric surface [1] | 0.500 | |
| 2 | Aspheric surface [2] | 0.383 | |
| 3 | −10.595 | 0.750 | |
| 4 | −2.377 | 4.782 | |
| 5 | Stop plane | 0.125 | |
| 6 | −15.941 | 0.375 | |
| 7 | 1.546 | 0.750 | |
| 8 | −4.136 | 0.063 | |
| 9 | 3.390 | 0.625 | |

-continued

| | | |
|---|---|---|
| 10 | 336.258 | 0.125 |
| 11 | ∞ | 0.000 | Decentration (1) |
| 12 | Slope surface | 0.820 |
| 13 | FFS[1] | 1.727 |
| 14 | ∞ | 0.500 |
| 15 | ∞ | 0.050 |
| Image plane | ∞ | |

| Surface No. | Refractive index | Abbe constant |
|---|---|---|
| Object plane | | |
| 1 | 1.8830 | 40.7 |
| 2 | | |
| 3 | 1.9229 | 18.9 |
| 4 | | |
| 5 | | |
| 6 | 1.9229 | 18.9 |
| 7 | 1.8830 | 40.7 |
| 8 | | |
| 9 | 1.9229 | 18.9 |
| 10 | | |
| 11 | | |
| 12 | 1.8830 | 40.7 |
| 13 | | |
| 14 | 1.5163 | 64.1 |
| 15 | | |
| Image plane | | |

Aspheric surface [1]

| | | | |
|---|---|---|---|
| Radius of curvature | | −1.516 | |
| k | 0.0000e+000 | | |
| a | 1.9351e−001 | b | −2.7113e−002 |

Aspheric surface [2]

| | | | | | |
|---|---|---|---|---|---|
| Radius of curvature | | 4.199 | | | |
| k | 1.1576e+001 | | | | |
| a | 4.2146e−002 | b | 1.0304e−001 | c | −8.9984e−002 |

FFS[1]

| | | | | | |
|---|---|---|---|---|---|
| C4 | 1.9534e−003 | C6 | −4.9348e−005 | C11 | −1.9028e−004 |
| C13 | −5.4524e−005 | C15 | 3.4418e−004 | C22 | 9.5229e−006 |
| C24 | 5.2482e−005 | C26 | −7.9299e−005 | C28 | −1.0146e−005 |
| C67 | 2.7000e+001 | | | | |

Decentration [1]

| | | | | | | | |
|---|---|---|---|---|---|---|---|
| X | 1.500 | Y | 0.000 | Z | 0.000 | | |
| α | 0.000 | β | 0.000 | γ | 0.000 | | |

Example 5

Example 5 is the same as Example 4.

Example 6

| Surface No. | Radius of curvature | Surface separation | Decentration |
|---|---|---|---|
| Object plane | ∞ | *1 33.000 | |
| 1 | ∞ | 0.400 | |
| 2 | Aspheric surface [1] | 2.445 | |
| 3 | 6.597 | 0.400 | |
| 4 | 1.473 | 0.800 | |
| 5 | −7.655 | 0.845 | |
| 6 | Stop plane | 0.100 | |
| 7 | 2.036 | 0.400 | |
| 8 | 0.746 | 0.800 | |
| 9 | −3.412 | 0.000 | |
| 10 | ∞ | *2 0.155 | Decentration (1) |
| 11 | −26.019 | 0.600 | |
| 12 | −10.000 | *3 0.256 | |
| 13 | −4.690 | 0.600 | |

-continued

| | | |
|---|---|---|
| 14 | −5.194 | 0.100 |
| 15 | ∞ | 1.000 |
| 16 | ∞ | 0.100 |
| Image plane | ∞ | |

| Surface No. | Refractive index | Abbe constant |
|---|---|---|
| Object plane | | |
| 1 | 1.8830 | 40.7 |
| 2 | | |
| 3 | 1.8040 | 46.6 |
| 4 | 1.8081 | 22.8 |
| 5 | | |
| 6 | | |
| 7 | 1.9229 | 18.9 |
| 8 | 1.8040 | 46.6 |
| 9 | | |
| 10 | | |
| 11 | 1.8830 | 40.7 |
| 12 | | |
| 13 | 1.9229 | 18.9 |
| 14 | | |
| 15 | 1.5163 | 64.1 |
| 16 | | |
| Image plane | | |

Aspheric surface [1]

| | | | |
|---|---|---|---|
| Radius of curvature | | | 0.611 |
| k | −6.7809e−001 | | |
| a | −1.1758e−001 | | |

Decentration [1]

| | | | | | | | |
|---|---|---|---|---|---|---|---|
| X | 1.00 | Y | 0.00 | Z | 0.00 | | |
| α | 0.00 | β | 0.00 | γ | 0.00 | | |
| *1 | 33.000 | | 16.000 | | 10.000 | | |
| *2 | 0.155 | | 0.129 | | 0.102 | | |
| *3 | 0.256 | | 0.282 | | 0.309 | | |

Specifications

| | |
|---|---|
| Angle of view | 140° |
| Focal length | 0.423 |
| Stop diameter | φ 0.900 mm |
| Image size | φ 1.000 |
| Effective Fno | 2.566 |

Example 7

| Surface No. | Radius of curvature | Surface separation | Decentration |
|---|---|---|---|
| Object plane | ∞ | *1 33.000 | |
| 1 | ∞ | 0.400 | |
| 2 | Aspheric surface [1] | 1.196 | |
| 3 | 5.944 | 0.600 | |
| 4 | −8.831 | 1.773 | |
| 5 | −1.584 | 0.400 | |
| 6 | 1.025 | 0.800 | |
| 7 | −1.316 | 0.100 | |
| 8 | Stop plane | 0.233 | |
| 9 | 3.699 | 0.400 | |
| 10 | 1.137 | 0.800 | |
| 11 | −2.440 | 0.000 | |
| 12 | ∞ | 0.150 | Decentration (1) |
| 13 | −10.480 | 0.400 | |
| 14 | 3.843 | 0.000 | |
| 15 | ∞ | *2 0.303 | |
| 16 | 3.644 | 1.200 | |
| 17 | −12.577 | *3 0.546 | |
| 18 | ∞ | 2.049 | |
| 19 | ∞ | 0.500 | |
| 20 | ∞ | 0.100 | |

| Image plane | ∞ | |
|---|---|---|
| Surface No. | Refractive index | Abbe constant |
| Object plane | | |
| 1 | 1.8830 | 40.7 |
| 2 | | |
| 3 | 1.9229 | 18.9 |
| 4 | | |
| 5 | 1.8830 | 40.7 |
| 6 | 1.6330 | 31.4 |
| 7 | | |
| 8 | | |
| 9 | 1.9229 | 18.9 |
| 10 | 1.8830 | 40.7 |
| 11 | | |
| 12 | | |
| 13 | 1.6938 | 36.2 |
| 14 | | |
| 15 | | |
| 16 | 1.8830 | 40.7 |
| 17 | | |
| 18 | | |
| 19 | 1.5163 | 64.1 |
| 20 | | |
| Image plane | | |

Aspheric surface [1]

| Radius of curvature | | 0.840 | |
|---|---|---|---|
| k | −1.0098e+000 | | |
| a | 2.3338e−002 | | |

Decentration [1]

| X | 1.000 | Y | 0.000 | Z | 0.000 |
|---|---|---|---|---|---|
| α | 0.000 | β | 0.000 | γ | 0.000 |
| *1 | 33.000 | | 10.000 | | 0.000 |
| *2 | 0.303 | | 0.291 | | 0.100 |
| *3 | 0.546 | | 0.558 | | 0.749 |

Specifications

| Angle of view | 140° |
|---|---|
| Focal length | 0.412 |
| Stop diameter | φ 1.000 mm |
| Image size | φ 1.000 |
| Effective Fno | 2.204 |

Example 8

| Surface No. | Radius of curvature | Surface separation | Decentration |
|---|---|---|---|
| Object plane | ∞ | *1 62.500 | |
| 1 | Aspheric surface [1] | 0.500 | |
| 2 | Aspheric surface [2] | 0.231 | |
| 3 | 3.513 | 0.750 | |
| 4 | −3.835 | 4.081 | |
| 5 | Stop plane | 0.125 | |
| 6 | −32.785 | 0.375 | |
| 7 | 1.650 | 0.750 | |
| 8 | −4.644 | 0.063 | |
| 9 | 3.688 | 0.625 | |
| 10 | −28.330 | 0.188 | |
| 11 | ∞ | 0.000 | Decentration (1) |
| 12 | −54.603 | 0.750 | |
| 13 | −71.025 | *2 0.125 | |
| 14 | 18.604 | 0.750 | |
| 15 | 6.554 | *3 0.755 | |
| 16 | 6.696 | 0.750 | |
| 17 | 20.976 | 0.152 | |
| 18 | ∞ | 0.500 | |
| 19 | ∞ | 0.050 | |

| 20 | ∞ | 0.000 |
|---|---|---|
| Image plane | ∞ | |

| Surface No. | Refractive index | Abbe constant |
|---|---|---|
| Object plane | | |
| 1 | 1.8830 | 40.7 |
| 2 | | |
| 3 | 1.9229 | 18.9 |
| 4 | | |
| 5 | | |
| 6 | 1.9229 | 18.9 |
| 7 | 1.8830 | 40.7 |
| 8 | | |
| 9 | 1.9229 | 18.9 |
| 10 | | |
| 11 | | |
| 12 | 1.9229 | 18.9 |
| 13 | | |
| 14 | 1.6180 | 63.3 |
| 15 | | |
| 16 | 1.8830 | 40.7 |
| 17 | | |
| 18 | 1.5163 | 64.1 |
| 19 | | |
| 20 | | |
| Image plane | | |

Aspheric surface [1]

| Radius of curvature | | −1.864 | |
|---|---|---|---|
| k | 0.0000e+000 | | |
| a | 1.5065e−001 | b | −4.7179e−002 |

Aspheric surface [2]

| Radius of curvature | | 1.446 | | |
|---|---|---|---|---|
| k | −1.5475e+001 | | | |
| a | 4.2102e−001 | b | −3.1830e−001 | c | 7.7613e−002 |

Decentration [1]

| X | 1.875 | Y | 0.000 | Z | 0.000 |
|---|---|---|---|---|---|
| α | 0.000 | β | 0.000 | γ | 0.000 |
| *1 | | 62.500 | | 18.750 |
| *2 | | 0.125 | | 0.637 |
| *3 | | 0.755 | | 0.243 |

Specifications

| Angle of view | 90° |
|---|---|
| Focal length | 0.867 |
| Stop diameter | φ 1.250 mm |
| Image size | φ 1.000 |
| Effective Fno | 2.185 |

Example 9

| Surface No. | Radius of curvature | Surface separation | Decentration |
|---|---|---|---|
| Object plane | ∞ | *1 50.000 | |
| 1 | Aspheric surface [1] | 0.500 | |
| 2 | Aspheric surface [2] | 0.345 | |
| 3 | −125.536 | 0.750 | |
| 4 | −2.482 | 2.945 | |
| 5 | FFS[1] | 0.625 | Decentration (1) |
| 6 | Spiral surface | 0.063 | |
| 7 | Stop plane | 0.125 | Decentration (2) |
| 8 | −7.332 | 0.375 | |
| 9 | 1.136 | 0.750 | |
| 10 | −3.433 | 0.063 | |
| 11 | 2.450 | 0.625 | |
| 12 | 773.483 | 0.188 | |
| 13 | ∞ | 1.467 | |

-continued

| | | |
|---|---|---|
| 14 | ∞ | 0.500 |
| 15 | ∞ | 0.050 |
| Image plane | ∞ | |

| Surface No. | Refractive index | Abbe constant |
|---|---|---|
| Object plane | | |
| 1 | 1.8830 | 40.7 |
| 2 | | |
| 3 | 1.9229 | 18.9 |
| 4 | | |
| 5 | 1.8830 | 40.7 |
| 6 | | |
| 7 | | |
| 8 | 1.9229 | 18.9 |
| 9 | 1.8830 | 40.7 |
| 10 | | |
| 11 | 1.9229 | 18.9 |
| 12 | | |
| 13 | | |
| 14 | 1.5163 | 64.1 |
| 15 | | |
| Image plane | | |

Aspheric surface [1]

| | | | |
|---|---|---|---|
| Radius of curvature | | −3.129 | |
| k | 0.0000e+000 | | |
| a | 1.5225e−002 | b | −8.7392e−004 |

Aspheric surface [2]

| | | | | | |
|---|---|---|---|---|---|
| Radius of curvature | | 2.002 | | | |
| k | −1.1136e+001 | | | | |
| a | 1.2832e−001 | b | −6.0868e−002 | c | 1.1736e−002 |

Decentration [1]

| | | | | | | | |
|---|---|---|---|---|---|---|---|
| X | 1.500 | Y | 0.000 | Z | 0.000 | | |
| α | 0.000 | β | 0.000 | γ | 0.000 | | |

Decentration [2]

| | | | | | | | |
|---|---|---|---|---|---|---|---|
| X | −1.500 | Y | 0.000 | Z | 0.000 | | |
| α | 0.000 | β | 0.000 | γ | 0.000 | | |

FFS[1]

| | | | | | |
|---|---|---|---|---|---|
| C4 | 7.4954e−003 | C6 | 9.2849e−004 | C11 | −7.3163e−004 |
| C13 | 1.4209e−004 | C15 | 9.7045e−004 | C22 | 4.9732e−005 |
| C24 | 2.8193e−005 | C26 | −2.2641e−004 | C28 | −9.9491e−005 |
| C67 | 2.7000e+001 | | | | |

| | | | |
|---|---|---|---|
| *1 | 50 | 33 | 15 |

Specifications

| | |
|---|---|
| Angle of view | 90° |
| Focal length | 0.953 |
| Stop diameter | φ 1.250 mm |
| Image size | φ 1.000 |
| Effective Fno | 1.664 |

Example 10

| Surface No. | Radius of curvature | Surface separation | Decentration |
|---|---|---|---|
| Object plane | ∞ | *1 83.330 | |
| 1 | ∞ | 0.500 | |
| 2 | Aspheric surface [1] | 1.542 | |
| 3 | 10.745 | 0.400 | |
| 4 | 1.978 | 1.500 | |
| 5 | −8.755 | 0.050 | |
| 6 | 5.086 | 0.600 | |
| 7 | 75.034 | 0.050 | |
| 8 | 3.689 | 1.000 | |
| 9 | −1.998 | 0.400 | |
| 10 | 5.108 | 0.050 | |
| 11 | Stop plane | 0.180 | |
| 12 | −7.317 | 0.600 | |
| 13 | −2.848 | 0.050 | |
| 14 | 8.261 | 0.400 | |
| 15 | 2.533 | 1.300 | |
| 16 | −3.967 | 0.050 | |
| 17 | 3.484 | 1.000 | |
| 18 | −17.964 | 0.100 | |
| 19 | ∞ | 0.150 | |
| 20 | ∞ | 0.000 | Decentration (1) |
| 21 | −48.782 | *2 0.070 | |
| 22 | −40.376 | 0.400 | |
| 23 | ∞ | *3 0.657 | |
| 24 | ∞ | 0.500 | |
| 25 | ∞ | 0.100 | |
| Image plane | ∞ | | Decentration (2) |

| Surface No. | Refractive index | Abbe constant |
|---|---|---|
| Object plane | | |
| 1 | 1.8830 | 40.7 |
| 2 | | |
| 3 | 1.8830 | 40.7 |
| 4 | 1.9229 | 18.9 |
| 5 | | |
| 6 | 1.5174 | 52.4 |
| 7 | | |
| 8 | 1.4875 | 70.2 |
| 9 | 1.9229 | 18.9 |
| 10 | | |
| 11 | | |
| 12 | 1.8830 | 40.7 |
| 13 | | |
| 14 | 1.9229 | 18.9 |
| 15 | 1.6398 | 34.5 |
| 16 | | |
| 17 | 1.8830 | 40.7 |
| 18 | | |
| 19 | | |
| 20 | 1.8830 | 40.7 |
| 21 | | |
| 22 | 1.8830 | 40.7 |
| 23 | | |
| 24 | 1.5163 | 64.1 |
| 25 | | |
| Image plane | | |

Aspheric surface [1]

| | | |
|---|---|---|
| Radius of curvature | | 1.232 |
| k | −9.2269e−001 | |

Decentration [1]

| | | | | | | | |
|---|---|---|---|---|---|---|---|
| X | 2.250 | Y | 0.000 | Z | 0.000 | | |
| α | 0.000 | β | 0.000 | γ | 0.000 | | |

Decentration [2]

| | | | | | | | |
|---|---|---|---|---|---|---|---|
| X | −2.258 | Y | 0.000 | Z | 0.000 | | |
| α | 0.000 | β | 0.000 | γ | 0.000 | | |

| | | | |
|---|---|---|---|
| *1 | 88.330 | 41.670 | 25.000 |
| *2 | 0.070 | 0.184 | 0.340 |
| *3 | 0.657 | 0.543 | 0.387 |

Specifications

| | |
|---|---|
| Angle of view | 140° |
| Focal length | 0.816 |
| Stop diameter | φ 1.400 mm |
| Image size | φ 2.000 |
| Effective Fno | 1.474 |

Example 11

| Surface No. | Radius of curvature | Surface separation | Decentration |
|---|---|---|---|
| 19 | ∞ | 0.000 | Decentration (1) |
| 20 | ∞ | 0.400 | |
| 21 | 36.987 | *2 0.336 | |
| 22 | 30.471 | 0.500 | |
| 23 | ∞ | *3 0.390 | |

| Surface No. | Refractive index | Abbe constant |
|---|---|---|
| Object plane | | |
| 19 | | |
| 20 | 1.8830 | 40.7 |
| 21 | | |
| 22 | 1.8830 | 40.7 |
| 23 | | |
| *1 | 88.330 | 41.670 | 25.000 |
| *2 | 0.335 | 0.211 | 0.080 |
| *3 | 0.390 | 0.514 | 0.645 |

The specifications are the same as in Example 10.

Example 12

| Surface No. | Radius of curvature | Surface separation | Decentration |
|---|---|---|---|
| 19 | ∞ | *2 0.060 | |
| 20 | ∞ | 0.400 | |
| 21 | 55.300 | *3 0.654 | |
| 22 | 29.140 | 0.500 | |
| 23 | ∞ | 0.100 | |

| Surface No. | Refractive index | Abbe constant |
|---|---|---|
| Object plane | | |
| 19 | | |
| 20 | 1.8830 | 40.7 |
| 21 | | |
| 22 | 1.8830 | 40.7 |
| 23 | | |
| *1 | 88.330 | 41.670 | 25.000 |
| *2 | 0.060 | 0.243 | 0.500 |
| *3 | 0.655 | 0.472 | 0.215 |

The specifications are the same as in Example 10.

Example 13

| Surface No. | Radius of curvature | Surface separation | Decentration |
|---|---|---|---|
| 19 | ∞ | *2 0.533 | |
| 20 | ∞ | 0.400 | |
| 21 | 36.987 | *3 0.200 | |
| 22 | 30.471 | 0.500 | |
| 23 | ∞ | 0.100 | |

| Surface No. | Refractive index | Abbe constant |
|---|---|---|
| Object plane | | |
| 19 | | |
| 20 | 1.8830 | 40.7 |
| 21 | | |
| 22 | 1.8830 | 40.7 |
| 23 | | |
| *1 | 88.330 | 41.670 | 25.000 |
| *2 | 0.533 | 0.304 | 0.050 |
| *3 | 0.200 | 0.429 | 0.683 |

The specifications are the same as in Example 10.

Example 14

| Surface No. | Radius of curvature | Surface separation | Decentration |
|---|---|---|---|
| 19 | ∞ | *2 0.218 | |
| 20 | −33.491 | 0.300 | |
| 21 | −35.533 | *3 0.832 | |

| Surface No. | Refractive index | Abbe constant |
|---|---|---|
| Object plane | | |
| 19 | | |
| 20 | 1.8978 | 28.2 |
| 21 | | |
| *1 | 88.330 | 41.670 | 25.000 |
| *2 | 0.218 | 0.456 | 0.950 |
| *3 | 0.832 | 0.594 | 0.100 |

The specifications are the same as in Example 10.

Set out below are the values of Conditions (1) and (2) in the aforesaid examples.

| Condition | Example 6 | Example 7 | Example 8 | Example 9 |
|---|---|---|---|---|
| (1)d/f | | | | 0.082 |
| f | 0.423 | 0.412 | 0.867 | |
| fb | 22.670 | 10.942 | 32.555 | |
| (2)fb/f | 53.522 | 26.558 | 37.549 | |

| Condition | Example 10 | Example 11 | Example 12 | Example 13 |
|---|---|---|---|---|
| f | 0.816 | 0.815 | 0.812 | 0.817 |
| fb | −267.332 | 187.376 | 68.254 | −111.459 |
| dv | 0.270 | 0.255 | 0.440 | 0.483 |
| (2)fb/f | −352.113 | 229.909 | 84.057 | −136.425 |
| (3)dv/f | 0.331 | 0.313 | 0.542 | 0.591 |

| Condition | Example 14 |
|---|---|
| f | 1.335 |
| fb | −697.476 |
| dv | 0.732 |
| (2)fb/f | −522.454 |
| (3)dv/f | 0.548 |

Exemplary applications of the optical system assembly 1 according to the invention are now explained.

Preferably, the stereoscopic imaging optical system assembly described herein is used in the form of a stereoscopic imaging apparatus located on the aforesaid image plane and including an imaging device having multiple pixels.

By use of the stereoscopic imaging apparatus described here, it is possible to achieve size reductions for stereoscopic imaging apparatuses.

Preferably, the stereoscopic imaging optical system assembly described herein is also used in the form of an endoscope having a stereoscopic imaging apparatus.

The stereoscopic imaging optical apparatus described herein enables focus and vergence modifications to be implemented in a very simple operation, contributing to improvements in the performance of a small-sized device such as an endoscope.

More preferably, a focusing detection unit, a distance-measuring unit or the like is used for automatic focus control.

Figure 82A:
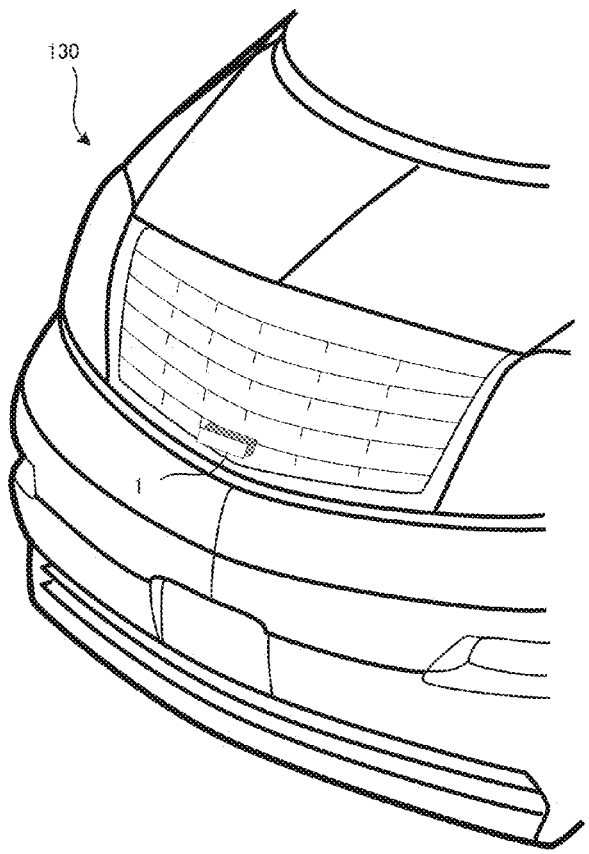
FIGS. 82A and 82B are illustrative of an example using the optical system assembly of the invention as an automotive imaging optical system.
Figure 82B:
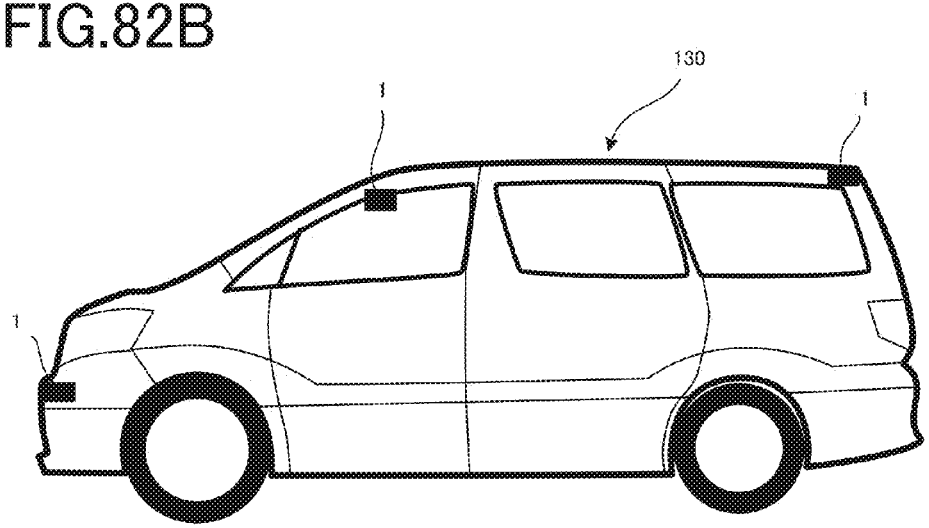

FIGS. 82A and 82B are illustrative of an example using the optical system assembly embodied by the invention as an imaging optical system in automotive applications.

FIG. 82A shows a front of a car body 130 to which the optical system assemblies 1 according to one embodiment described herein are attached such that images taken by each optical system assembly 1 and subjected to various image processes for distortion correction are simultaneously shown on an onboard display, and FIG. 82B shows an example wherein multiple optical system assemblies 1 are attached as stereoscopic imaging apparatus to the corners and the pole of the head of the car body 130 such that images taken by the respective optical system assemblies 1 and subjected to various image processes for distortion correction are concurrently and stereoscopically shown on an onboard display.

Figure 83A:
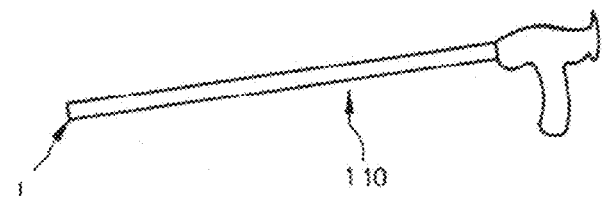
FIGS. 83A, 83B and 83C are illustrative of an example using the optical system assembly of the invention as an imaging optical system at the distal end of an endoscope.
Figure 83B:
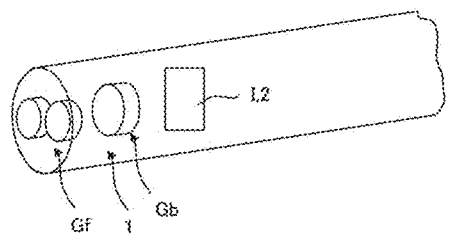
Figure 83C:
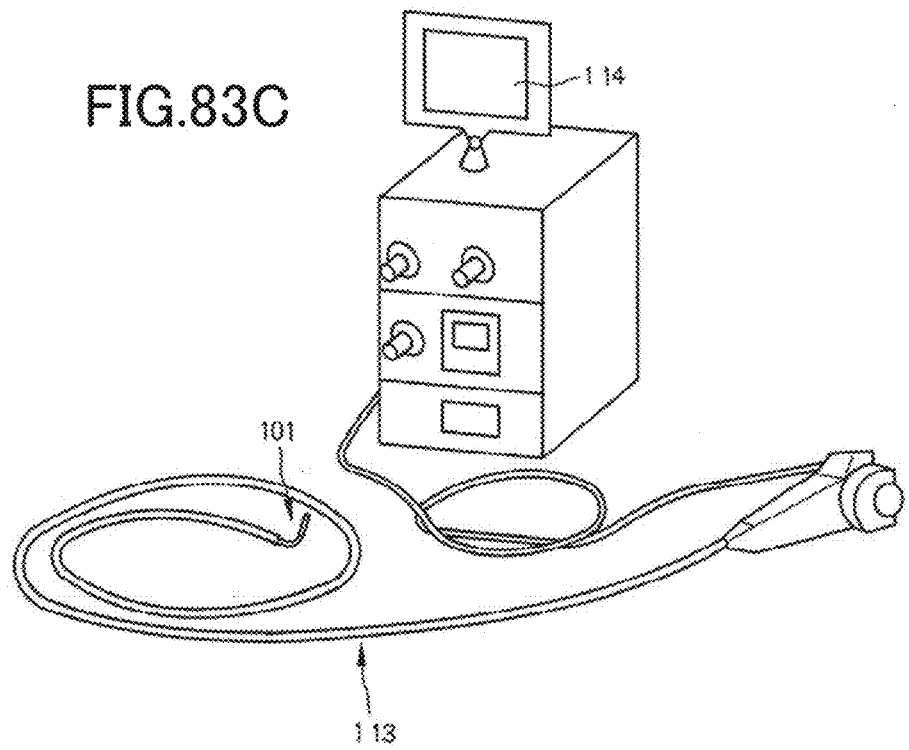

FIGS. 83A, 83B and 83C show an example using the optical system assembly embodied by the invention as an imaging optical system at the distal end of an endoscope.

FIGS. 83A, 83B and 83C show an example using the optical system assembly embodied by the invention as an imaging optical system at the distal end of an endoscope. FIG. 83A shows an example wherein the optical system assembly 1 described herein is attached to the distal end of a hard endoscope 110 such that images in full 360°-directions are stereoscopically taken and viewed, and FIG. 83B shows a schematic construction and arrangement of the distal end. FIG. 83C shows an example wherein the optical system assembly 1 described herein is similarly attached to the distal end of a soft electronic endoscope 113 such that images taken through it and subjected to image processing for distortion correction are stereoscopically displayed.

As depicted in FIGS. 83A, 83B and 83C, application of the optical system assembly 1 or the stereoscopic imaging apparatus to the endoscope enables images in full directions to be taken and viewed so that various sites can be stereoscopically imaged and viewed at angles different than in conventional manners.

While the invention has been explained with reference to various embodiments, it is to be appreciated that the invention is in no sense limited thereto and appropriate combinations of them are included within the category of the invention as well.

What is claimed is:

1. A stereoscopic imaging optical system assembly, comprising:
a first optical system at least including, in order from an object side to an image plane side, a negative lens and an aperture, said first optical system being rotationally symmetric with respect to a first center axis,
a second optical system that is rotationally symmetric with respect to a second center axis parallel with said first center axis, and that has the same construction as, and is located in parallel with, said first optical system, and
a variable optical system located in such a way as to intersect respective optical paths through said first optical system and said second optical system, wherein:
said variable optical system includes at least one variable optical element,
said variable optical element effects a change of at least either one of focus and vergence simultaneously with respect to said first optical system and said second optical system, has a transmission surface, and gives equal refracting action on said first optical system and said second optical system,
said first optical system and said second optical system each include a rear group, and
said variable optical system is located on an image plane side with respect to said front groups and rear groups, and wherein said variable optical element has a single center axis of rotation, wherein:
said variable optical element rotates with said center axis of rotation as center, causing a change in positions where said variable optical element intersects the respective optical paths through said first optical system and said second optical system, and depending on the positions where said variable optical element intersects the respective optical paths through said first optical system and said second optical system, at least either one of focus and vergence is varied.

2. A stereoscopic imaging optical system assembly as recited in claim 1, wherein said variable optical element is in a rotationally symmetric configuration with said center axis of rotation as an axis of symmetry.

3. A stereoscopic imaging optical system assembly as recited in claim 2, wherein said variable optical element includes at least one set of a first surface portion and a second surface portion that has the same construction as said first surface portion and is located in a position rotated at a given angle with respect to said first surface portion with said center axis of rotation as center.

4. A stereoscopic imaging optical system assembly as recited in claim 3, wherein said first surface portion and said second surface portion each at least include a first planar portion comprising a plane orthogonal to said center axis of rotation and a second planar portion comprising a plane orthogonal to said center axis of rotation and different from said first planar portion in terms of a thickness in said center-axis-of-rotation direction.

5. A stereoscopic imaging optical system assembly as recited in claim 3, wherein said first surface portion and said second surface portion each comprise at least one tilting surface that tilts at a given angle of tilt.

6. A stereoscopic imaging optical system assembly as recited in claim 3, wherein said first surface portion and said second surface portion each comprise at least helicoidal surface that tilts in a peripheral direction of a circle with said center axis of rotation as center.

7. A stereoscopic imaging optical system assembly as recited in claim 3, wherein said first surface portion and said second surface portion each comprise at least one radially tilting surface having a radial angle with respect to said center axis of rotation, said radial angle changing continuously in a peripheral direction of a circle with said center axis of rotation as center.

8. A stereoscopic imaging optical system assembly as recited in claim 1, wherein said variable optical element includes at least one curved surface having a changing partial curvature.

9. A stereoscopic imaging optical system assembly as recited in claim 8, wherein said curved surface is a free-form surface.

10. A stereoscopic imaging apparatus comprising:
a stereoscopic imaging optical system assembly as recited in claim 1, and
an imaging device located on said image plane and including a plurality of pixels.

11. An endoscope, characterized by comprising:
a stereoscopic imaging apparatus as recited in claim 10.

* * * * *